US011801309B2

(12) United States Patent
Yang et al.

(10) Patent No.: US 11,801,309 B2
(45) Date of Patent: Oct. 31, 2023

(54) CARBOHYDRATE-FUNCTIONALIZED NANOPARTICLES AND USES THEREOF

(71) Applicant: VIRGINIA COMMONWEALTH UNIVERSITY INTELLECTUAL PROPERTY FOUNDATION, Richmond, VA (US)

(72) Inventors: Hu Yang, Glen Allen, VA (US); Shobha Ghosh, Glen Allen, VA (US); Hongliang He, Richmond, VA (US); Michael Lancina, Richmond, VA (US)

(73) Assignee: Virginia Commonwealth University Intellectual Property Foundation, Richmond, VA (US)

( * ) Notice: Subject to any disclaimer, the term of this patent is extended or adjusted under 35 U.S.C. 154(b) by 642 days.

(21) Appl. No.: 16/345,303

(22) PCT Filed: Oct. 27, 2017

(86) PCT No.: PCT/US2017/058694
§ 371 (c)(1),
(2) Date: Apr. 26, 2019

(87) PCT Pub. No.: WO2018/081517
PCT Pub. Date: May 3, 2018

(65) Prior Publication Data
US 2021/0322567 A1    Oct. 21, 2021

Related U.S. Application Data

(60) Provisional application No. 62/461,658, filed on Feb. 21, 2017, provisional application No. 62/413,667, filed on Oct. 27, 2016.

(51) Int. Cl.
| | |
|---|---|
| A61K 47/69 | (2017.01) |
| A61K 47/60 | (2017.01) |
| A61P 9/10 | (2006.01) |
| A61K 31/7105 | (2006.01) |
| A61K 38/46 | (2006.01) |
| A61K 47/26 | (2006.01) |

(52) U.S. Cl.
CPC ...... *A61K 47/6935* (2017.08); *A61K 31/7105* (2013.01); *A61K 38/465* (2013.01); *A61K 47/26* (2013.01); *A61K 47/60* (2017.08); *A61P 9/10* (2018.01)

(58) Field of Classification Search
None
See application file for complete search history.

(56) References Cited

U.S. PATENT DOCUMENTS

| | | |
|---|---|---|
| 2008/0226739 A1 | 9/2008 | Wood et al. |
| 2013/0004427 A1 | 1/2013 | El-Sayed et al. |

FOREIGN PATENT DOCUMENTS

| | | |
|---|---|---|
| CN | 1957945 | 5/2007 |
| CN | 101259284 | 9/2008 |
| WO | 2016/025745 | 2/2016 |

OTHER PUBLICATIONS

Qin et al. (Human Gene Therapy, vol. 9, pp. 553-560, Mar. 1998).*
He et al. (Transl. Res., Mar. 2018, vol. 193, pp. 13-30).*
Jaye (Current Opinion in Investigational Drugs, 2003, vol. 4, No. 9, pp. 1053-1058).*
Zhang et al. (Advanced Healthcare Materials, vol. 4 Issue 2, p. 228-236, Aug. 2014).*
International Search Report and Written Opinion dated Mar. 26, 2018, from International Application No. PCT/US2017/058694, 11 pages.
Extended EP Search Report dated May 4, 2020, from related EP Application No. EP17864002, 31 pages.

\* cited by examiner

*Primary Examiner* — Hope A Robinson
(74) *Attorney, Agent, or Firm* — Meunier Carlin & Curfman LLC

(57) ABSTRACT

The present disclosure relates to carbohydrate-functionalized nanoparticles and methods of treating cardiovascular disease (for example, atherosclerosis).

4 Claims, 36 Drawing Sheets
Specification includes a Sequence Listing.

SEQUENCE LISTING

```
<160> NUMBER OF SEQ ID NOS: 3

<210> SEQ ID NO 1
<211> LENGTH: 1704
<212> TYPE: DNA
<213> ORGANISM: Homo sapiens

<400> SEQUENCE: 1
atgtggctcc gtgcctttat cctggccact ctctctgctt ccgcggcttg ggggcatccg      60
tcctcgccac ctgtggtgga caccgtgcat ggcaaagtgc tggggaagtt cgtcagctta     120
gaaggatttg cacagcctgt ggccattttc ctgggaatcc cttttgccaa gccgcctctt     180
ggacccctga ggtctactcc accgcagcct gcagaaccat ggagctttgt gaagaatgcc     240
acctcgtacc ctcctatgtg cacccgagat cccaaggcgg ggcagttact ctcagagcta     300
tttacaaacc gaaaggagaa cattcctctc aagctttctg aagactgtct ttacctcaat     360
atttacactc ctgctgactt gaccaagaaa aacaggctgc cggtgatggt gtggatccac     420 ggagggggc tgatggtggg tgcggcatca acctatgatg ggctggccct tgctgccat      480 gaaaacgtgg tggtggtgac cattcaatat cgcctgggca tctggggatt cttcagcaca     540
ggggatgaac acagccgggg gaactggggt cacctggacc aggtggctgc cctgcgctgg     600
gtccaggaca acattgccag ctttggaggg aacccaggct ctgtgaccat ctttggagag     660
tcagcgggag gagaaagtgt ctctgttctt gttttgtctc cattggccaa gaacctcttc     720
caccgggcca tttctgagag tggcgtggcc ctcacttctg ttctggtgaa gaaaggtgat     780
```

| | |
|---|---|
| gtcaagccct tggctgagca aattgctatc actgctgggt gcaaaaccac cacctctgct | 840 |
| gtcatggttc actgcctgcg acagaagacg aagaggagc tcttggagac gacattgaaa | 900 |
| atgaaattct tatctctgga cttacaggga accccagag agagtcaacc ccttctgggc | 960 |
| actgtgattg atgggatgct gctgctgaaa acacctgaag agcttcaagc tgaaaggaat | 1020 |
| ttccacactg tccctacat ggtcggaatt aacaagcagg agtttggctg gttgattcca | 1080 |
| atgcagttga tgagctatcc actctccgaa gggcaactgg accagaagac agccatgtca | 1140 |
| ctcctgtgga agtcctatcc ccttgtttgc attgctaagg aactgattcc agaagccact | 1200 |
| gagaaatact taggaggaac agacgacact gtcaaaaaga aagacctgtt cctggacttg | 1260 |
| atagcagatg tgatgtttgg tgtcccatct gtgattgtgg cccggaacca cagagatgct | 1320 |
| ggagcaccca cctacatgta tgagtttcag taccgtccaa gcttctcatc agacatgaaa | 1380 |
| cccaagacgg tgataggaga ccacggggat gagctcttct ccgtctttgg ggccccattt | 1440 |
| ttaaaagagg gtgcctcaga agaggagatc agacttagca agatggtgat gaaattctgg | 1500 |
| gccaactttg ctcgcaatgg aaaccccaat ggggaagggc tgccccactg gccagagtac | 1560 |
| aaccagaagg aagggtatct gcagattggt gccaacaccc aggcggccca agagctgaag | 1620 |
| gacaaagaag tagcttttctg gaccaacctc tttgccaaga aggcagtgga aagccaccc | 1680 |
| cagacagaac acatagagct gtga | 1704 |

<210> SEQ ID NO 2
<211> LENGTH: 1947
<212> TYPE: DNA
<213> ORGANISM: Homo sapiens

<400> SEQUENCE: 2

| | |
|---|---|
| ctgtacagag acctcgcagg ccccgagaac tgtcgccttc cacgatgtgg ctccgtgcct | 60 |
| ttatcctggc cactctctct gcttccgcgg cttggggca tccgtcctcg ccacctgtgg | 120 |
| tggacaccgt gcatggcaaa gtgctgggga agttcgtcag cttagaagga tttgcacagc | 180 |
| ctgtggccat tttcctggga atcccttttg ccaagccgcc tcttggaccc ctgaggtcta | 240 |
| ctccaccgca gcctgcagaa ccatggagct tgtgaagaa tgccacctcg taccctccta | 300 |
| tgtgcacccg agatcccaag gcggggcagt tactctcaga gctatttaca aaccgaaagg | 360 |
| agaacattcc tctcaagctt tctgaagact gtctttacct caatatttac actcctgctg | 420 |
| acttgaccaa gaaaaacagg ctgccggtga tggtgtggat ccacggaggg gggctgatgg | 480 |
| tgggtgcggc atcaacctat gatgggctgg cccttgctgc ccatgaaaac gtggtggtgg | 540 |
| tgaccattca atatcgcctg ggcatctggg gattcttcag cacaggggat gaacacagcc | 600 |
| gggggaactg gggtcacctg gaccaggtgg ctgccctgcg ctgggtccag acaacattg | 660 |
| ccagctttgg agggaaccca ggctctgtga ccatctttgg agagtcagcg ggaggagaaa | 720 |
| gtgtctctgt tcttgttttg tctccattgg ccaagaacct cttccaccgg gccatttctg | 780 |
| agagtggcgt ggccctcact tctgttctgg tgaagaagg tgatgtcaag cccttggctg | 840 |
| agcaaattgc tatcactgct gggtgcaaaa ccaccacctc tgctgtcatg gttcactgcc | 900 |
| tgcgacagaa gacggaagag gagctcttgg agacgacatt gaaatgaaa ttcttatctc | 960 |
| tggacttaca gggagacccc agagagagtc aaccccttct gggcactgtg attgatggga | 1020 |
| tgctgctgct gaaaacacct gaagagcttc aagctgaaag gaatttccac actgtcccct | 1080 |
| acatggtcgg aattaacaag caggagtttg gctggttgat tccaatgcag ttgatgagct | 1140 |
| atccactctc cgaagggcaa ctggaccaga agacagccat gtcactcctg tggaagtcct | 1200 |

```
atccccttgt tgcattgct aaggaactga ttccagaagc cactgagaaa tacttaggag    1260
gaacagacga cactgtcaaa agaaagacc tgttcctgga cttgatagca gatgtgatgt    1320
ttggtgtccc atctgtgatt gtggcccgga accacagaga tgctggagca cccacctaca    1380
tgtatgagtt tcagtaccgt ccaagcttct catcagacat gaaacccaag acggtgatag    1440
gagaccacgg ggatgagctc ttctccgtct ttggggcccc attttttaaaa gagggtgcct    1500 cagaagagga gatcagactt agcaagatgg tgatgaaatt ctgggccaac tttgctcgca    1560
atggaaaccc caatggggaa gggctgcccc actggccaga gtacaaccag aaggaagggt    1620
atctgcagat tggtgccaac acccaggcgg cccagaagct gaaggacaaa gaagtagctt    1680
tctggaccaa cctctttgcc aagaaggcag tggagaagcc accccagaca gaacacatag    1740
agctgtgaat gaagatccag ccggccttgg gagcctggag gagcaaagac tggggtcttt    1800
tgcgaaaggg attgcaggct cagaaggcat cttaccatgg ctggggaatt gtctggtggt    1860 gggggcagg ggacagaggc catgaaggag caagttttgt attgtgacct cagctttggg    1920
aataagatct tttgaaggca aaaaaa                                         1947

<210> SEQ ID NO 3
<211> LENGTH: 567
<212> TYPE: PRT
<213> ORGANISM: Homo sapiens

<400> SEQUENCE: 3

Met Trp Leu Arg Ala Phe Ile Leu Ala Thr Leu Ser Ala Ser Ala Ala
1               5                   10                  15

Trp Gly His Pro Ser Ser Pro Val Val Asp Thr Val His Gly Lys
            20                  25                  30

Val Leu Gly Lys Phe Val Ser Leu Glu Gly Phe Ala Gln Pro Val Ala
        35                  40                  45

Ile Phe Leu Gly Ile Pro Phe Ala Lys Pro Pro Leu Gly Pro Leu Arg
    50                  55                  60

Ser Thr Pro Pro Gln Pro Ala Glu Pro Trp Ser Phe Val Lys Asn Ala
65                  70                  75                  80

Thr Ser Tyr Pro Pro Met Cys Thr Arg Asp Pro Lys Ala Gly Gln Leu
                85                  90                  95

Leu Ser Glu Leu Phe Thr Asn Arg Lys Glu Asn Ile Pro Leu Lys Leu
            100                 105                 110

Ser Glu Asp Cys Leu Tyr Leu Asn Ile Tyr Thr Pro Ala Asp Leu Thr
        115                 120                 125

Lys Lys Asn Arg Leu Pro Val Met Val Trp Ile His Gly Gly Gly Leu
    130                 135                 140

Met Val Gly Ala Ala Ser Thr Tyr Asp Gly Leu Ala Leu Ala Ala His
145                 150                 155                 160

Glu Asn Val Val Val Thr Ile Gln Tyr Arg Leu Gly Ile Trp Gly
                165                 170                 175

Phe Phe Ser Thr Gly Asp Glu His Ser Arg Gly Asn Trp Gly His Leu
            180                 185                 190

Asp Gln Val Ala Ala Leu Arg Trp Val Gln Asp Asn Ile Ala Ser Phe
        195                 200                 205

Gly Gly Asn Pro Gly Ser Val Thr Ile Phe Gly Glu Ser Ala Gly Gly
    210                 215                 220

Glu Ser Val Ser Val Leu Val Leu Ser Pro Leu Ala Lys Asn Leu Phe
225                 230                 235                 240
```

```
His Arg Ala Ile Ser Glu Ser Gly Val Ala Leu Thr Ser Val Leu Val
                245                 250                 255

Lys Lys Gly Asp Val Lys Pro Leu Ala Glu Gln Ile Ala Ile Thr Ala
            260                 265                 270

Gly Cys Lys Thr Thr Thr Ser Ala Val Met Val His Cys Leu Arg Gln
            275                 280                 285

Lys Thr Glu Glu Glu Leu Leu Glu Thr Thr Leu Lys Met Lys Phe Leu
        290                 295                 300

Ser Leu Asp Leu Gln Gly Asp Pro Arg Glu Ser Gln Pro Leu Leu Gly
305                 310                 315                 320

Thr Val Ile Asp Gly Met Leu Leu Leu Lys Thr Pro Glu Glu Leu Gln
                325                 330                 335

Ala Glu Arg Asn Phe His Thr Val Pro Tyr Met Val Gly Ile Asn Lys
            340                 345                 350

Gln Glu Phe Gly Trp Leu Ile Pro Met Gln Leu Met Ser Tyr Pro Leu
            355                 360                 365

Ser Glu Gly Gln Leu Asp Gln Lys Thr Ala Met Ser Leu Leu Trp Lys
        370                 375                 380

Ser Tyr Pro Leu Val Cys Ile Ala Lys Glu Leu Ile Pro Glu Ala Thr
385                 390                 395                 400

Glu Lys Tyr Leu Gly Gly Thr Asp Asp Thr Val Lys Lys Lys Asp Leu
            405                 410                 415

Phe Leu Asp Leu Ile Ala Asp Val Met Phe Gly Val Pro Ser Val Ile
            420                 425                 430

Val Ala Arg Asn His Arg Asp Ala Gly Ala Pro Thr Tyr Met Tyr Glu
            435                 440                 445

Phe Gln Tyr Arg Pro Ser Phe Ser Ser Asp Met Lys Pro Lys Thr Val
        450                 455                 460

Ile Gly Asp His Gly Asp Glu Leu Phe Ser Val Phe Gly Ala Pro Phe
465                 470                 475                 480

Leu Lys Glu Gly Ala Ser Glu Glu Glu Ile Arg Leu Ser Lys Met Val
            485                 490                 495

Met Lys Phe Trp Ala Asn Phe Ala Arg Asn Gly Asn Pro Asn Gly Glu
            500                 505                 510

Gly Leu Pro His Trp Pro Glu Tyr Asn Gln Lys Glu Gly Tyr Leu Gln
            515                 520                 525

Ile Gly Ala Asn Thr Gln Ala Ala Gln Lys Leu Lys Asp Lys Glu Val
        530                 535                 540

Ala Phe Trp Thr Asn Leu Phe Ala Lys Lys Ala Val Glu Lys Pro Pro
545                 550                 555                 560

Gln Thr Glu His Ile Glu Leu
                565
```

CARBOHYDRATE-FUNCTIONALIZED NANOPARTICLES AND USES THEREOF

CROSS-REFERENCE TO RELATED APPLICATIONS

This application claims the benefit of U.S. Provisional Patent Application Ser. No. 62/413,667 filed Oct. 27, 2016 and U.S. Provisional Patent Application Ser. No. 62/461,658 filed Feb. 21, 2017, the disclosures of which are expressly incorporated herein by reference.

STATEMENT REGARDING FEDERALLY SPONSORED RESEARCH

This invention was made with Government Support under Grant No. CBET0954957, awarded by the National Science Foundation. The Government has certain rights in this invention.

FIELD

The present disclosure relates to carbohydrate-functionalized nanoparticles and methods of treating cardiovascular disease (for example, atherosclerosis).

BACKGROUND

Cardiovascular disease (CVD) continues to be the number one cause of morbidity and mortality in the United States. Accumulation of cholesterol as cholesteryl esters (CE) in artery wall associated macrophage foam cells is one of the hallmarks of atherosclerosis, a process that underlies the development of cardiovascular diseases. Current therapeutics only help limit further CE accumulation mainly by reducing endogenous cholesterol synthesis in the liver or limiting absorption of dietary cholesterol. However, these agents cannot remove cholesterol from existing atherosclerotic plaques. What is needed are new compositions and methods that can be used to deliver therapeutic agents to remove cholesterol from plaques.

Although viral vectors have been the most efficient systems for gene delivery in vivo and have been successfully used in pre-clinical animal studies for functional validation of genes, major drawbacks include high immunogenicity, high levels of pre-existing immunity, transient expression of the transgene, and low capacity to accommodate certain genes required for clinical applications. With the advancement of nanotechnology, development of nanomedicines to efficiently target dysfunctional macrophages can strengthen the effectiveness of therapeutics and improve clinical outcomes. While folate-functionalized nanomedicines to target cancerous tissue-associated macrophages have been described, current strategies to target dysfunctional macrophages in other chronic diseases such as atherosclerosis are very limited.

The compounds, compositions, and methods disclosed herein address these and other needs.

SUMMARY

Disclosed herein are novel carbohydrate-functionalized nanoparticles for specific delivery of therapeutic payloads. In some embodiments, the inventors found that mannose functionalized dendrimeric nanoparticles (mDNP) can target delivery of a therapeutic compound (for example, a cholesteryl ester (CE) modulator) to plaque-associated macrophages, and eliminate the undesirable lipogenic effects in liver. In addition, the data also show that targeted delivery of liver-x-receptor ligand (LXR-L) to atherosclerotic plaques-associated macrophages results in plaque attenuation and favorable modulation of plaque characteristics. Furthermore, conjugation of the carbohydrate to the dendrimer nanoparticle using extended polyethylene glycol (PEG) linkers prevented agglomeration, decreased the highly positive charge on the surface, and increased the high steric exclusion.

In some embodiments, functionalization of dendrimeric nanoparticles with galactose increased liver-specific delivery, and the use of a long PEG linker for galactose attachment also reduced the toxicity associated with high positive charges on the surface of the unmodified nanoparticle. The development of this non-toxic/non-viral and efficient liver-specific gene delivery platform can be used for enhancing removal of cholesterol from the body to reduce the existing atherosclerotic plaque burden for which no therapeutics are currently available.

In some aspects, disclosed herein is a nanoparticle comprising: a polyamidoamine (PAMAM) dendrimer; a carbohydrate moiety, wherein the carbohydrate moiety is linked to the polyamidoamine (PAMAM) dendrimer via a polyethylene glycol (PEG) linker, and wherein the PEG linker comprises at least four individual PEG units; and a therapeutic agent.

In some embodiments, the carbohydrate moiety is mannose. In some embodiments, the carbohydrate moiety is galactose. In some embodiments, the PEG linker comprises PEG (3.5K). In some embodiments, the therapeutic agent is an intracellular cholesteryl ester (CE) modulator. In some embodiments, the intracellular cholesteryl ester (CE) modulator is an LXR agonist. In some embodiments, the LXR agonist is T0901317 or GW3965. In some embodiments, the LXR agonist is linked to the polyamidoamine (PAMAM) dendrimer via a polyethylene glycol (PEG) linker. In some embodiments, the intracellular cholesteryl ester (CE) modulator is an expression vector comprising a cholesteryl ester hydrolase (CEH) gene. In some embodiments, the expression vector comprising a cholesteryl ester hydrolase (CEH) gene is encapsulated within the nanoparticle.

In some embodiments, the nanoparticle further comprises an siRNA targeting scavenger receptor A (SR-A) or an siRNA targeting CD-36.

In some aspects, disclosed herein is a method of treating cardiovascular disease, comprising: administering to a subject in need thereof a nanoparticle comprising: a polyamidoamine (PAMAM) dendrimer; a carbohydrate moiety, wherein the carbohydrate moiety is linked to the polyamidoamine (PAMAM) dendrimer via a polyethylene glycol (PEG) linker, and wherein the PEG linker comprises at least four individual PEG units; and a therapeutic agent.

In some embodiments, the cardiovascular disease is atherosclerosis.

In some aspects, disclosed herein is a method for delivery of a therapeutic agent to a plaque-associated macrophage, comprising: administering to a subject a nanoparticle comprising: a polyamidoamine (PAMAM) dendrimer; a carbohydrate moiety, wherein the carbohydrate moiety is linked to the polyamidoamine (PAMAM) dendrimer via a polyethylene glycol (PEG) linker, and wherein the PEG linker comprises at least four individual PEG units; and a therapeutic agent; wherein the therapeutic agent is delivered to a plaque-associated macrophage.

In another aspect, disclosed herein is a method for delivery of a therapeutic agent to a hepatocyte, comprising:

administering to a subject a nanoparticle comprising: a polyamidoamine (PAMAM) dendrimer; a carbohydrate moiety, wherein the carbohydrate moiety is linked to the polyamidoamine (PAMAM) dendrimer via a polyethylene glycol (PEG) linker, and wherein the PEG linker comprises at least four individual PEG units; and a therapeutic agent; wherein the therapeutic agent is delivered to a hepatocyte.

BRIEF DESCRIPTION OF THE DRAWINGS

The accompanying figures, which are incorporated in and constitute a part of this specification, illustrate several aspects described below.

FIG. 2A: Schematic to show the steps involved in the synthesis. LXR-L was PEGylated and then coupled with DNP G5.0 to form DNP-LXR-L. Mannose-PEG-NHS was conjugated with DNP-LXR-L to get mDNP-LXR-L. To facilitate in vitro and in vivo imaging, mDNP-LXR-L was labeled with either FITC or 800CW. FIG. 2B: The 300 MHz$^1$H NMR spectrum of pure PAMAM G5, Mannose-PEG-NHS, LXR-L and mDNP-LXR-L. In the spectrum of mDNP-LXR-L, multiple protons peaks between 2.2 and 3.4 ppm belong to protons from PAMAM G5; a singlet peak at 3.6 ppm belongs to the repeat units of PEG in Mannose-PEG-NHS and peaks in the red triangle stand for the LXR-L. FIG. 2C: Morphology of mDNP-LXR-L visualized by TEM. FIG. 2D: Hydrodynamic size of mDNP-LXR-L measured by DLS. FIG. 2E: Changes on zeta potential of mDNP-LXR-L in colloidal state over 24 h. FIG. 2F: Changes on size of mDNP-LXR-L in colloidal state over 24 h.

FIG. 3A: Freshly isolated MPMs ($0.8 \times 10^6$ cells/well) were plated in 48 well plates and growth medium was changed after 4 h. After 24 h, the growth medium was replaced with fresh medium containing increasing concentrations of mDNP-LXR-L and incubated for additional 24 h. Cell viability was determined using WST-1 assay. FIG. 3B: Freshly isolated hepatocytes ($0.3 \times 10^6$ cells/well) were plated in 48 well plates and growth medium was changed after 4 h. After 24 h, the growth medium was replaced with fresh medium containing increasing concentrations of mDNP-LXR-L and incubated for additional 24 h. Cell viability was determined using WST-1 assay. Data are expressed as % cell viability compared to No treatment control (Mean±SD, n=6)

FIG. 4A: Total protein extracts prepared from freshly isolated MPMs as well as primary mouse hepatocytes were subjected to Western blot analyses to evaluate the expression of Mannose receptor. Blots were stripped and re-probed with β-actin as the housekeeping gene. FIG. 4B: MPMs as well as hepatocytes were plated in 2-well chamber slides as described under "Methods" and incubated with mDNP-FITC (0.2 µM) for 24 h. Cells were washed with PBS, fixed with buffered formalin and imaged using Carl Zeiss inverted fluorescent microscope. FIG. 4C: MPMs as well as hepatocytes were plated in 6-well tissue culture dishes and incubated with mDNP-FITC (0.2 µM). After 24 h, cells were harvested and cell associated FITC fluorescence was determined by FACS. Data (Mean±SD, n=6) are shown as mean fluorescent intensities.

FIG. 5A: Freshly isolated MPMs were plated in 2-well chamber slides and incubated with increasing concentration of either FITC (Green) labeled DNP (DNP-FITC) or with FITC labeled mannose functionalized DNP (mDNP-FITC) for 24 h. FIG. 5B: Freshly isolated MPMs were plated in 2-well chamber slides and incubated with 0.2 µM of either DNP-FITC or with mDNP-FITC for indicates time periods. Cells were washed with PBS, permeabilized, counterstained with nuclear stain DAPI (Blue) and imaged as described under "Methods". Representative images from three independent experiments are shown. FIG. 5C: MPMs were plated in 24-well plates and incubated with mDNP-FITC (0.2 µM) in the absence or presence of mannose receptor antagonist, Mannan (0.1 mM). After 24 h, the cells were harvested and cell associated FITC fluorescence was determined by FACS. Data (Mean±SD, n=6) are shown as mean fluorescent intensities.

FIGS. 6A and 6B: MPMs (FIG. 6A) or Primary hepatocytes (FIG. 6B) were plated in 6-well culture dishes and incubated with either LXR ligand T0901317 or mDNP or mDNP-LXR-L (0.2 µM) for 24 h; untreated cells were used as Controls. Expression of LXR target genes (ABCA1 and ABCG1 in MPMs and FAS and SREBP1 in hepatocytes) was evaluated by QPCR using total RNA as described under "Methods". Data (Mean±SD, n=3) are expressed as fold increase over Controls. FIG. 6C: MPMs were plated in 6-well plates were exposed to either LXR ligand T0901317 or mDNP or mDNP-LXR-L (0.2 µM) for 24 h. Cells were washed once with cold PBS and harvested in cold buffer on ice as described under "Methods". Following disruption of cells by sonication and removal of cell debris, CEH activity was measured using a radiometric assay. CEH activity (Mean±SD, n=3) is expressed as % untreated Controls. FIG. 6D: MPMs, plated in 24-well plate, were loaded and labeled with [$^3$H]-cholesterol as described under "Methods". During the 24 h equilibration, cells were exposed to either LXR ligand T0901317 or mDNP or mDNP-LXR-L (0.2 µM). FC efflux to medium containing 10% FBS was monitored for 8 and 24 h. Data (Mean±SD, n=6) are expressed as % efflux. *P<0.05 and NS—not significant.

FIGS. 7A and 7B: After 24 h, mice were euthanized and major organs (heart, liver, spleen, lung and kidney) as well as entire aorta from the heart to the iliary bifurcation was removed and cleaned to remove all the adventitious tissue. After opening to expose the arterial plaques, the aortas were imaged to assess uptake of fluorescent mDNP. Representative images are shown in FIG. 7A and quantification is shown in FIG. 7B. Data (Mean±SD, n=6) are presented as total fluorescence per mg tissue. FIG. 7C: For assessing the uptake of mDNP-FITC by aortic plaque-associated macrophages, Western diet fed LDLR−/− mice were either injected with PBS, or mDNP-FITC or mDNP-LXR-L-FITC. Control animals were injected with PBS alone. Following euthanasia after 24 or 48 h, aortic arch from each mouse was quickly dissected and digested to obtain single cell suspension as described under "Methods". Cells were then stained for CD11b and analyzed by flow cytometry. Mean fluorescent Intensity, a measure of FITC labeled DNP uptake is shown as % Control (Mean±SD, n=4). *P<0.05. FIG. 7D: In a separate experiment, time dependent retention of FITC labeled mDNP-LXLR-L by atherosclerotic plaque-associated macrophages after a single i.v. injection was monitored. Data (Mean±SD, n=3) are shown as % of CD11b+FITC+ cells in the total cells isolated.

FIG. 9A: Plasma total cholesterol (TC) and Triglyceride (TG) levels are shown as mg/dl (Mean±SD, n=6). FIG. 9B: Expression (relative to untreated controls) of indicated genes in liver was determined and data are presented as Mean±SD, n=6.

FIG. 10A: Representative en face images of the aortas. FIG. 10B: Quantification of the area occupied by the plaque (White opaque areas in the images) was performed using Axiovision software and the data are presented as % plaque area (Mean±SD, n=6, both genders). FIG. 10C: Hearts were fixed in buffered formalin, embedded in paraffin and 5 µm sections were stained with H&E. Images were acquired using Carl Zeiss inverted microscope. Representative images of the aortic root showing the plaque development in the aortic valve leaflets (marked by black dashed lines); FIG. 10D: Quantification of the plaque area. Data are expressed as % plaque area per leaflet (Mean±SD, n=6, both genders). *P<0.05

FIG. 11A: Serial sections (5 µm) of the aortic root from paraffin embedded hearts were stained with Trichrome. Images were acquired using Carl Zeiss inverted microscope. Representative images of the aortic root showing the necrotic areas (White blank areas) in the aortic valve leaflets; FIG. 11B: Quantification of the necrotic area. Total plaque was outlined (solid black line) and necrotic white areas were identified using Axiovision software (shown by dotted line) and % necrotic area calculated. Data are expressed as % necrotic area per plaque (Mean±SD, n=9). *P<0.05; FIG. 11C: Specific delivery of LXR ligand by mDNP-LXR-L attenuates expression of pro-inflammatory and NF-kB target gene MMP-9. Serial sections (5 µm) of the aortic root (n=6) were stained for MMP-9 as described under "Methods"; specificity of MMP-9 staining was confirmed by staining the sections in the absence of MMP-9 antibody (labeled—No antibody). Images were acquired using Carl Zeiss inverted microscope under same exposure parameters. Three representative images for each condition are shown. Control—heart sections from mice with no i.v. injections; +mDNP-LXR-L—Heart sections from mice given 4 weekly injections of mDNP-LXR-L.

(FIG. 13A) 300 MHz 1H NMR spectrum of Gal-G5: multiple peaks (2) between 2.2 and 3.4 ppm belong to protons from G5 dendrimer, while single peak (1) at 3.6 ppm belongs to the repeat units of PEG from Gal-PEG-NHS. (FIG. 13B) Agarose gel electrophoresis assay of G5/CEH complex and Gal-G5/CEH complex at different weight ratios; M means DNA ladder, and the complexes (G5/CEH and Gal-G5/CEH) formed in the red bracket. (FIG. 13C) DLS and (FIG. 13D) TEM for Gal-G5 (shown as the red arrows) and Gal-G5/CEH complex (shown in the red circles).

FIG. 14A: Effect of increasing concentration of G5 or Gal-G5 on % viability of hepatocytes is shown as Mean±SD, n=5. *P<0.05. FIG. 14B: Representative Transmittance images are shown; cells marked with Red circles represent detached round dead.

FIG. 15A shows the effects on cellular uptake with increasing concentration and FIG. 15B shown the effects of increasing time of incubation. Quantification of time dependent uptake using 50 nM FITC-G5 or FITC-Gal-G5 was performed by FACS analyses. FIG. 15C: Mean Fluorescence Intensity (MFI) of FITC+ hepatocytes was calculated and data are shown as Mean±SD, n=3. *P<0.05 and **P<0.01. FIG. 15D shows the uptake of two dendrimers by mouse peritoneal macrophage after 6 h incubation.

FIG. 18A: Primary mouse hepatocytes were treated with complexes containing G5/pCMV, G5/CEH, Gal-G5/pCMV or Gal-G5/CEH for 24 h. The spent medium containing complexes was replaced by fresh growth medium and hepatocytes were incubated for additional 24 h and 48 h. At the end of the incubation, total RNA was isolated and CEH gene expression was determined by RT-qPCR as described under "Methods" and data are presented as fold increase compared to cells treated with complexes containing the empty pCMV plasmid (Mean±SD, n=3). *P<0.05 and **P<0.01. FIG. 18B: The flux of FC generated by CEH-mediated hydrolysis of [$^3$H]-HDL-CE to secreted bile acids was assessed by monitoring the appearance of [$^3$H]-bile acids in the culture medium as described under "Methods". Data are presented as % Control (untreated hepatocytes) (Mean±SD, n=3),*P<0.05. FIG. 18C: To monitor the effects of CEH delivery by Gal-G5 on intracellular hydrolysis of HDL delivered CE, primary mouse hepatocytes were first transfected by un-complexed G5 or Gal-G5 or CEH-plasmid complexed with G5 or Gal-G5 for 24 h and hydrolysis of [$^3$H]-HDL-CEs monitored as described under "Methods". Data are presented as % hydrolysis (Mean±SD, n=3),*P<0.05.

FIG. 19A: Organs were harvested at indicated time points and imaged by Odyssey® Fc Imaging System at ex/em=780/800 nm. FIG. 19B: CEH expression in the major organs (heart, liver, spleen, lung and kidney) at 24 h, 48 h and 72 h post-injection was determined by RT-qPCR using total RNA as described under "Methods". Data are presented as Mean±SD, n=3. *P<0.05 and **P<0.01.

(FIG. 22A) These particles comprising both LXR agonist and the siRNA for SR-A were characterized for delivery to macrophages. PEG-yated mDNPs comprising LXR agonist were complexed with siRNA to SR-A (FIG. 22B) Gel retardation assay of mDNP/siRNA complexes at different weight ratios showing that siRNA is fully complexed to mDNP-LXR-L above the ratio of 1:10. (FIG. 22C) Delivery of FITC-labeled siRNA complexed to either non-functionalized DNP or mDNP to macrophages. (FIG. 22D) Quantification of uptake shown in FIG. 22C by Flow Cytometry where fluorescence of FITC conjugated DNP is measured as Mean Fluorescent Intensity. (FIG. 22E) To monitor lysomal escape of siRNA delivered via siRNA/mDNP complexes, following incubation with FITC-labeled siRNA/mDNP complexes, macrophages were fixed and stained for lysosome marker. The co-localization of FITC-labeled siRNA and lysosomal marker is apparent in Merged images.

(FIG. 23A) SR-A mRNA levels were determined by RT-qPCR and significant reduction in SR-A mRNA level was seen in cells exposed to siRNA/mDNP compared to those exposed to complexes containing non-specific scrambled siRNA. (FIG. 23B) Following treatment with siRNA/mDNP complexes, total cellular proteins were analyzed by Western blot analysis using antibody to SR-A. Consistent with the observed changes in mRNA levels shown in FIG. 23A, while no change in SR-A protein levels was noted in cells exposed to scrambled siRNA, cells exposed to SR-A siRNA complexes show a dramatic decrease in SR-A immuno-reactive band. (FIG. 23C) Functional consequence of SR-A siRNA/mDNP mediated reduction in SR-A were assessed by monitoring the uptake of DiI labeled oxLDL. Compared to cells exposed to complexes containing scambled siRNA, reduced uptake of DiI-labeled oxLDL (Red) was seen in cells exposed to complexes containing SR-A siRNA. Cellular lipids were also stained by Oil red O and consistent with reduced uptake of DiI-labeled oxLDL, reduced Oil Red O staining was seen in cells exposed to SR-A siRNA containing complexes.

(FIG. 24A) Macrophages were either left untreated or treated with SR-A siRNA/mDNP or LXR-L-mDNP or SR-A siRNA/LXR-L mDNP complexes and then incubated with AcLDL (50 mg/ml) for 48 h. Following a brief wash with PBS, cells were fixed and stained with Oil Red O. Representative images are shown. (FIG. 24B) Total lipids were extracted from a parallel set of cells and total cholesterol content determined by HPLC and normalized to total cellular protein. Data are presented as nmoles/mg protein (Mean±SD, n=6).

DETAILED DESCRIPTION

Figure 1:
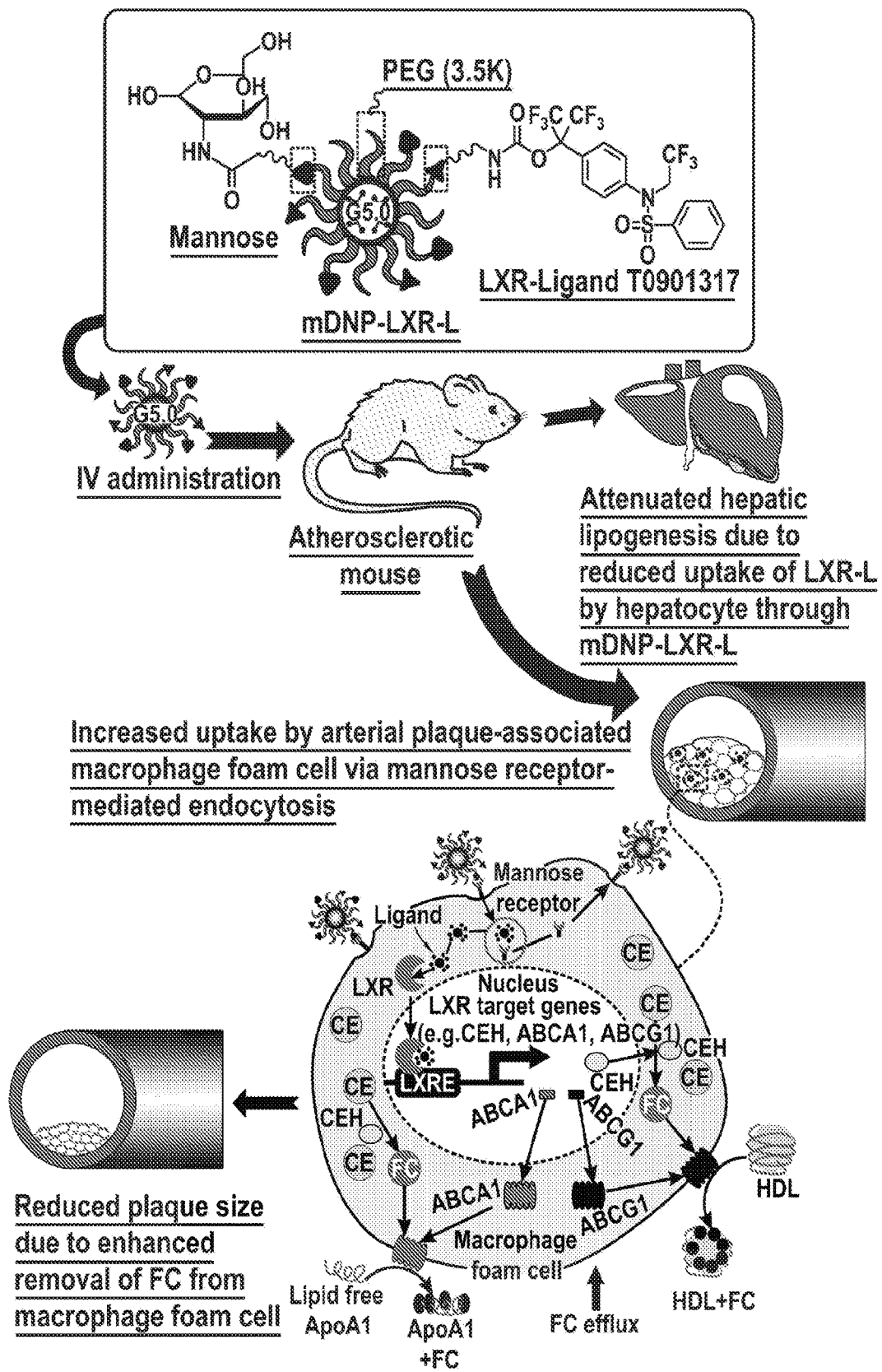
FIG. 1. Schematic of mDNP-LXR-L delivery system for targeting plaque-associated macrophage foam cells via mannose receptor-mediated endocytosis.

Disclosed herein are novel carbohydrate-functionalized nanoparticles for specific delivery of therapeutic payloads. In some embodiments, the inventors found that mannose functionalized dendrimeric nanoparticles (mDNP) can target delivery of a therapeutic compound (for example, a cholesteryl ester (CE) modulator) to plaque-associated macrophages, and eliminate the undesirable lipogenic effects in liver. In addition, the data also show that targeted delivery of liver-x-receptor ligand (LXR-L) to atherosclerotic plaques-associated macrophages results in plaque attenuation and favorable modulation of plaque characteristics. Furthermore, conjugation of the carbohydrate to the dendrimer nanoparticle using extended polyethylene glycol (PEG) linkers prevented agglomeration, decreased the highly positive charge on the surface, and increased the high steric exclusion.

In some embodiments, functionalization of dendrimeric nanoparticles with galactose increased liver-specific delivery, and the use of a long PEG linker for galactose attachment also reduced the toxicity associated with high positive charges on the surface of the unmodified nanoparticle. The development of this non-toxic and efficient liver-specific gene delivery platform can be used for enhancing removal of cholesterol from the body to reduce the existing atherosclerotic plaque burden for which no therapeutics are currently available.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

Terminology

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It is appreciated by those skilled in the art that the design of the expression vector can depend on such factors as the choice of the host cell to be transformed, the level of expression desired, etc.

The term "expression vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The expression vector may be a plasmid, a phage particle, or simply a potential genomic insert. Once transformed into a suitable host, the expression vector may replicate and function independently of the host genome, or may in some instances, integrate into the genome itself. A plasmid is the most commonly used form of expression vector, however, the invention is intended to include such other forms of expression vectors which serve equivalent function as and which are, or become, known in the art.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained.

When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

As used throughout, by a "subject" (or a "host") is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

The term "cholesteryl ester modulator" or "CE modulator" refers to a compound, gene, or expression vector capable of affecting the levels of intracellular cholesteryl esters (CE). Intracellular CE accumulation in macrophages can be reduced by enhancing the removal of unesterified or free cholesterol (FC), a process rate-limited by intracellular CE hydrolysis catalyzed by neutral CE hydrolase (CEH). In some embodiments, the CE modulator decreases the intracellular levels of cholesteryl esters (CE).

Nanoparticles

In some aspects, disclosed herein is a nanoparticle comprising: a polyamidoamine (PAMAM) dendrimer; a carbohydrate moiety, wherein the carbohydrate moiety is linked to the polyamidoamine (PAMAM) dendrimer via a polyethylene glycol (PEG) linker, and wherein the PEG linker comprises at least four individual PEG units; and a therapeutic agent.

In some embodiments, the carbohydrate moiety is mannose. In some embodiments, the carbohydrate moiety is galactose. In some embodiments, the PEG linker comprises PEG (3.5K). In some embodiments, the PEG linker can comprise various molecular weights (for example, about 1.5K, 2K, 3.5K, 5K, 7.5K, 12K, 20K, and 35K g/mol). A "PEG unit" refers to a single—$CH_2CH_2O$— unit within the larger polyethylene glycol (PEG) linker.

The length of the PEG linker/spacer is an important parameter. Initial attempts synthesized and tested the nanoparticles using a small linker. However, the yield was very low, the reaction efficiency was not high, and steric hindrance was problematic. This short linker was abandoned and it was determined that a longer PEG linker was needed. The benefit of the longer linker is to extend out of the moieties from the dendrimer surface to reduce steric hindrance for better targeting, improve cytocompatibility, and extend blood circulation time. The nanoparticles with the longer spacer also produced a significantly higher yield, making possible comprehensive in vitro and in vivo evaluation. The new synthesis methods to prepare the new particles with longer linkers also provided repeated syntheses with a consistent product, allowing the investigation of the structure and activity relationship.

In some embodiments, the therapeutic agent is an intracellular cholesteryl ester (CE) modulator. In some embodiments, the intracellular cholesteryl ester (CE) modulator is an LXR agonist. In some embodiments, the LXR agonist is T0901317 or GW3965. In some embodiments, the LXR agonist is linked to the polyamidoamine (PAMAM) dendrimer via a polyethylene glycol (PEG) linker.

In some embodiments, the intracellular cholesteryl ester (CE) modulator is an expression vector comprising a cholesteryl ester hydrolase (CEH) gene. In some embodiments, the expression vector comprising a cholesteryl ester hydrolase (CEH) gene is encapsulated within the nanoparticle. In some embodiments, the cholesteryl ester hydrolase (CEH) gene is the human macrophage cholesteryl ester hydrolase gene (Accession #AY268104). In some embodiments, the cholesteryl ester hydrolase (CEH) gene comprises the nucleic acid sequence SEQ ID NO:1. In some embodiments, the cholesteryl ester hydrolase (CEH) gene comprises a nucleic acid sequence that is at least 60% identical (for example, at least 60%, at least 65%, at least 70%, at least 75%, at least 80%, at least 85%, at least 90%, at least 95%, at least 99%) to SEQ ID NO:1.

In some embodiments, the cholesteryl ester hydrolase (CEH) gene comprises the nucleic acid sequence SEQ ID NO:2. In some embodiments, the cholesteryl ester hydrolase (CEH) gene comprises a nucleic acid sequence that is at least 60% identical (for example, at least 60%, at least 65%, at least 70%, at least 75%, at least 80%, at least 85%, at least 90%, at least 95%, at least 99%) to SEQ ID NO:2.

In some embodiments, the cholesteryl ester hydrolase (CEH) gene encodes the human macrophage cholesteryl ester hydrolase protein. In some embodiments, the cholesteryl ester hydrolase (CEH) gene encodes for the protein sequence SEQ ID NO:3. In some embodiments the cholesteryl ester hydrolase (CEH) gene encodes for a protein sequence that is at least 60% identical (for example, at least 60%, at least 65%, at least 70%, at least 75%, at least 80%, at least 85%, at least 90%, at least 95%, at least 99%) to SEQ ID NO:3.

The polymeric carriers of the present invention comprise PAMAM (polyamidoamine), a spacer molecule and a carbohydrate moiety, wherein the polymeric structure provides improved properties over previous PAMAM (polyarnidoamine) containing molecules, such as reduced steric hindrance for better targeting, improved cytocompatibility, and/or extended blood circulation time, improving its performance as carrier and delivery vehicles, such as for example in intracellular delivery of isolated deoxyribonucleic acid (DNA) or ribonucleic acid (RNA) sequences, as well as therapeutic drugs, proteins and/or diagnostic probes.

In some embodiments, the polyamidoamine (PAMAM) dendrimer is G0 to G5. In some embodiments, the polyamidoamine (PAMAM) dendrimer is G5 (Tomalia, D. A.; Baker, H.; Dewald, J.; Hall, M.; Kallos, G.; Martin, S.; Roeck, J.; Ryder, J.; Smith, P. A new class of polymers: starburst-dendritic macromolecules. *Polym. J. (Tokyo)* 1985, 17, (1), 117-32).

In some embodiments, the nanoparticle further comprises an siRNA targeting scavenger receptor A (SR-A) or an siRNA targeting CD-36. In some embodiments, the nanoparticle further comprises an siRNA targeting scavenger receptor A (SR-A). In some embodiments, the nanoparticle further comprises an siRNA targeting CD-36.

In some embodiments, the nanoparticle further comprises an siRNA targeting sterol carrier protein 2 (SCP2). Intracellular Sterol carrier protein 2 (SCP2) can modulate the synthesis of CE within the cell. Thus, siRNA or chemical inhibitors can reduce the levels of SCP2.

In some embodiments, disclosed herein is a nanoparticle comprising: a polyamidoamine (PAMAM) dendrimer; a mannose carbohydrate moiety, wherein the mannose carbohydrate moiety is linked to the polyamidoamine (PAMAM) dendrimer via a polyethylene glycol (PEG) linker, and wherein the PEG linker comprises at least four individual PEG units; and a therapeutic agent.

In some embodiments, disclosed herein is a nanoparticle comprising: a polyamidoamine (PAMAM) dendrimer; a mannose carbohydrate moiety, wherein the mannose carbohydrate moiety is linked to the polyamidoamine (PAMAM) dendrimer via a polyethylene glycol (PEG) linker, and wherein the PEG linker comprises at least four individual PEG units; and an intracellular cholesteryl ester (CE) modulator.

In some embodiments, disclosed herein is a nanoparticle comprising: a polyamidoamine (PAMAM) dendrimer; a mannose carbohydrate moiety, wherein the mannose carbohydrate moiety is linked to the polyamidoamine (PAMAM) dendrimer via a polyethylene glycol (PEG) linker, and wherein the PEG linker comprises at least four individual PEG units; and an LXR agonist.

In some embodiments, disclosed herein is a nanoparticle comprising: a polyamidoamine (PAMAM) dendrimer; a mannose carbohydrate moiety, wherein the mannose carbohydrate moiety is linked to the polyamidoamine (PAMAM) dendrimer via a polyethylene glycol (PEG) linker, and wherein the PEG linker comprises at least four individual PEG units; and T0901317.

In some embodiments, disclosed herein is a nanoparticle comprising: a polyamidoamine (PAMAM) dendrimer; a mannose carbohydrate moiety, wherein the mannose carbohydrate moiety is linked to the polyamidoamine (PAMAM) dendrimer via a polyethylene glycol (PEG) linker, and wherein the PEG linker comprises at least four individual PEG units; and or GW3965.

In some embodiments, disclosed herein is a nanoparticle comprising: a polyamidoamine (PAMAM) dendrimer; a galactose carbohydrate moiety, wherein the mannose carbohydrate moiety is linked to the polyamidoamine (PAMAM) dendrimer via a polyethylene glycol (PEG) linker, and wherein the PEG linker comprises at least four individual PEG units; and a therapeutic agent.

In some embodiments, disclosed herein is a nanoparticle comprising: a polyamidoamine (PAMAM) dendrimer; a galactose carbohydrate moiety, wherein the mannose carbohydrate moiety is linked to the polyamidoamine (PAMAM) dendrimer via a polyethylene glycol (PEG) linker, and wherein the PEG linker comprises at least four individual PEG units; and an intracellular cholesteryl ester (CE) modulator.

In some embodiments, disclosed herein is a nanoparticle comprising: a polyamidoamine (PAMAM) dendrimer; a galactose carbohydrate moiety, wherein the mannose carbohydrate moiety is linked to the polyamidoamine (PAMAM) dendrimer via a polyethylene glycol (PEG) linker, and wherein the PEG linker comprises at least four individual PEG units; and an expression vector comprising a cholesteryl ester hydrolase (CEH) gene.

In some embodiments, the galactose is attached to the PAMAM dendrimer using a PEG linker, according to the following PEG-galactose formula:

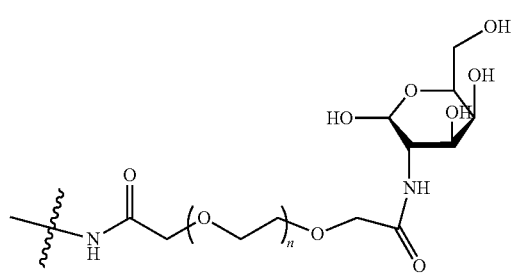

Formula I wherein n≥4.

In some embodiments, the mannose is attached to the PAMAM dendrimer using a PEG linker, according to the following PEG-mannose formula:

Formula II

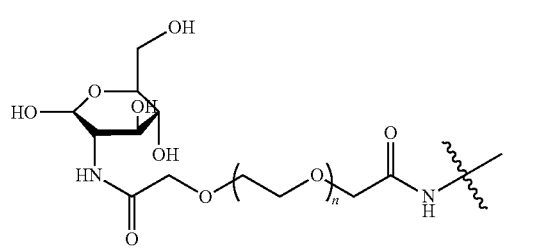

wherein n≥4.

In some embodiments, n≥4. In some embodiments, n can be at least 4, at least 5, at least 6, at least 7, at least 8, at least 9, at least 10, at least 15, at least 20, at least 30, at least 40, at least 50, at least 60, at least 70, at least 80, at least 90, at least 100, or more.

In some embodiments, additional compounds can be attached to the PAMAM dendrimer, including fluorescent compounds (for example, FITC) or additional therapeutic agents. In some embodiments, the compounds and compositions disclosed herein can be administered to a subject in combination with an additional therapeutic agent.

Dendrimers are polymeric structures which can be used as carrier vehicles for the administration of either drugs, proteins, or isolated nucleic acids, associated to therapeutic procedures wherein the administration to a subject or patient of active substances to be distributed to preferred tissues, at a controlled or preferred delivery rate, and protected from metabolic degradation before arrival to their final destination where its action is required, is needed. Structurally, dendrimers are a class of macromolecules at a nanometric scale (less than 1/1,000,000 meters), and therefore they are also known as nanostructures, having multivalent surfaces allowing further modification with functional moieties (—NH$_2$, —COOH, alkyl, etc.), facilitating later the binding of probing molecules for diagnosis or molecular agents for the treatment of diseases.

Patent literature teaches many different approaches for preparing dendrimers which are functionalized for recognizing determined cell types, through conjugation with ligands that can interact with target molecules in specific tissues and/or defined cells (for example, through recognition and binding to surface membrane receptors of said target cells). For example, patent application WO2011053618 teaches new procedures for the synthesis of dendrimers based on PAMAM modified in its ends with multiple hydroxyl groups or ethyleneglycol oligos, which are compatible with further conjugation with functional ligands such as therapeutic agents, drugs, probes. etc.

PAMAM dendrimers are generally in a size ranging from 25 nm a 10 μm (10,000 nm) (see WO2011123591) and can be used to conjugate—and thus bind and transport—therapeutic or diagnostic molecules which are to be distributed with the PAMAM dendrimer. Among the applications in medicine which have been published using dendrimers, PAMAM dendrimers have been used for the transport of therapeutic agents (WO2010054321).

Methods

In some aspects, disclosed herein is a method of treating cardiovascular disease, comprising: administering to a subject in need thereof a nanoparticle comprising: a polyamidoamine (PAMAM) dendrimer; a carbohydrate moiety, wherein the carbohydrate moiety is linked to the polyamidoamine (PAMAM) dendrimer via a polyethylene glycol (PEG) linker, and wherein the PEG linker comprises at least four individual PEG units; and a therapeutic agent.

In some embodiments, the carbohydrate moiety is mannose. In some embodiments, the carbohydrate moiety is galactose. In some embodiments, the PEG linker comprises PEG (3.5K).

In some embodiments, the therapeutic agent is an intracellular cholesteryl ester (CE) modulator. In some embodiments, the intracellular cholesteryl ester (CE) modulator is an LXR agonist. In some embodiments, the LXR agonist is T0901317 or GW3965. In some embodiments, the LXR agonist is linked to the polyamidoamine (PAMAM) dendrimer via a polyethylene glycol (PEG) linker. In some embodiments, the intracellular cholesteryl ester (CE) modulator is an expression vector comprising a cholesteryl ester hydrolase (CEH) gene. In some embodiments, the expression vector comprising a cholesteryl ester hydrolase (CEH) gene is encapsulated within the nanoparticle.

In some embodiments, the nanoparticle further comprises an siRNA targeting scavenger receptor A (SR-A) or an siRNA targeting CD-36. In some embodiments, the nanoparticle further comprises an siRNA targeting scavenger receptor A (SR-A). In some embodiments, the nanoparticle further comprises an siRNA targeting CD-36. In some embodiments, the nanoparticle further comprises an siRNA targeting sterol carrier protein 2 (SCP2).

In some embodiments, the cardiovascular disease is atherosclerosis. Atherosclerosis is the underlying cause of myocardial infarction (heart attack) and stroke. These agents by virtue of either reducing the plaque burden per se or changing plaque characteristics can reduce the risk of plaque rupture that underlies heart attack and stroke. In addition, reducing the plaque burden can improve blood flow/perfusion. In some embodiments, the cardiovascular disease is myocardial infarction (heart attack). In some embodiments, the cardiovascular disease is stroke.

In some aspects, disclosed herein is a method of treating cardiovascular disease, comprising: administering to a subject in need thereof a nanoparticle comprising: a polyamidoamine (PAMAM) dendrimer; a carbohydrate moiety, wherein the carbohydrate moiety is linked to the polyamidoamine (PAMAM) dendrimer via a polyethylene glycol (PEG) linker, and wherein the PEG linker comprises at least four individual PEG units; and a therapeutically effective amount of a therapeutic agent.

In some aspects, disclosed herein is a method for delivery of a therapeutic agent to a plaque-associated macrophage, comprising: administering to a subject a nanoparticle comprising: a polyamidoamine (PAMAM) dendrimer; a carbohydrate moiety, wherein the carbohydrate moiety is linked to the polyamidoamine (PAMAM) dendrimer via a polyethylene glycol (PEG) linker, and wherein the PEG linker comprises at least four individual PEG units; and a therapeutic agent; wherein the therapeutic agent is delivered to a plaque-associated macrophage.

In some embodiments, the carbohydrate moiety is mannose. In some embodiments, the PEG linker comprises PEG (3.5K).

In some embodiments, the therapeutic agent is an intracellular cholesteryl ester (CE) modulator. In some embodiments, the intracellular cholesteryl ester (CE) modulator is an LXR agonist. In some embodiments, the LXR agonist is T0901317 or GW3965. In some embodiments, the LXR agonist is linked to the polyamidoamine (PAMAM) dendrimer via a polyethylene glycol (PEG) linker. In some embodiments, the intracellular cholesteryl ester (CE) modulator is an expression vector comprising a cholesteryl ester hydrolase (CEH) gene. In some embodiments, the expression vector comprising a cholesteryl ester hydrolase (CEH) gene is encapsulated within the nanoparticle. In some embodiments, the nanoparticle further comprises an siRNA targeting scavenger receptor A (SR-A) or an siRNA targeting CD-36. In some embodiments, the nanoparticle further comprises an siRNA targeting scavenger receptor A (SR-A). In some embodiments, the nanoparticle further comprises an siRNA targeting CD-36. In some embodiments, the nanoparticle further comprises an siRNA targeting sterol carrier protein 2 (SCP2).

In some embodiments, the administration of the nanoparticles disclosed herein result in plaque attenuation and/or favorable modulation of plaque characteristics.

In another aspect, disclosed herein is a method for delivery of a therapeutic agent to a hepatocyte, comprising: administering to a subject a nanoparticle comprising: a polyamidoamine (PAMAM) dendrimer; a carbohydrate moiety, wherein the carbohydrate moiety is linked to the polyamidoamine (PAMAM) dendrimer via a polyethylene glycol (PEG) linker, and wherein the PEG linker comprises at least four individual PEG units; and a therapeutic agent; wherein the therapeutic agent is delivered to a hepatocyte.

In some embodiments, the carbohydrate moiety is galactose. In some embodiments, the PEG linker comprises PEG (35K).

In some embodiments, the therapeutic agent is an intracellular cholesteryl ester (CE) modulator. In some embodiments, the intracellular cholesteryl ester (CE) modulator is an expression vector comprising a cholesteryl ester hydrolase (CEH) gene. In some embodiments, the expression vector comprising a cholesteryl ester hydrolase (CEH) gene is encapsulated within the nanoparticle.

EXAMPLES

The following examples are set forth below to illustrate the compositions, nanoparticles, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Development of Mannose Functionalized Dendrimeric Nanoparticles for Targeted Delivery to Macrophages and Use of this Platform to Modulate Atherosclerosis Dysfunctional macrophages underlie the development of several diseases including atherosclerosis where accumulation of cholesteryl esters (CE) and persistent inflammation are two of the critical macrophage processes that regulate the progression as well as stability of atherosclerotic plaques. Ligand dependent activation of liver-x-receptor (LXR) not only enhances mobilization of stored CE but also exerts anti-inflammatory effects mediated via trans-repression of pro-inflammatory transcription factor NF-κB. However, increased hepatic lipogenesis by systemic administration of LXR ligands has precluded their therapeutic use. The objective of the present example was to devise a strategy to selectively deliver LXR ligand (LXR-L) to atherosclerotic plaque-associated macrophages while limiting hepatic uptake. Mannose-functionalized dendrimeric nanoparticles (mDNP) were synthesized to facilitate active uptake via the mannose receptor expressed exclusively by macrophages using polyamidoamine (PAMAM) dendrimer. Terminal amine groups were utilized to conjugate mannose and LXR ligand (LXR-L) T091317 via polyethylene glycol (PEG) spacers. mDNP-LXR-L was effectively taken up by macrophages (and not by hepatocytes), increased expression of LXR target genes (ABCA1/ABCG1) and enhanced cholesterol efflux. When administered intravenously to LDLR−/− mice with established plaques, significant accumulation of fluorescently labeled mDNP-LXR-L was seen in atherosclerotic plaque-associated macrophages. Four weekly injections of mDNP-LXR-L led to significant reduction in atherosclerotic plaque progression, plaque necrosis and plaque inflammation as assessed by expression of NF-κB target gene MMP-9; no increase in hepatic lipogenic genes or plasma lipids was observed. These studies in this example validate the development of a macrophage-specific delivery platform for the delivery of anti-atherosclerotic agents directly to the plaque-associated macrophages to attenuate plaque burden.

Background

Macrophages are effector cells that not only play a major role in innate and adaptive immunity, but also play an important role in tissue repair and homeostasis. However, normal physiological functions of macrophages are perturbed in several diseases including metabolic diseases such as atherosclerosis, diabetes and obesity. Therefore, targeting the recruitment, activation and/or regulation of dysfunctional macrophages represents a promising therapeutic strategy. With the advancement of nanotechnology, development of nanomedicines to efficiently target dysfunctional macrophages can strengthen the effectiveness of therapeutics and improve clinical outcomes[1]. Several macrophage specific surface receptors have been described including mannose receptor[2], folate receptor[3] and TIM-4 or BAI-1[4,5] that can potentially be utilized for effective targeting. While folate-functionalized nanomedicine to target cancerous tissue-associated macrophages has been described[6], current strategies to target dysfunctional macrophages in other chronic diseases such as atherosclerosis are very limited.

Amongst the vast repertoire of nanomedicine options, polyamidoamine (PAMAM) dendrimers offer several distinct advantages for the development of multifunctional dendrimeric nanoparticles (DNP). More than 120 terminal amine groups on PAMAM dendrimer generation 5.0 permit accessible surface modifications and also offer high buffering capacity for the unique "proton-sponge" effect desirable for endosomal escape. Furthermore, PEGylation of DNP prevents agglomeration, decreases the highly positive charge on the surface and increases the high steric exclusion, thus extending the circulation time in the blood[7-9]. Several PAMAM-derived nanoparticles were developed and were shown to enhance delivery of drugs[10] as well as for gene delivery[11]. Furthermore, functionalized PAMAM dendrimer-triglycine-EGF nanoparticles were demonstrated to successfully deliver drugs and/or nucleic acids via specific receptor binding[12]. Thus, PAMAM based DNP can be used to develop nanomedicines to target dysfunctional macrophages.

Atherosclerosis is one of the many metabolic diseases where dysfunctional macrophages play a causal role and are involved in all stages of its development. The two main and causally related characteristics of the dysfunctional macrophages in atherosclerosis are accumulation of cholesteryl esters (CE) and inability to appropriately resolve inflammation.[13, 14] Intracellular CE accumulation in macrophages can be reduced by enhancing the removal of unesterified or free cholesterol (FC), a process rate-limited by intracellular CE hydrolysis catalyzed by neutral CE hydrolase (CEH)[15, 16] and earlier studies from our laboratory have demonstrated CEH overexpression-mediated increase in CE mobilization[17-19]. FC generated by CEH mediated hydrolysis of CE becomes available for ApoA1 or HDL-dependent efflux through fc transporters abca1/g1[20] and carried to the liver for final elimination from the body. While over-expression of ABCA1 attenuate atherosclerosis[21, 22], deficiency of ABCA1 in macrophages enhances plaque progression[23]. Therefore, a strategy to enhance FC removal from dysfunctional macrophage foam cells by simultaneously increasing CEH activity[24] and ABCA1/G1 expression[25] is likely to attenuate foam cell formation. Activation of liver-X-receptor (LXR) is one such strategy. LXR activation in macrophages is athero-protective[25, 26] and the underlying mechanism is thought to be increased expression of ABCA1/G1 resulting in increased FC efflux from macrophage foam cells. Functional LXR response elements are also present in the proximal CEH promoter and LXR ligands increase CEH promoter activity[27]. Therefore, targeted delivery of LXR ligand to macrophages potentially increases FC efflux by modulating two critical intracellular mechanisms. Ligand mediated activation of LXR also suppresses inflammation via transrepression of NF-κB mediated inflammatory pathways[28]. Consistently, administration of an LXR agonist results in attenuation of atherosclerosis in LDLR−/− and ApoE−/−[29] mice and macrophage LXR are considered as endogenous inhibitors of atherosclerosis[30]. Despite these promising effects, use of LXR ligands in clinical arena is hindered by the observed hepatic steatosis (>6 fold increase in liver triglycerides) and hypertriglyceridemia (>2-fold increase) due to activation of hepatic LXR[31]. In the liver, LXR acts as a master lipogenic transcription factor to directly regulate fatty acid synthase (FAS) and sterol regulatory element-binding protein 1 (SREBP1, a pro-lipogenic transcription factor) thus enhancing lipogenesis[32]. Hence, to maximize the efficacy of LXR ligands in treatment of atherosclerosis, it is essential to devise a strategy to selectively deliver LXR ligand to atherosclerotic plaque-associated macrophages while limiting its hepatocyte uptake.

The present example was therefore undertaken to develop such a functionalized DNP-based platform for specific delivery of payloads to macrophages. Advantage was taken of the specific surface expression of mannose receptor on macrophages to develop mannose functionalized DNP (mDNP) for targeted delivery of LXR ligand (LXR-L) to macrophages. Data presented herein demonstrate the use of mDNP for specific delivery of LXR-L to macrophages and not hepatocytes, thereby eliminating the undesirable lipogenic effects in liver. Furthermore, the data also show that targeted delivery of LXR-L to atherosclerotic plaques-associated macrophages results in LXR-L dependent plaque attenuation and favorable modulation of plaque characteristics.

Materials and Methods
Materials

Ethylenediamine (EDA) core polyamidoamine (PAMAM) dendrimer generation 5.0 (technical grade) was purchased from Dendritech (Midland, Mich.). Fluorescein isothiocyanate (FITC), 4-nitrophenyl chloroformate (NPC), triethylamine (TEA), COOH-PEG-NH$_2$ (M$_n$=3500 g/mol), tetrahydrofuran (THF), 1-ethyl-3-(-3-dimethylaminopropyl) carbodiimide hydrochloride (EDC), and LXR ligand T0901317 were purchased from Sigma-Aldrich® (St. Louis, Mo.). Mannose-PEG-NHS (M$_n$=3500 g/moL) was custom synthesized by JenKem® Technology (Plano, Tex., USA). 800CW-NHS ester was obtained from Li-COR® Biotechnology (Lincoln, Nebr.). SnakeSkin™ dialysis tubing with 3500 molecular weight cut-off (MWCO) was purchased from Thermo Scientific™ (Rockford, Ill.). William's E medium, DMEM medium, fetal bovine serum (FBS) and Dulbecco's Phosphate-buffered saline (DPBS) were obtained from Gibco™ BRL (Carlsbad, Calif., USA). Trypsin-EDTA (0.25%), streptomycin and penicillin were obtained from Invitrogen Co., USA. VECTASHIELD® mounting media were purchased from Vector® Laboratories (Burlingame, Calif.). RNeasy® Mini Kit was purchased from QIAGEN. High Capacity cDNA Reverse Transcription Kit and TaqMan™ Universal PCR Master Mix, no AmpErase™ UNG were obtained from Applied Biosystems™. All other chemicals were purchased from Sigma-Aldrich® (St. Louis, Mo.).

Synthesis and Characterization of Functionalized DNP

The overall synthesis scheme is shown in FIG. 1A. In brief, 5 mg of LXR-L (10 mg/mL in DMSO as stock solution) and COOH-PEG-NH$_2$ (the molar ratio of PEG to LXR-L was 1:1.05) were mixed in 10 mL of THF and stirred overnight with NPC (the molar ratio of PEG to NPC was 1:1.5) and excess TEA. The reaction product was filtered and the solvent was evaporated. The obtained residue was dissolved in water, subjected to dialysis with 3000 MWCO overnight and then lyophilized to obtain COOH-PEG-LXR-L. COOH-PEG-LXR-L was coupled to the amino groups on the surface of PAMAM dendrimer G5.0 in DMSO via EDC/NHS reaction. Following an overnight incubation, the solvent was dialyzed by water to remove the DMSO and lyophilized to obtain DNP-LXR-L. The DNP-LXR-L was dissolved in 0.1 M sodium bicarbonate solution and Mannose-PEG-NHS was added (the molar ratio of Mannose-PEG-NHS to G5 was approximately 10:1). The resulting mixture was stirred overnight at room temperature followed by sufficient dialysis with 3000 MWCO and lyophilization to get the final product mDNP-LXR-L. To facilitate monitoring of intracellular uptake and trafficking, FITC was coupled to mDNP-LXR-L or G5 as described earlier[37]. To monitor the specific targeting to macrophages in atherosclerotic plaques, NIR dye 800CW-NHS ester was coupled to the mDNP-LXR-L based on the procedure described before[38]. $^1$H NMR spectra were recorded on a Varian superconducting Fourier-transform NMR spectrometer (Mercury-300)[39]. D$_2$O was used as the solvent. The proton chemical shift of D$_2$O is 4.8 ppm. The particles used in this study were DNP (PAMAM G5.0), mDNP (mannose functionalized DNP), and mDNP-LXR-L (mannose functionalized DNP conjugated to LXR ligand T0901317). Particle size and zeta potential information was obtained by using a Malvern Zetasizer Nano ZS90 apparatus (Malvern Instruments, Worcestershire, U.K.). Changes in the size and zeta potential of mDNP-LXR-L were also monitored during 24 h incubation at 37° C. in order to test its colloidal stability after resuspension in DPBS.

In Vitro Validation
Cell Culture

Thioglycollate-elicited mouse peritoneal macrophages (MPMs) were harvested and non-adherent cells were removed after 4 h and medium replaced with fresh growth medium (10% FBS containing DMEM medium) 24. Primary mouse hepatocytes were prepared as described earlier[40]. Cells (0.7×10$^6$ cells/well) were plated in collagen coated 6-well plates and the growth medium (William's E medium without Phenol red containing hepatocyte thawing as well as plating supplement from Invitrogen) was changed after 3 h. After 24 h, medium was replaced with fresh medium.

Mannose Receptor Expression

The mannose receptor expression was examined in macrophages or hepatocytes by western blot analyses. Briefly, cells were washed twice with ice-cold DPBS, and then lysed by incubating in the RIPA buffer supplemented with protease and phosphatase inhibitor cocktail (Sigma-Aldrich®, St. Louis, Mo.) for 30 min at 4° C. The proteins (~30 µg) were separated by 10% SDS-PAGE (Bio-Rad Laboratories), transferred to polyvinylidene difluoride membrane, immunoblotted with 1:200 diluted anti-mannose receptor rabbit polyclonal antibody (ab64693, Abcam, Cambridge Mass.) and followed by Goat anti-rabbit antibody conjugated to IRDye™ 800 CW (green). Positive immunoreactivity was detected using the Odyssey® CLx imaging system. The membrane was stripped and re-probed for actin using mouse monoclonal antibody (sc-47778, Santa Cruz biotechnology) and goat anti mouse secondary antibody conjugated to IRDye® 680CW (red).

Evaluation of Cell Viability Following mDNP-LXR-L Uptake

Freshly isolated MPMs (0.8×10$^6$ cells/well) or mouse hepatocytes (0.3×10$^6$ cells/well) were plated in 48 well plates and growth medium was changed after 4 h. After 24 h, the growth medium was replaced with fresh medium containing increasing concentrations of mDNP-LXR-L and incubated for additional 24 h. Cell viability was determined using WST-1 assay.

Cellular Uptake of mDNP by Macrophages or Hepatocytes

For imaging of mDNP uptake, cells were plated in 2-well chamber slides. At the end of each treatment, cells were washed with DPBS, fixed with 4% formaldehyde at room temperature for 20 min, permeabilized with 0.1% Triton X-100® for 5 min, and the cell nuclei were counterstained with DAPI for 5 min. Cellular uptake was assessed by fluorescent imaging, a 405 nm laser line was selected for DAPI, and a 488 nm laser line was selected for FITC. For quantification of uptake, cells were harvested at the end of the incubation, analyzed by flow cytometry and uptake of mDNP was expressed as Mean fluorescence intensity. To evaluate the specificity of mDNP uptake by macrophages, MPMs were pre-treated with 0.1 mM Mannan (mannose receptor antagonist) for 30 minutes prior to the addition of 0.2 µM mDNP-FITC.

CEH Activity

Intracellular CEH activity was measured by monitoring the hydrolysis of cholesteryl [1-$^{14}$C] oleate (NEN). The substrate was presented as micelles and was prepared as described by Hajjar et al[41]. In a standard assay, 25 µL of this substrate was used in a final volume of 500 µL giving the final concentration of 6 µM cholesteryl oleate, 23.7 µM phosphatidyl choline and 12.5 µM sodium taurocholate. CE hydrolytic activity was measured using three different protein concentrations to ensure linearity and each assay was performed in duplicate. The activity is expressed as nmoles of [1-$^{14}$C] oleate released/h/mg protein[42].

FC Efflux Assays

Freshly isolated MPMs (1×10$^6$ cells/well) were plated in 24-well culture plates and incubated overnight. The intracellular FC and CE pools were labeled with [$^3$H]-cholesterol by incubating the cells for 48 h with serum-free medium containing 1 µCi/mL [$^3$H]-cholesterol (Perkin Elmer) and 25 µg/mL acetylated LDL (Kalen Biomedical, Inc). The cells were then washed and incubated with serum-free medium for 24 h to allow all pools of cholesterol to equilibrate. Following equilibration, FC efflux was initiated by replacing the medium with growth medium containing 10% FBS and % FC efflux was evaluated as described earlier[18].

In Vivo Validation

All animal procedures were approved by the Institutional Animal Care and Use Committee of Virginia Commonwealth University. LDL receptor knockout mice (LDLR−/−) originally obtained from Jackson Laboratory and maintained in the laboratory in a barrier facility were used for all studies. At 10 weeks of age mice of both genders were fed a high fat, high cholesterol Western type diet (WD, TD88137, Harlan Teklad) which contained 21% fat, 0.15% cholesterol, and 19.5% casein by weight with no sodium cholate for 12 weeks. After 12 weeks, mice were switched to chow diet. The experimental group was injected (i.v., weekly for 4 weeks) with mDNP-LXR-L (200 µg in 100 µL DPBS) and the control group did not receive any injections. It should be noted that strong in vitro and in vivo data demonstrating no effects of mDNP in modulating LXR target gene expression in macrophages and/or liver precluded the necessity to inject control mice with mDNP alone. Following an overnight fast, mice were euthanized (by inhalation of Isofluorane) to collect blood, aorta and heart for analyses.

Uptake of mDNP by Atherosclerotic Plaque-Associated Macrophages

To image the uptake of mDNP by atherosclerotic plaque-associated macrophages in vivo, NIR-mDNP (labeled with 800CW) were injected (i.v., 0.25 mg 800CW/kg, 3 mice per group) into LDLR−/− mice with established atherosclerotic lesions as a result of WD feeding for 16-weeks. For ex vivo imaging, the major organs (heart, liver, spleen, lung and kidney as well as entire aorta) were harvested after 24 hours and imaged using Odyssey® Fc Imaging System (LI-COR, Nebraska, USA) at ex/em=780/800 nm.

In order to quantify the uptake by the macrophages associated with the aortic lesions, mDNP-FITC was injected into 16-week-old atherosclerotic mice (0.5 mg FITC/kg, 3 mice per group). Aortic arch was dissected, cleaned and digested as described by Galkina et al[43] and used in our laboratory[44]. Isolated cells were re-suspended in FACS buffer containing Fc block and incubated with fluorescently labeled anti-CD45 antibody (CD45-PE, eBioscience) and anti-CD11b antibody (CD11b-AlexaFluor® 700, eBioscience) for 20 min at 4° C. After washing, specific immunofluorescent staining of individual cells in the total cell suspension was detected by flow cytometry (BD Biosciences, Canto II) and the data were analyzed using FlowJO™ software (Tree Star Inc.). Uptake of mDNP-FITC was quantified by determining the mean fluorescent intensity of FITC in CD11b+ macrophages in the CD45+ population. To evaluate retention of CD11b+FITC+ cells in the atherosclerotic plaques following a single injection, data was expressed as % CD11b+FITC+ cells at given time.

Expression of LXR-Target Genes

Total RNA (from MPMs, hepatocytes or liver) was extracted with RNeasy™ Mini Kit (Qiagen, Valencia Calif.). Five microgram of total RNA was reverse transcribed with Thermoscript™ RT-PCR System (Invitrogen) and first strand cDNA was used to perform Real Time PCR using Stratagene Mx3000p real time PCR system with TaqMan™ Gene Expression Assays for ABCA1 (Mm00442646_m1), ABCG1 (Mm00437390_m1), FAS (Mm00662319_m1) and SREBP1 (Mm00550338_m1) (Applied Biosystems, Foster City, Calif.).

Plasma Analyses

Total plasma cholesterol and triglycerides were determined using the Cobas c311 automated chemistry analyzer with reagents, calibrators, and controls from Roche Diagnostics.

Quantitative Atherosclerosis Analyses

The aorta was dissected from the heart to the iliac bifurcation, cleaned of any surrounding tissue, opened longitudinally, pinned on black wax and fixed for 24 h in 10% buffered formalin. The fixed aortas were imaged on a black background using a Canon Digital Camera fitted with a 60 mm, f/2.8 Macro Lens. Total area and the area occupied by the lesions in the aortic arch as well as total aorta was determined using Axiovision Image Analysis software (Carl Zeiss)[24].

Morphological Analyses of the Lesions

Hearts were fixed in buffered formalin, paraffin embedded and sectioned. Once the aortic sinus was visible, serial sections (5 μm thick) were transferred to numbered slides. Serially numbered slides were then stained with Masson's Trichrome stain and Heamatoxylin/Eosin (H&E). Images were acquired with Zeiss Observer A1 inverted microscope and analyzed by Axiovision Image Analysis Software to quantify the total lesion or % necrotic area[24].

Immunohistochemistry

Heart sections (two per slide) with visible aortic root were dewaxed using CitraSolv and rehydrated using serial incubations in 100, 95 and 70% ethanol followed by deionized water. Following antigen retrieval in pre-heated citrate buffer (10 mM Sodium Citrate, 0.05% Tween® 20, pH 6.0, 95° C.), the sections were incubated with 5% horse serum (Blocking solution) to block non-specific sites. The sections were subsequently incubated overnight with either primary antibody (Negative Control) or anti-MMP-9 antibody (sc-6840, goat polyclonal antibody, 1:50 dilution in blocking solution). Following three washes in PBS, sections were then incubated with biotin conjugated horse anti-goat IgG for 1 h followed by NeutrAvidin™ conjugated Alexa Flour™546 as the fluorescent detection reagent. Coverslips were mounted using ProLong™ Diamond antifade mountant with DAPI (Molecular Probes). Images were acquired using a Zeiss inverted microscope fitted with a digital camera in a Multi-Tritacquisition mode using pseudo-coloring.

Statistical Analysis

All data were analyzed using GraphPad Prism software. Statistical significance of difference between groups was determined ANOVA and Tukey's multiple comparison tests were performed to evaluate the significant difference between groups, if applicable. P<0.05 was considered statistically significant.

Results

Synthesis and Characterization of mDNP-LXR-L

Figure 2A:
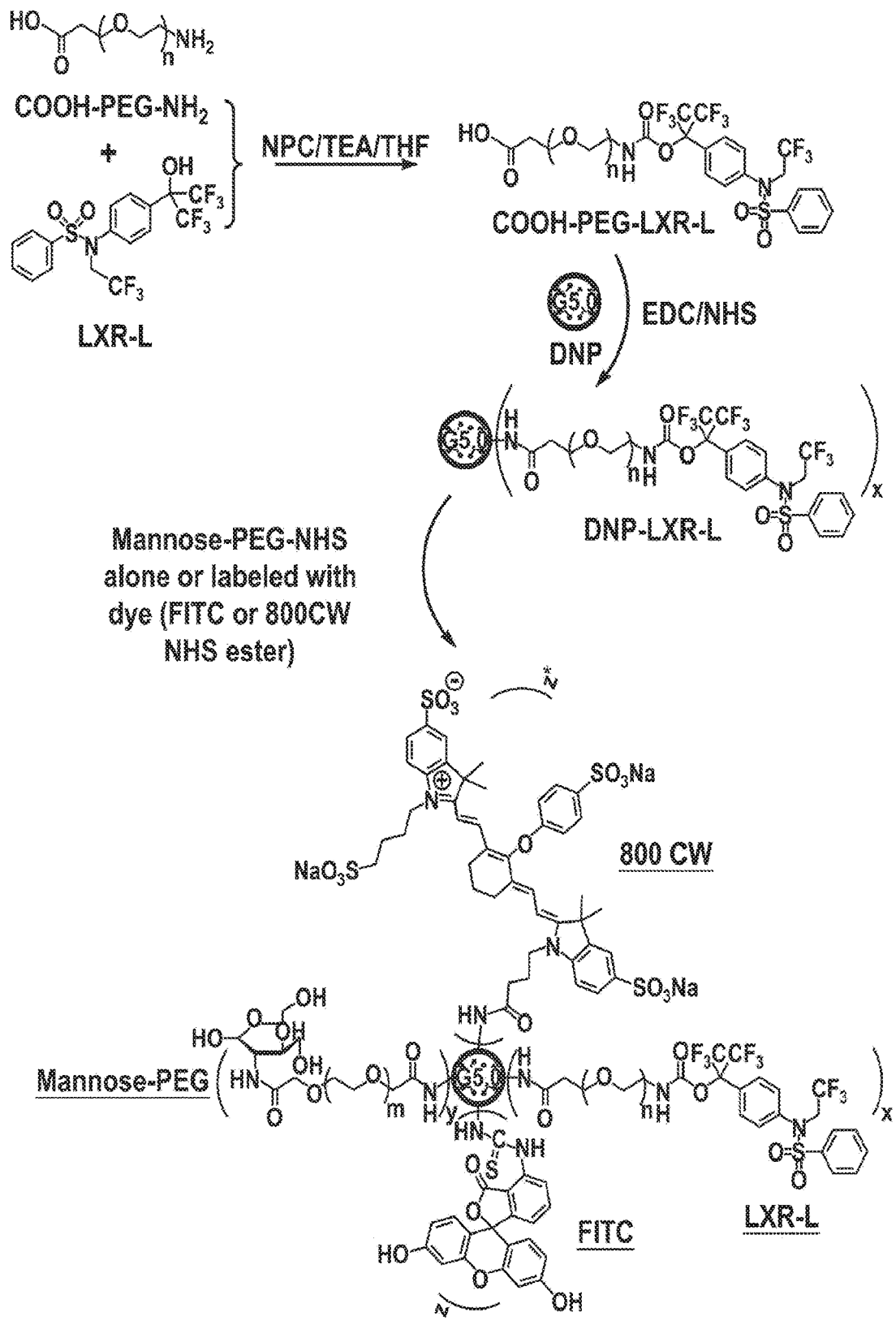
FIG. 2A-2F. Synthesis and characterization of mDNP-LXR-L.
Figure 2B:
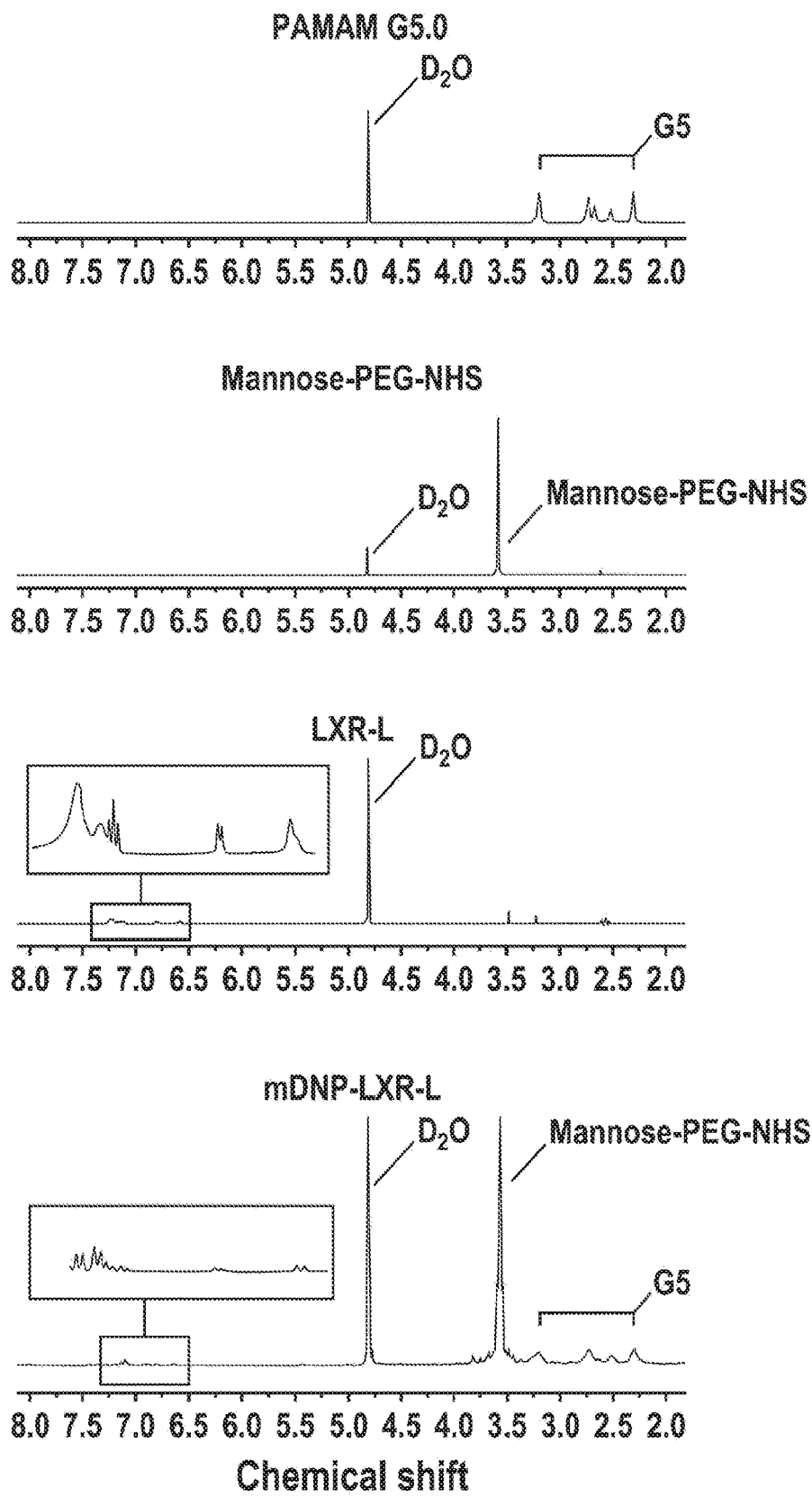
Figure 2C:
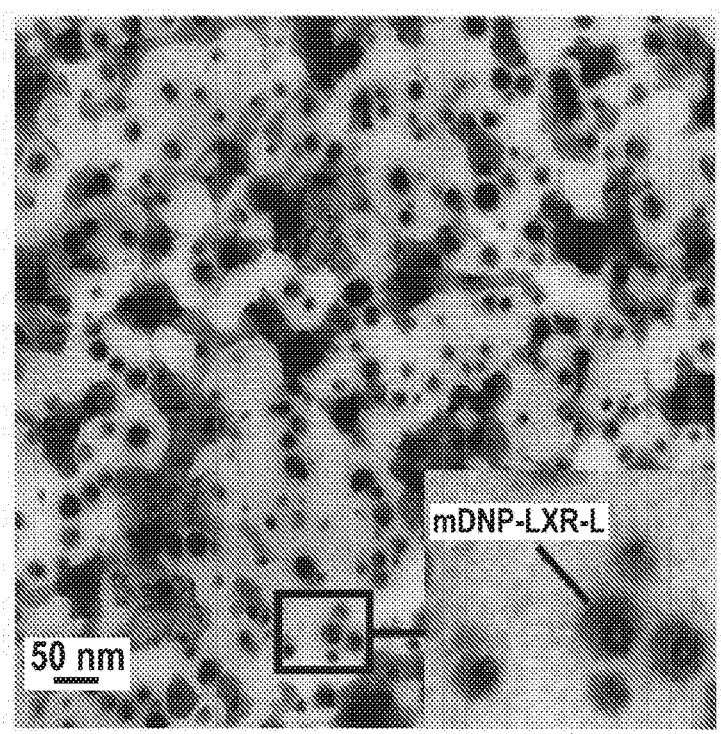
Figure 2D:
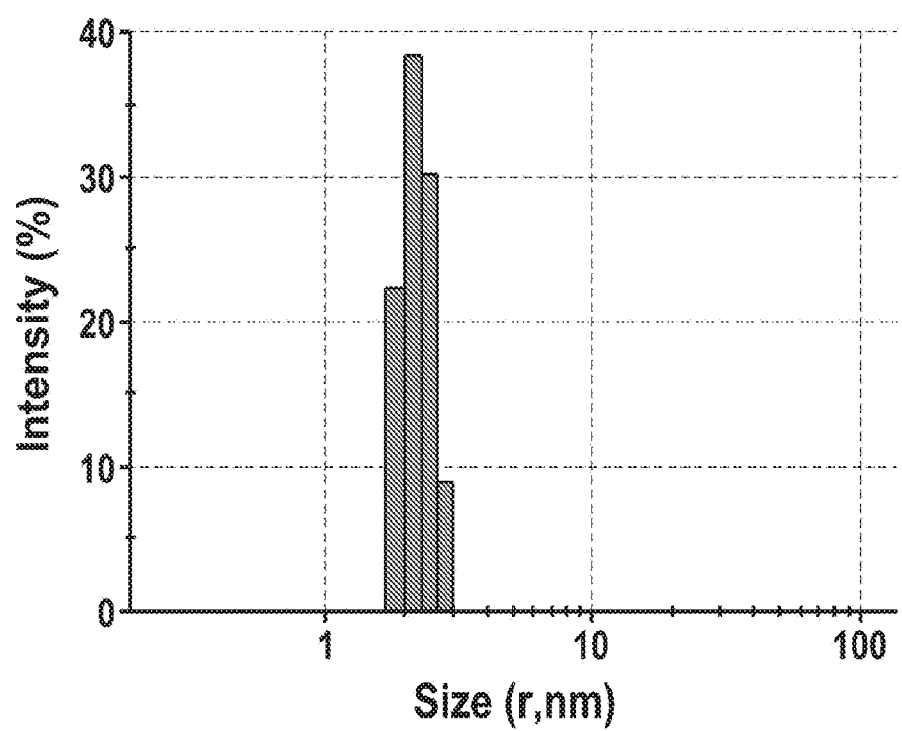
Figure 2E:
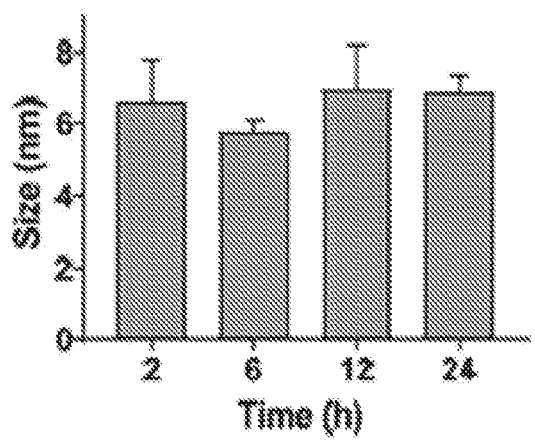
Figure 2F:
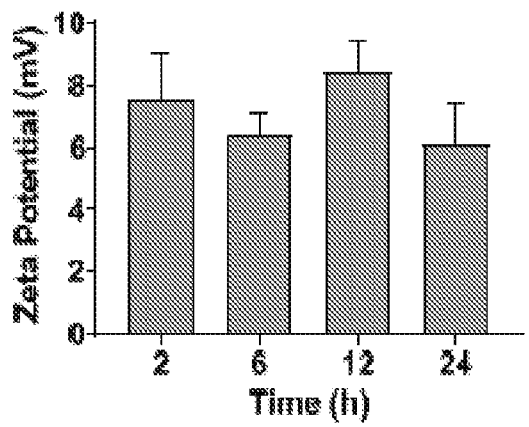

FIG. 2A details the steps involved in the synthesis of mDNP-LXR-L utilizing PAMAM dendrimer G5.0 as a polymeric core, LXR-L T0901317 as the model drug and mannose-PEG-NHS as a targeting ligand. PEG spacer between LXR-L and PAMAM G5.0 as well as mannose and PAMAM G5.0 were added to accomplish longer resident time in circulation. Following the synthesis, the final product mDNP-LXR-L was purified by sufficient dialysis and characterized for its physiochemical properties. $^1$H NMR spectrum (FIG. 2B) shows that the final product has relatively high purity without interfering proton peaks from the reactants, intermediates, or reaction solvent. The methylene protons of branching units within the dendrimer have multiple peaks between 2.2 and 3.4 ppm. The methylene protons of repeat units from Mannose-PEG and PEG-LXR-L have a singlet peak at 3.6 ppm. The proton peaks between 6.5 and 7 ppm are attributed to the benzene ring protons of LXR-L. Based on the integrals of the proton peaks, the stoichiometric ratio for PEG-LXR-L:PEG-Mannose-NHS:G5.0 was approximately 5:10:1. The particles had a relatively uniform size as seen in FIG. 2C. The surface functionalization chemistry did not noticeably change the size of dendrimeric nanoparticles. The mean hydrodynamic size of mDNP-LXR-L was ~5 nm with a narrow polydispersity (FIG. 2D), consistent with the reported value of commercially available PAMAM dendrimer G5.0. The zeta potential of mDNP-LXR-L decreased from ~30 mV (unmodified PAMAM dendrimer G5.0) to ~6 mV (Zero time point, data not shown) and did not change over time (FIG. 2E) suggesting that the PEGylation significantly shielded the positively charged dendrimer surface. Colloidal stability tests also showed that mDNP-LXR-L had excellent stability with no obvious change in size (FIG. 2F) over the 24 h time period tested.

In Vitro Validation

Evaluation of Cellular Toxicity

Figure 3A:
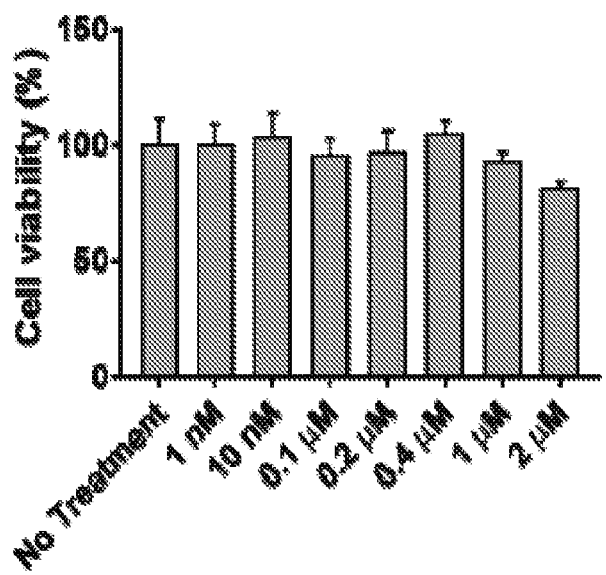
FIG. 3A-3B. mDNP-LXR-L does not affect cell viability.
Figure 3B:
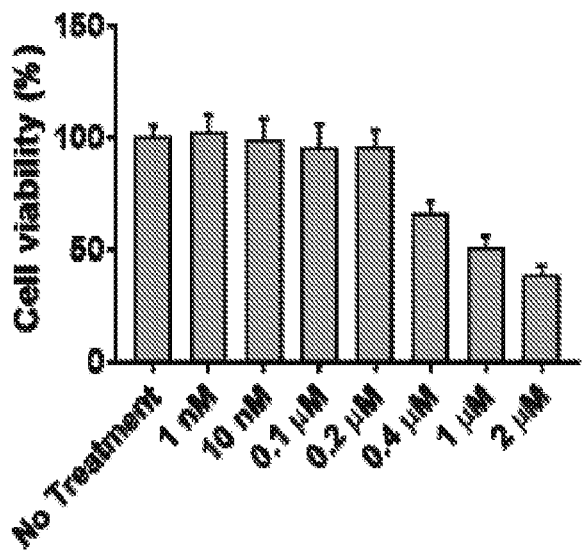

Mouse hepatocytes or mouse peritoneal macrophages (MPMs) were exposed to increasing concentrations of mDNP-LXR-L and cell viability was evaluated. As shown in FIG. 3A, no significant decrease in cell viability was noted in MPMs even when exposed to a concentration of 2 μM. However, a decrease in cell viability was noted when hepatocytes (FIG. 3B) were exposed to concentrations above 0.2 μM.

Specificity of Uptake by Macrophages

Figure 4A:
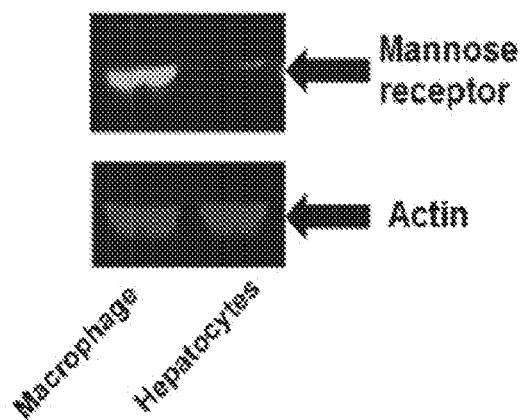
FIG. 4A-4C. Specific uptake of mDNP-FITC by macrophages.

Activation of LXR in hepatocytes leads to undesirable increase in lipogenic target genes[31] leading to increased hepatic lipid accumulation and the foremost objective of the present study was to develop a platform with specific delivery to macrophages and yet limited the uptake by hepatocytes. For targeted delivery of DNP to macrophages, advantage was taken of the specific expression of mannose receptor on macrophages. As shown in FIG. 4A, mannose receptor was highly expressed on MPMs (labeled as MΦ) and negligible expression was seen in hepatocytes. Consistently, macrophages showed higher uptake of mDNP-FITC compared to primary mouse hepatocytes (FIG. 4B) and significantly higher Mean Fluorescent Intensity of FITC was associated with macrophages compared to hepatocytes (1070.2±99.8 vs 310.3±45.2, P=1.05E-08, n=6) validating the specificity imparted by mannose functionalization of DNP. It is noteworthy that in addition to macrophages, mannose receptors are also expressed on immature dendritic cells where they mediate high efficiency uptake of glycosylated antigens (Linehan SA. The mannose receptor is expressed by subsets of APC in non-lymphoid organs. BMC Immunol. 2005 Feb. 8; 6:4.)

Figure 5A:
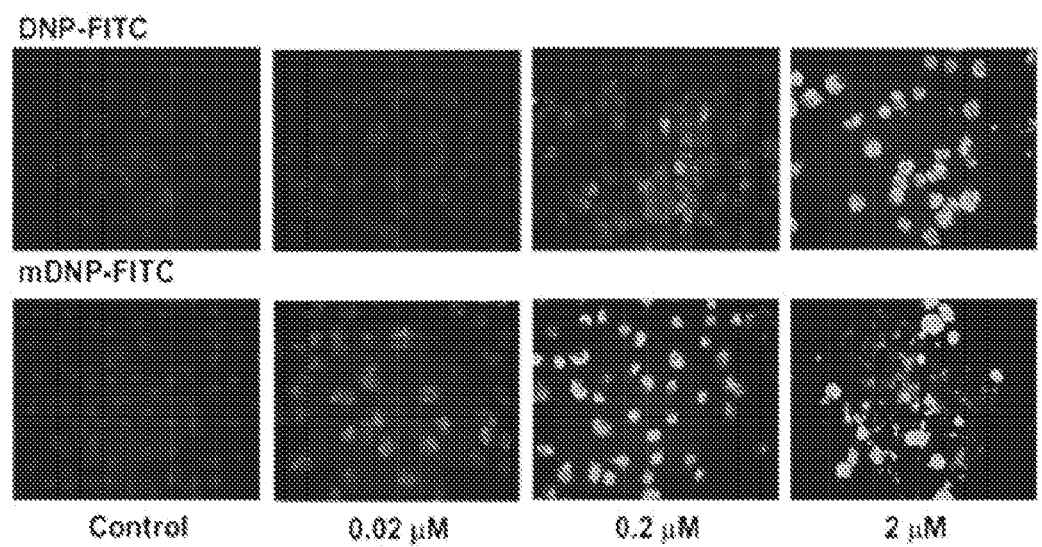
FIG. 5A-5C. Concentration and time dependent increase in the uptake of mDNP-FITC by MPMs.
Figure 5B:
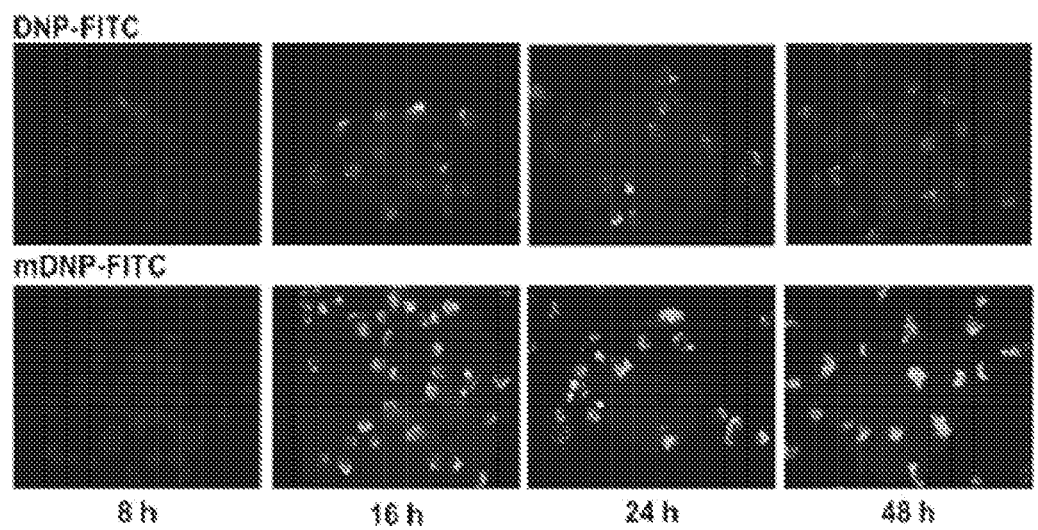
Figure 5C:
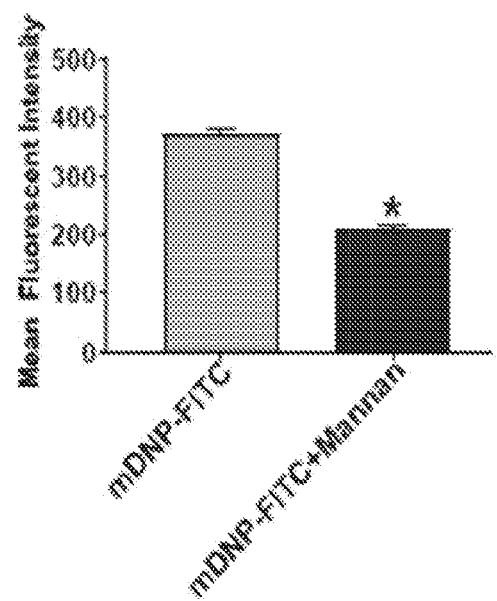

Being phagocytic in nature, macrophages are likely to non-specifically take up DNP and the ability of mannose functionalization to impart specificity was further tested by first comparing concentration-dependent uptake of DNP-FITC and mDNP-FITC by MPMs. A concentration dependent increase in uptake of DNP was noted and at all concentrations tested, uptake of mDNP-FITC was higher than that seen for DNP-FITC (FIG. 5A). Using 0.2 μM as the preferred concentration, time dependence of uptake was evaluated. Not only was the uptake time-dependent, increased uptake of mDNP-FITC was noted at all-time points compared to DNP-FITC (FIG. 5B) demonstrating specific macrophage targeting by mannose functionalization of DNP. Based on the observed fluorescent intensities, maximum uptake was noted by 24 h and it was indistinguishable with that seen at 48 h. More importantly, no morphological changes were noted and cell viability remained unchanged with time. Specificity of uptake of mDNP-FITC by MPMs was further confirmed by evaluating the uptake in cells pre-treated with mannose receptor antagonist Mannan. Significant reduction in mDNP-FITC was noted in MPMs exposed to mannan (FIG. 5C) further demonstrating the specificity of mDNP uptake by macrophages via the mannose receptor.

Intracellular Functionality of LXR-L (T0901317) when Delivered Using mDNP-LXR-L

Figure 6A:
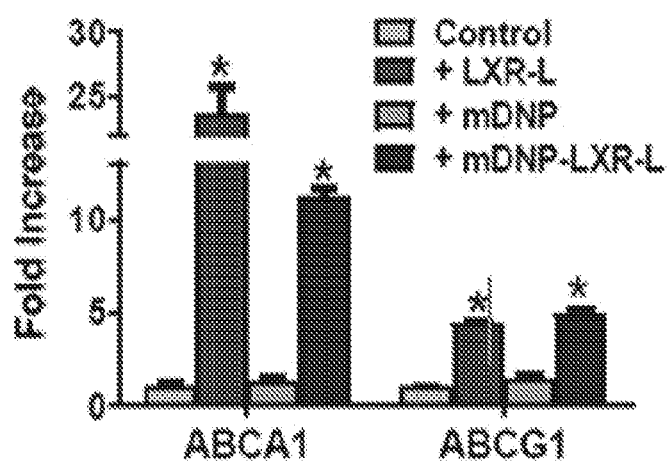
FIG. 6A-6D. mDNP-LXR-L delivered LXR ligand appropriately increases gene expression leading to increased FC efflux.
Figure 6B:
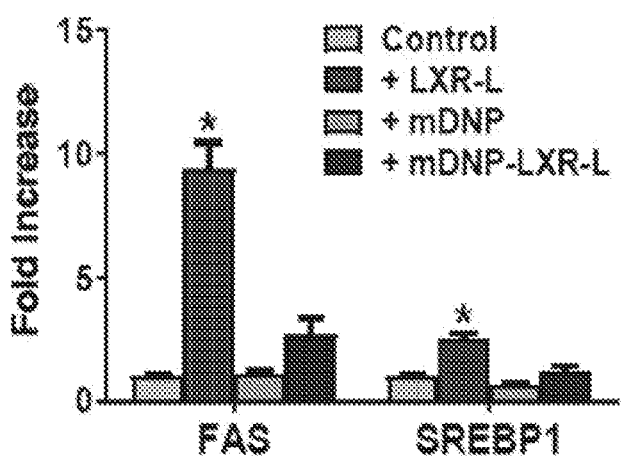

With the primary objective to develop a macrophage-specific delivery platform with limited/negligible delivery to hepatocytes, the ability of mDNP-LXR-L to activate LXR in MPMs and increase the expression of LXR-target genes (e.g., ABCA1 and ABCG1) was tested. As shown in FIG. 6A, compared to untreated controls or mDNP alone, significant increase in ABCA1 and ABCG1 expression was noted when MPMs were treated with mDNP-LXR-L. Furthermore, this LXR-mediated increase in gene expression was comparable to that seen with MPMs treated with free LXR-L. In contrast, as shown in FIG. 6B, mDNP-LXR-L failed to increase the expression of LXR-target genes (e.g., fatty acid synthase, FAS and sterol regulatory element-binding transcription factor 1, SREBP1) in hepatocytes while exposure of hepatocytes to free LXR-L led to significant increase in the expression of FAS and SREBP1.

Figure 6C:
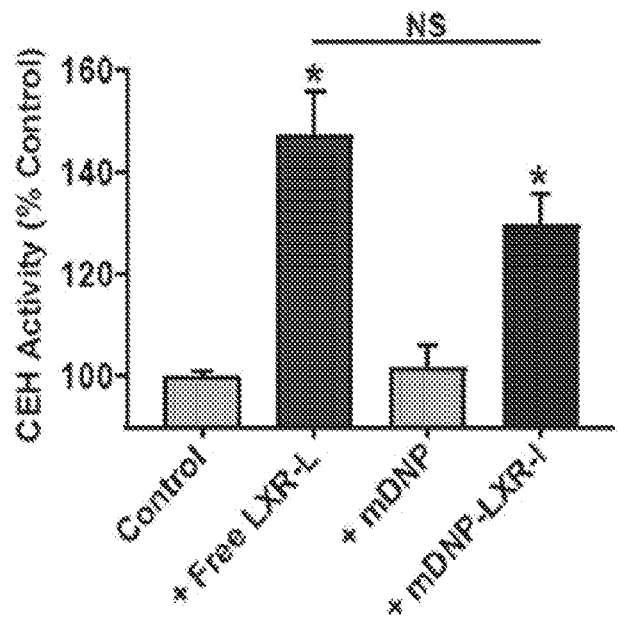
Figure 6D:
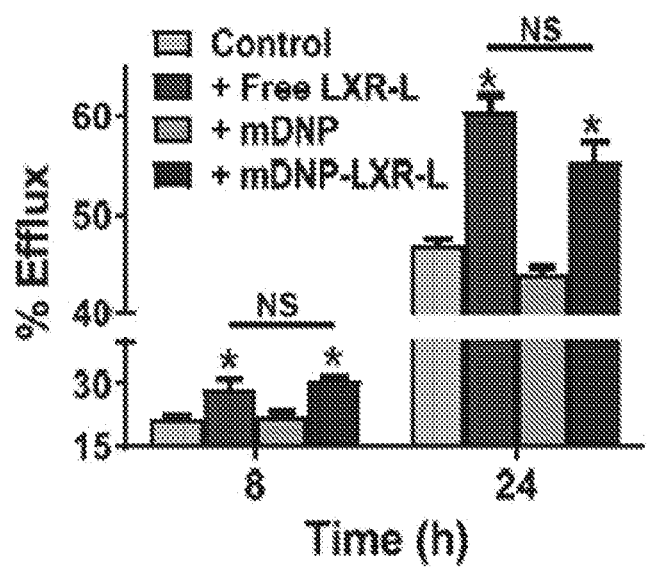

To further examine the functional consequences of LXR-L dependent increase in gene expression, cellular CEH activity was monitored. mDNP-LXR-L delivered LXR ligand significantly increased CEH activity compared to MPMs treated with mDNP alone (FIG. 6C). This increase in CEH activity by mDNP-LXR-L was comparable to that observed by directly treating the MPMs with free ligand indicating that mDNP-LXR-L delivered ligand is equally effective. The potential therapeutic use of developing a macrophage specific platform is to be able to facilitate the removal of stored CE from macrophage foam cells in an effort to reduce atherosclerotic plaque burden. Therefore, to further examine if mDNP-LXR-L mediated increase in ABCA1/ABCG1 expression as well as increase in CEH activity leads to an increase in FC removal from MPMs, FC efflux was monitored. Significantly higher FC efflux was observed from MPMs treated with mDNP-LXR-L compared to those treated with mDNP (FIG. 6D) at both time points tested. Furthermore, this increase in FC efflux was comparable to that seen in MPMs directly treated with free LXR-L demonstrating the efficacy/functionality of LXR ligand delivered by mDNP-LXR-L.

In Vivo Validation

Uptake of mDNP by Atherosclerotic Plaque-Associated Macrophages

Figure 7A:
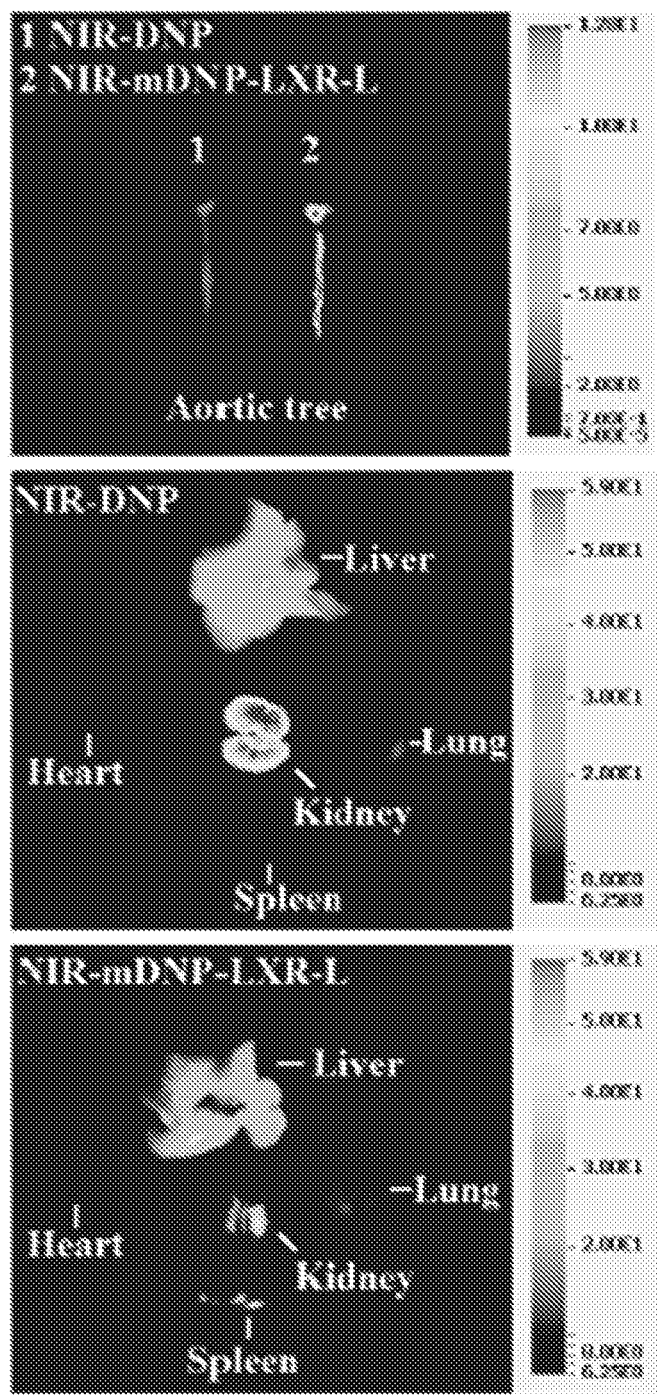
FIG. 7A-7D. In vivo uptake of mDNP by tissues and arterial plaque-associated macrophages: LDLR−/− mice with established atherosclerotic plaques were injected (i.v.) with either NIR-DNP or NIR-mDNP-LXR-L in sterile PBS.
Figure 7B:
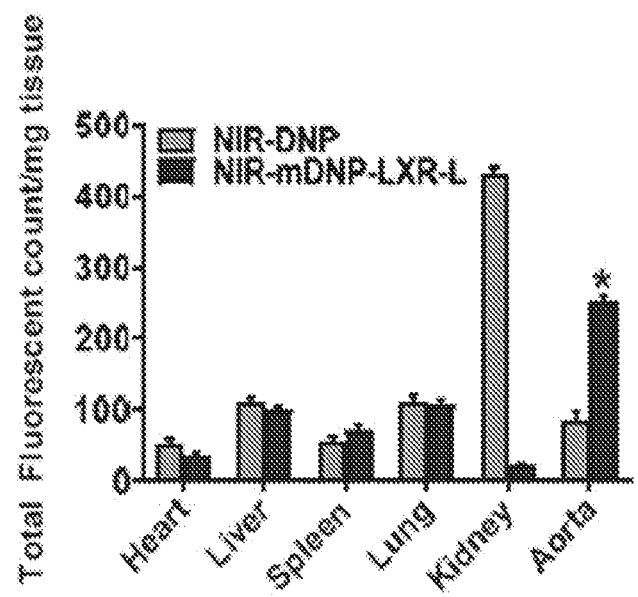

To evaluate delivery of payloads to atherosclerotic plaques, initial experiments compared the uptake of intravenously administered DNP or mDNP conjugated to NIR dye 800CW by different tissues including the aorta. Ex vivo imaging of the dissected aorta was performed to monitor uptake of DNP by plaque-associated macrophages. Considerable increase in uptake of mDNP compared to non-functionalized DNP was noted in the isolated aortic tree (FIG. 7A, Top Panel). It is noteworthy that macrophage-rich tissues such as liver, kidney, lung and spleen also show uptake of NIR-DNP consistent with uptake by resident macrophages in these tissues (FIG. 7A, Middle and Bottom Panels). While mannose-functionalization in NIR-mDNP-LXR-L did not affect the uptake by these tissues, significant increase in uptake was only observed in aorta (FIG. 7B).

Furthermore, mannose functionalization significantly reduced the clearance by kidney probably due to the surface modification of DNP by mannose and PEG spacer.

Figure 7C:
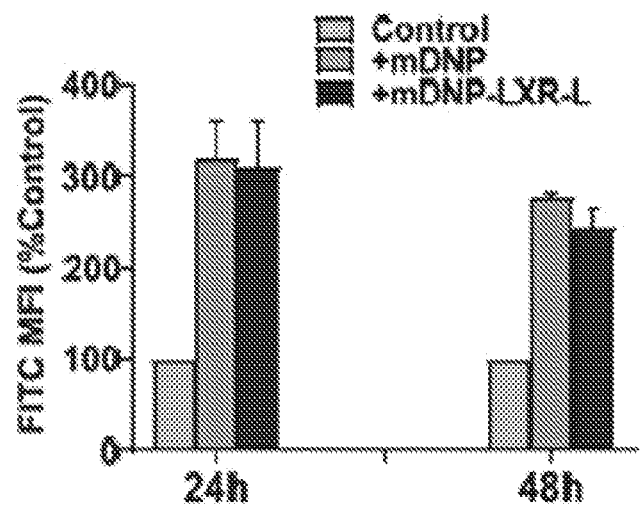
Figure 7D:
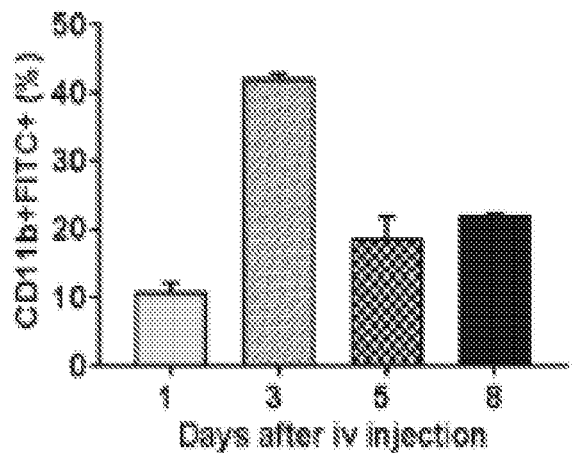

To specifically determine the uptake by arterial plaque-associated macrophages, uptake of mDNP or mDNP-LXR-L fluorescently labeled with FITC was monitored. A 3-fold increase in FITC mean fluorescent intensity was noted in CD11b+ macrophages isolated from atherosclerotic aortic arches from high fat high cholesterol containing Western diet (WD, TD88137)-fed LDLR−/− mice treated with mDNP compared to untreated control mice (FIG. 7C) 24 or 48 h post-injection. It is noteworthy that conjugation with LXR-L did not significantly affect the overall uptake of mDNP by plaque-associated macrophages; no difference noted between the data from mice injected with mDNP and mDNP-LXR-L. To further assess the retention of mDNP by atherosclerotic plaque-associated macrophages after a single intravenous injection, CD11b+macrophages containing FITC label from mDNP were examined by flow cytometry. As shown in FIG. 7D, the percentage of CD11b+FITC+ cells (macrophages with mDNP-FITC) in the atherosclerotic plaques was highest 3-days post intravenous injection. Although a decrease in this population of cells was noted thereafter but 20% of isolated cells were still FITC positive 8 days post injection. Collectively, these in vivo uptake data not only demonstrate successful targeting of atherosclerotic plaque-associated macrophages by mDNP but also indicate >20% retention of mDNP by the plaque-associated macrophages for at least 8 days providing the necessary justification for a weekly treatment regimen. Furthermore, based on the observed lack of effect of mDNP administration on expression of LXR target genes in plaque associated macrophages, no injections were given to the control group in subsequent studies.

Functionality of LXR-L Delivered by mDNP-LXR-L

Figure 4B:
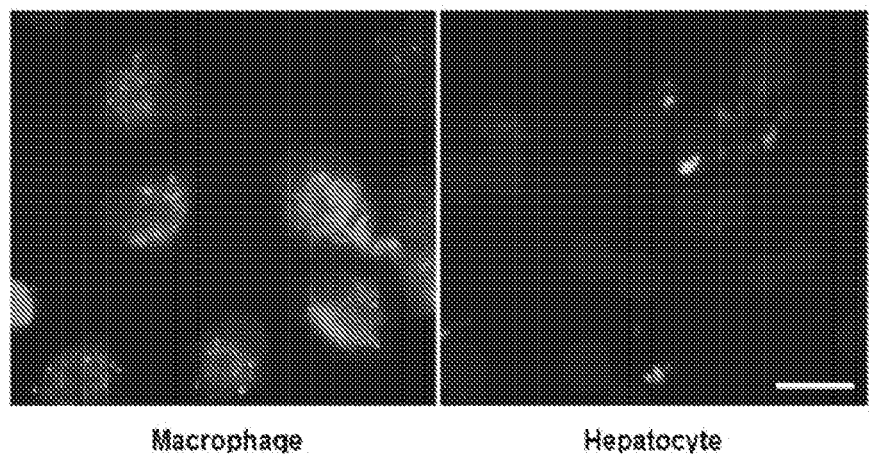
Figure 4C:
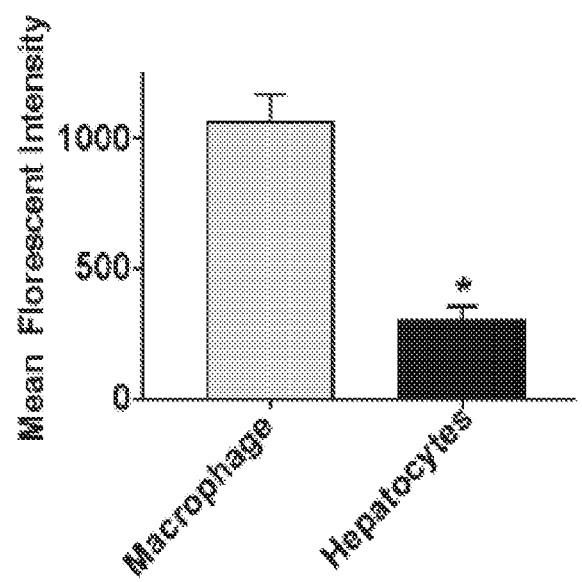
Figure 8A:
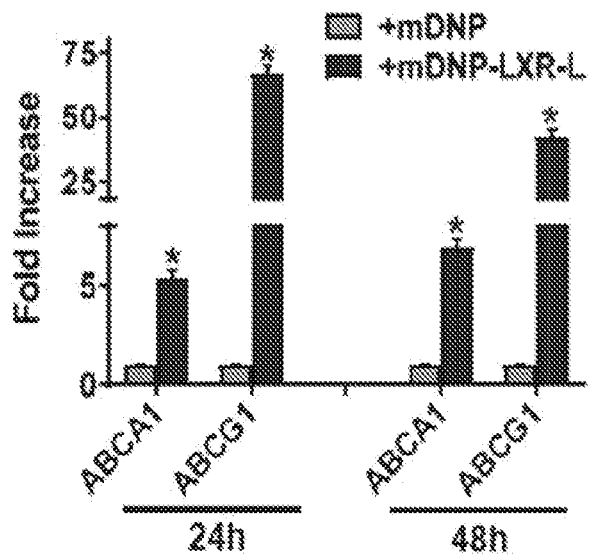
FIG. 8A-8B. Delivery of LXR ligand using mDNP-LXR-L increases expression of LXR target genes in plaque-associated macrophages but does not affect expression of lipogenic genes in the liver. Mannose functionalized DNP (mDNP) with or without conjugated LXR ligand in sterile PBS were injected via the tail vein of LDLR−/− atherosclerotic mice. Control animals were injected with PBS alone. Following euthanasia, aortic arch and liver from each mouse was quickly dissected and total RNA was isolated. Gene expression of the indicated genes in aortic arch associated macrophages (FIG. 8A) and liver (FIG. 8B) was assessed by QPCR as described under "Methods". Data (Mean±SD, n=3) are expressed as fold increase over Controls. *P<0.05.
Figure 8B:
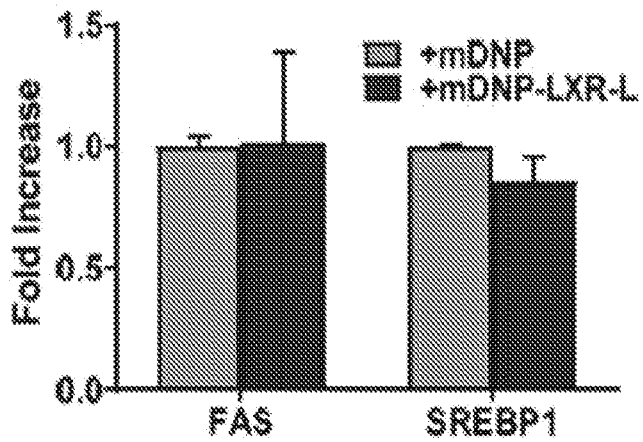

To evaluate the functionality of mDNP-LXR-L in activating LXR in plaque-associated macrophages and thereby enhancing the expression of LXR target genes, expression of the specific target genes was monitored. Intravenously administered mDNP-LXR-L significantly increased the expression of ABCA1 and ABCG1 in atherosclerotic plaque-associated macrophages (FIG. 8A). Consistent with limited uptake of mDNP by hepatocytes as shown in FIG. 4B, no change in hepatic LXR target genes involved in lipogenesis (e.g., FAS, SREBP-1) was observed (FIG. 8B). Therefore, mDNP represents a novel platform for providing the beneficial effects of LXR-L at the atherosclerotic plaque site.

Lack of the Undesirable Hepatic Effects of LXR Ligand Using mDNP-LXR-L

Figure 9A:
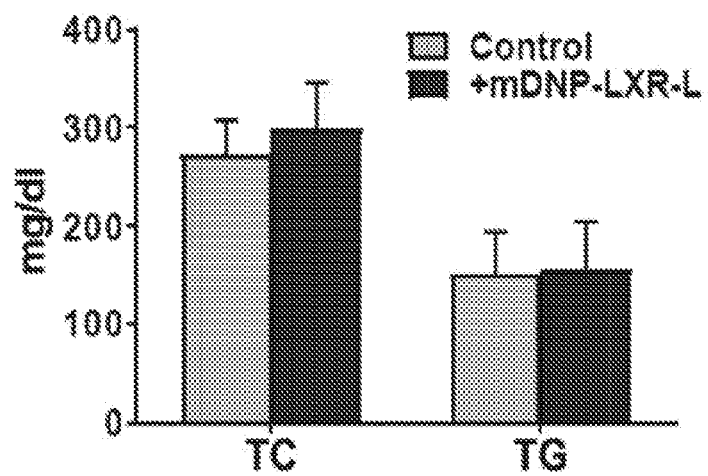
FIG. 9A-9B. Specific delivery of LXR ligand by mDNP-LXR-L does not affect plasma lipid composition and hepatic gene expression: Atherosclerotic LDLR−/− mice were given 4 weekly i.v. injections of mDNP-LXR-L. Plasma and liver were collected at the time of euthanasia and analyzed as described under "Methods".
Figure 9B:
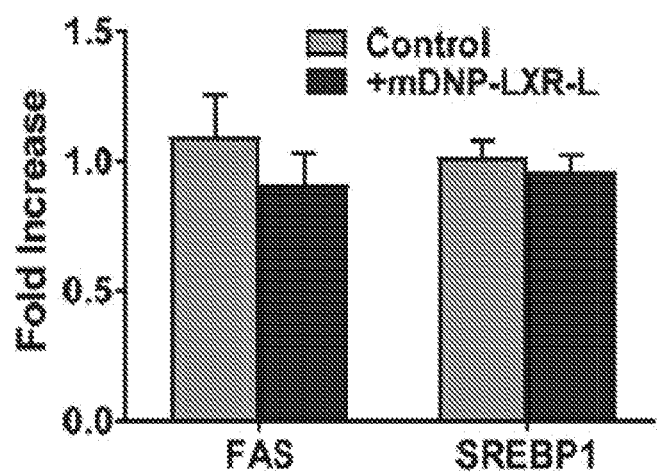

Four weekly i.v. injections of mDNP-LXR-L were given to LDLR−/− mice fed a WD for 12 weeks. Fasting plasma was collected at the time of euthanasia. Treatment with free LXR ligand is reported to result in more than 2-fold increase in plasma triglyceride (TG) and total cholesterol (TC) levels 31. However, plasma TC or TG levels were unchanged between untreated control and mDNP-LXR-L treated mice (FIG. 9A). Although no change in the expression of FAS or SREBP1 was noted 48 h after mDNP-LXR-L injection as shown above in FIG. 8B, expression of these genes was monitored again after 4-week treatment to exclude any possible long term off-target effects. As shown in FIG. 9B, even after 4-week treatment, there was no increase in LXR target genes (FAS and SREBP1) in the liver. These data provide additional evidence that mDNP-LXR-L represents a superior platform for the delivery of LXR-L as it eliminates the undesirable hepatic lipogenic effects.

Modulation of Atherosclerosis

Figure 10A:
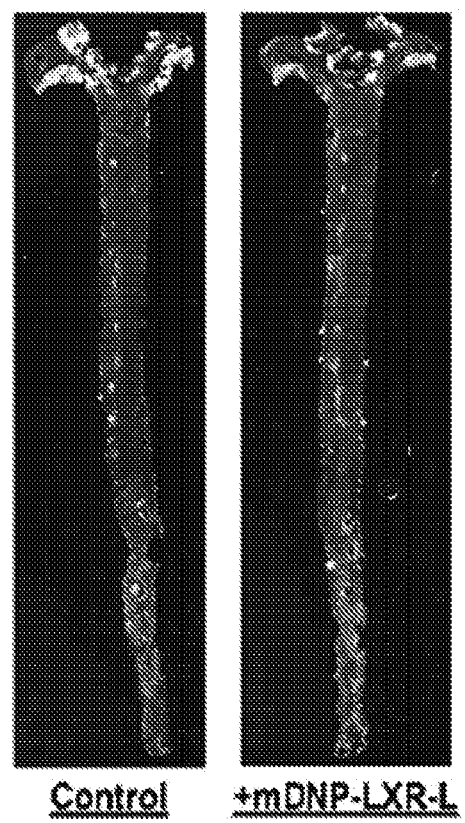
FIG. 10A-10D. Specific delivery of LXR ligand by mDNP-LXR-L attenuates plaque development. LDLR−/− mice were fed a Western type high fat high cholesterol diet for 12 weeks and divided into two experimental groups, and received weekly injections of either PBS (Control) or mDNP-LXR-L (200 µg in 100 µL sterile PBS, labeled Treated) via the tail vein. Mice were euthanized after 4 weeks of treatment.
Figure 10B:
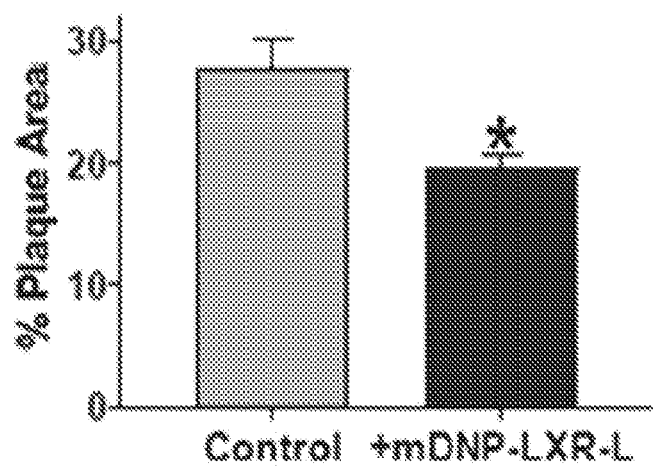
Figure 10C:
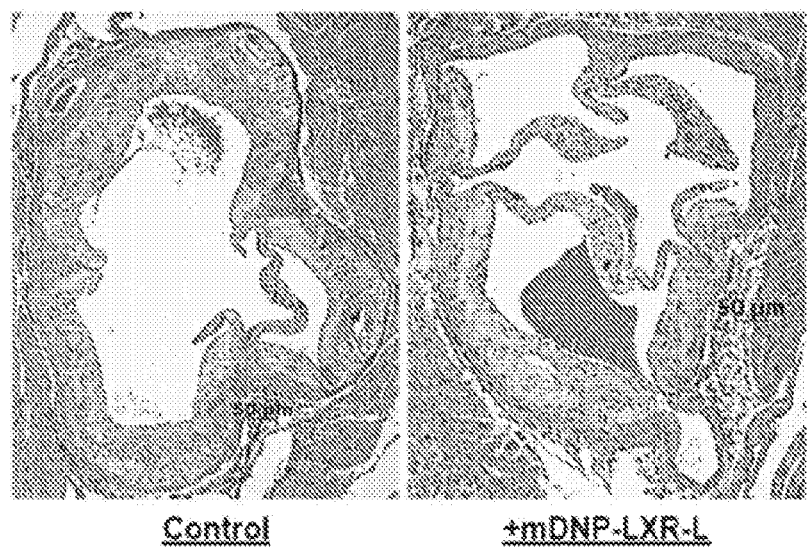
Figure 10D:
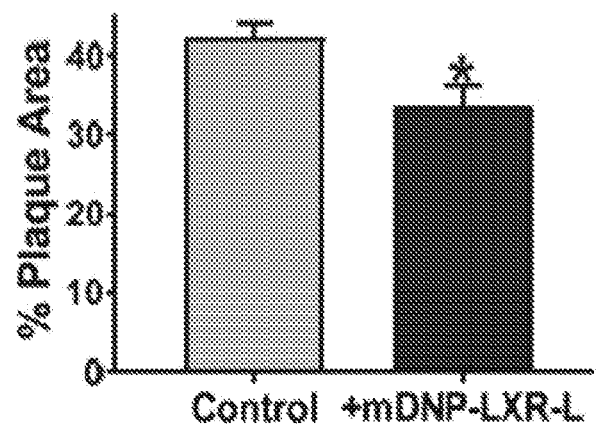

Effects of mDNP-mediated delivery of LXR-L on two critical parameters of atherosclerosis were monitored, namely, plaque size and inflammation. En face analyses shown in FIG. 10A demonstrate a reduction in atherosclerotic plaques following 4-week treatment with mDNP-LXR-L and this decrease in plaque area was statistically significant (FIG. 10B). Effect of treatment on plaque development was also evaluated at another site, namely, the aortic root where plaques develop in the tricuspid aortic valve. As shown in FIG. 10C, reduced plaques were seen in mice receiving 4-week treatment with mDNP-LXR-L compared to untreated mice. Total plaque area of the aortic root or plaques in all three aortic valves was quantified and percent area occupied by the plaques was significantly reduced following 4-week treatment (FIG. 10D).

Figure 11A:
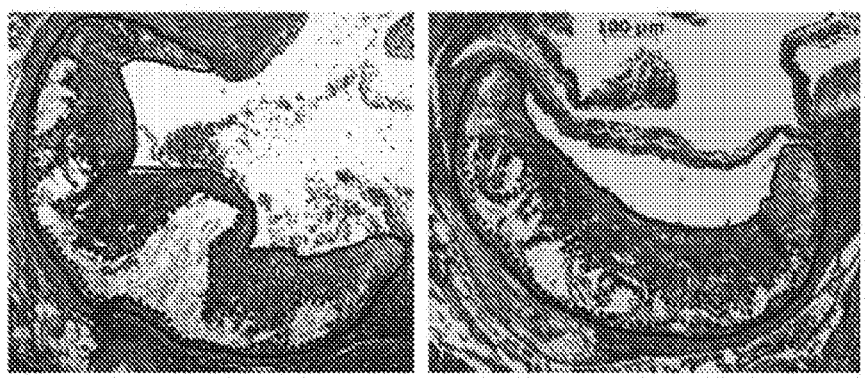
FIG. 11A-11C. Specific delivery of LXR ligand by mDNP-LXR-L attenuates plaque necrosis.
Figure 11B:
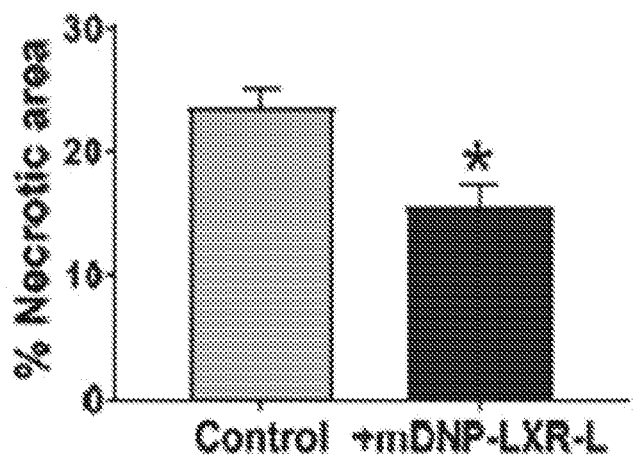

In addition to contributing to the growth and progression of atherosclerotic plaques, CE-laden macrophage foam cells also undergo increased apoptosis leading to the development of necrotic cores. Treatment with mDNP-LXR-L not only reduced plaque area but it also decreased the necrotic areas within an individual plaque (FIG. 11A). Quantification of the necrotic area as percentage of total plaque area showed a significant reduction following treatment with mDNP-LXR-L (FIG. 11B).

Figure 11C:
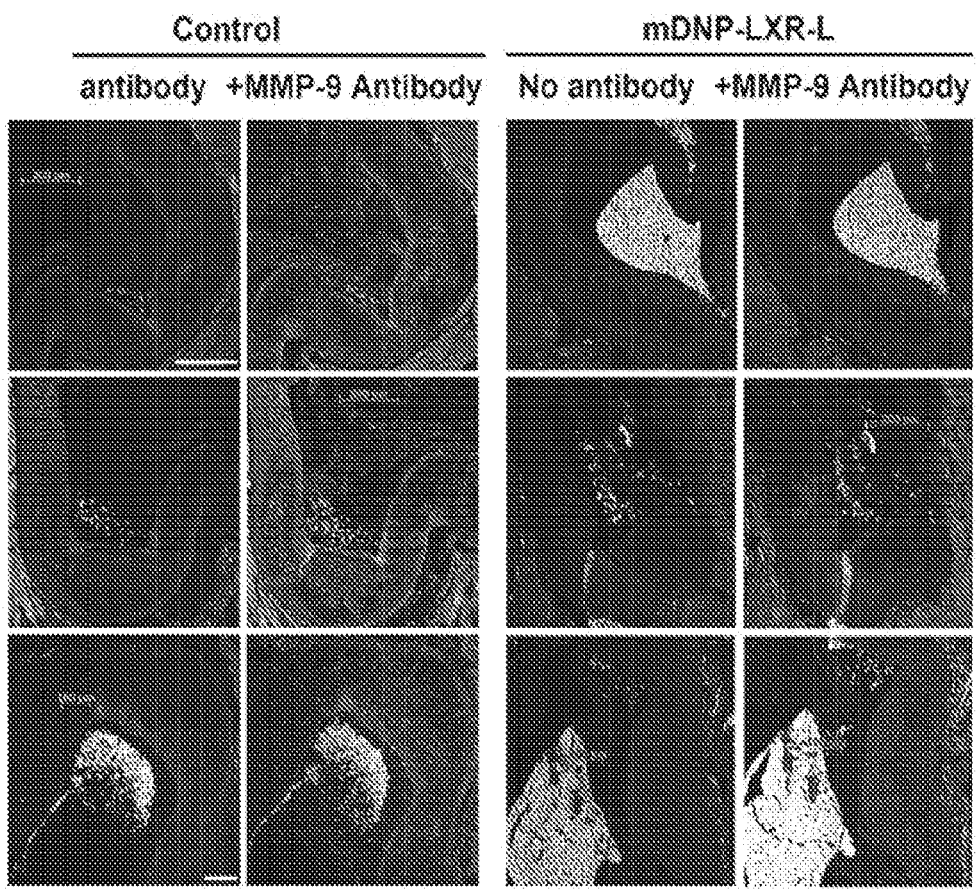

To assess the effects of mDNP-LXR-L on the status of plaque inflammation, expression of MMP-9, an NF-κB target gene, was examined by immunohistochemistry. Dramatically reduced staining of MMP-9 was seen in plaques from mice treated with mDNP-LXR-L (FIG. 11C). These data are consistent with the established/direct effects of LXR activation on macrophage MMP-9 expression[45] and further demonstrate the use of mDNP for delivery of anti-inflammatory agents such as LXR-L directly to the plaque site.

Discussion

Targeted delivery of pharmacological agents is an actively pursued research area and a very desirable therapeutic strategy. Currently available therapies for attenuation of cardiovascular disease focus primarily on reducing plasma cholesterol with the objective of preventing plaque progression. No therapy approved for clinical use is presently available for targeted reduction in existing plaque burden or plaque-associated inflammation. Despite the demonstrated benefits of LXR activation, the undesirable hepatic lipogenic effects have precluded the use of LXR ligands in vivo[31, 32]. Disclosed herein is the successful development of a functionalized DNP-based platform (mDNP-LXR-L) for targeted delivery of LXR ligand to atherosclerotic plaque-associated macrophages where active uptake is mediated by the presence of mannose receptor on macrophages. This is in contrast to passive delivery of LXR-L by PEGylated nanoparticles previously utilized[46]. Most importantly, this functionalized platform eliminates the undesirable hepatic lipogenic effects.

Due to their well-defined structures with the near monodispersity, high water solubility and ease of multi-functionalization, DNP represent a very attractive drug delivery platform. Three important characteristics for effective delivery using DNP are increased circulation time for enhanced uptake, specific cell targeting and delivery of drugs such as LXR ligand (LXR-L) with limited water solubility. PEG spacers were introduced between LXR-L and PAMAM G5.0 as well as mannose and PAMAM G5.0 to accomplish longer resident time in circulation by slowing the rapid uptake of DNP by macrophages in the reticuloendothelial system (RES). Furthermore, the zeta potential of mDNP-LXR-L decreased from ~30 mV (unmodified PAMAM dendrimer G5.0) to ~6 mV and did not change over time (FIG. 2E) suggesting that the PEGylation significantly shielded the positively charged dendrimer surface. This decreased positive charge leads to the longer circulation time and enhanced cytocompatibility of DNP. The increase in circulation time due to PEGylation and specific uptake of mDNP via the mannose receptor likely underlies the enhanced uptake and retention of mDNP-LXR-L by atherosclerotic plaque-associated macrophages out of the RES. Macrophage-specific targeting of mannose-coupled nanoparticles in various tumors has been described earlier[47-49], and mannose-functionalized PAMAM dendrimers have mainly been developed for the study of protein-carbohydrate interactions[50]. Goonewardena et al, however, demonstrated uptake of mannose-conjugated G5 dendrimers by tumor associated macrophages as well as activated bone marrow derived monocyte-macrophages (Goonewardena S N, Zong H, Leroueil P R and Baker J R. Bioorthogonal Chemical Handle for Tracking Multifunctional Nanoparticles. ChemPlusChem 2013, 78, 430-437). Taking advantage of the high expression of folate receptor on activated macrophages, earlier studies have used folate functionalized nanoparticles for macrophage targeting[51] and this strategy is currently being favorably considered for rheumatoid arthritis therapy[52]. Due to dysfunctional endothelium as well as leaky vaso vasorum, atherosclerotic plaques have high levels of exposed collagen IV that has recently been utilized for targeted delivery of nanoparticles to the plaque site[52]. However, whether such targeting strategies deliver the payloads specifically to plaque-associated macrophages remain to be defined. Zhang et al used PLGA-b-PEG based nanoparticles encapsulating a synthetic LXR agonist GW 3965 for passive delivery to atherosclerotic plaque and did not observe an increase in hepatic expression of SREBP-1[46]. However, these studies did not involve any specific macrophage targeting and in the absence of a demonstrated lack of altered hepatocytes uptake of PLGA-b-PEG based nanoparticles, the authors speculated that the observed deficiency of LXR effects in the liver were likely due to accelerated clearance of these nanoparticles by hepatic sinusoids[46]. In contrast, the data presented herein directly demonstrate delivery as well as functionality of mDNP delivered LXR-L in atherosclerotic plaque-associated macrophages with no apparent increase in delivery/functionality of LXR-L in hepatocytes. Therefore, mannose functionalization represents a significant advancement over systemic delivery of LXR-L in elimination of undesirable hepatic lipogenic effects.

In addition to the plaque volume, increased cholesterol content of macrophage foam cells also contributes to increased intra-plaque inflammation likely enhancing the necrotic processes. Large necrotic areas, considered a marker of advanced atherosclerotic lesions, are thought to destabilize the atherosclerotic plaque and induce plaque rupture that underlies acute coronary events such as heart attacks and strokes. Targeted delivery of LXR-L to plaque associated macrophages not only reduced plaque size but also decreased necrosis. Based on the data from a genome-wide scan of LXR chromatin binding and gene regulation in human macrophages, Pehkonen et al reported a strong association with apoptosis related functions[54]. The observed decrease in the necrotic area is, therefore, consistent with the role of LXR-L in attenuating apoptosis. Furthermore, LXR-L dependent increase in FC efflux from plaque-associated macrophage foam cells is likely the second mechanism underlying reduced necrosis. By targeted transgenic over-expression of the rate limiting enzyme CEH in macrophages to stimulate FC efflux, similar reduction in plaque necrosis and macrophage apoptosis have been demonstrated[24]. Collectively, these data show that mDNP-LXR-L mediated delivery of LXR-L to the plaque-associated foam cells reduces necrosis by likely enhancing FC efflux as well as reducing apoptosis.

Increased expression of matrix metalloproteinases (MMPs) and/or imbalance between MMPs and tissue inhibitor of MMPs (TIMP) results in plaque destabilization and rupture leading to acute coronary events in humans. MMP-9 is an NF-κB target gene and activation of LXR induces anti-inflammatory pathways including reduction in NF-κB mediated gene expression[28, 55]. Consistently, mDNP-LXR-L mediated delivery of LXR-L resulted in dramatic reduction in the expression of MMP-9 in the plaques and is likely to contribute to plaque stability.

It needs to be emphasized that currently no treatment strategy is available to facilitate reduction in the size/volume of existing plaques; pharmacological interventions are limited to decreasing hypercholesterolemia either by reducing absorption of dietary cholesterol by Ezetimibe or inhibiting de novo synthesis of cholesterol by Statins. Accurate measurement of plaque volume before and after any treatment is a technical limitation in the evaluation of reduction in plaque size. Intravascular ultra sound (IVUS) is a recent development for in vivo assessment of plaque burden but given its invasive nature, it is currently restricted to very high-risk patients. Nonetheless, in one landmark study using 5 weekly injections of a reconstituted HDL particle to enhance FC efflux from plaque-associated macrophage foam cells, reduction in plaque volume by 1.06±3.17% (assessed by IVUS) was considered clinically significant[56]. Furthermore, a recently concluded randomized controlled trial showed a 0.95% decrease in atheroma volume following treatment with Proprotein convertase subtilisin kexin type 9 (PCSK9) inhibitor Evolocumab (Nicholls S J, Puri R, Anderson T, Ballantyne C M, Cho L, Kastelein J J, Koenig W, Somaratne R7, Kassahun H, Yang J, Wasserman S M, Scott R, Ungi I, Podolec J, Ophuis A O, Cornel J H, Borgman M, Brennan D M, Nissen S E. Effect of Evolocumab on Progression of Coronary Disease in Statin-Treated Patients: The GLAGOV Randomized Clinical Trial. JAMA. 2016 Dec. 13; 316(22): 2373-2384).

In conclusion, these pre-clinical studies show that functionalized DNP-based platforms for targeted delivery of therapeutics can be used as alternatives or in conjunction with the currently used strategies for reducing the burden of cardiovascular diseases and/or improving plaque stability.

References cited in this example
1. He H, Ghosh S, Yang H. Nanomedicines for dysfunctional macrophage-associated diseases. J. Control. Release. 2017 February; 247:106-126
2. Martinez-Pomares L. The mannose receptor. J. Leukoc. Biol. 2012 December; 92:1177-1186
3. Shen J, Hilgenbrink A R, Xia W, Feng Y, Dimitrov D S, Lockwood M B, Amato R J, Low P S. Folate receptor-β constitutes a marker for human proinflammatory monocytes. J. Leukoc. Biol. 2014 October; 96:563-570
4. Miyanishi M, Tada K, Koike M, Uchiyama Y, Kitamura T, Nagata S. Identification of TIM4 as a phosphatidylserine receptor. Nature. 2007 November; 450:435-439
5. Park D, Tosello-Trampont A-C, Elliott M R, Lu M, Haney L B, Ma Z, Klibanov A L, Mandell J W, Ravichandran K S. BAI-1 is an engulfment receptor for apoptotic cells upstream of the elmo/dock180/rac module. Nature. 2007 November; 450:430-434
6. Yi Y-S. Folate receptor-targeted diagnostics and therapeutics for inflammatory diseases. Immune Netw. 2016 December; 16:337-343
7. Zahr A S, Davis C A, Pishko M V. Macrophage uptake of core-shell nanoparticles surface modified with poly (ethylene glycol). Langmuir. 2006 September; 22:8178-8185
8. Pelaz B, del Pino P, Maffre P, Hartmann R, Gallego M, Rivera-Fernandez S, de la Fuente J M, Nienhaus G U, Parak W J. Surface functionalization of nanoparticles with polyethylene glycol: Effects on protein adsorption and cellular uptake. ACS nano. 2015 July; 9: 6996-7008
9. Lipka J, Semmler-Behnke M, Sperling R A, Wenk A, Takenaka S, Schleh C, Kissel T, Parak W J, Kreyling W G. Biodistribution of peg-modified gold nanoparticles following intratracheal instillation and intravenous injection. Biomaterials. 2010 September; 31:6574-6581
10. Holden C A, Tyagi P, Thakur A, Kadam R, Jadhav G, Kompella U B, Yang H. Polyamidoamine dendrimer hydrogel for enhanced delivery of anti-glaucoma drugs. Nanomedicine. 2012 July; 8:776-783
11. Yuan Q, Yeudall W A, Yang H. Pegylated polyamidoamine dendrimers with bis-aryl hydrazone linkages for enhanced gene delivery. Biomacromolecules. 2010 August; 11:1940-1947
12. Yuan Q, Lee E, Yeudall W A, Yang H. Dendrimer-triglycine-egf nanoparticles for tumor imaging and targeted nucleic acid and drug delivery. Oral Oncol. 2010 September; 46:698-704
13. Tall A R, Yvan-Charvet L. Cholesterol, inflammation and innate immunity. Nat. Rev. Immunol. 2015 February; 15:104-116
14. Hendrikx T, Walenbergh S, Hofker M, Shiri-Sverdlov R. Lysosomal cholesterol accumulation: Driver on the road to inflammation during atherosclerosis and non-alcoholic steatohepatitis. Obes. Rev. 2014 May; 15:424-433
15. Yancey P G, St Clair R. Mechanism of the defect in cholesteryl ester clearance from macrophages of atherosclerosis-susceptible white carneau pigeons. J. Lipid Res. 1994 December; 35:2114-2129
16. Rothblat G, De La Llera-Moya M, Favari E, Yancey P, Kellner-Weibel G. Cellular cholesterol flux studies: Methodological considerations. Atherosclerosis. 2002 July; 163:1-8
17. Ghosh S, St. Clair R W, Rudel L L. Mobilization of cytoplasmic C E droplets by overexpression of human macrophage cholesteryl ester hydrolase. J. Lipid Res. 2003 October; 44:1833-1840
18. Zhao B, Song J, St. Clair R W, Ghosh S. Stable overexpression of human macrophage cholesteryl ester hydrolase results in enhanced free cholesterol efflux from human THP1 macrophages. Am. J. Physiol., Cell Physiol. 2007 January; 292:C405-C412
19. He H, Lamina M G, Wang J, Korzun W J, Yang H, Ghosh S. Bolstering cholesteryl ester hydrolysis in liver: A hepatocyte-targeting gene delivery strategy for potential alleviation of atherosclerosis. Biomaterials. 2017 June; 130:1-13
20. Wang N, Lan D, Chen W, Matsuura F, Tall A R. ATP-binding cassette transporters G1 and G4 mediate cellular cholesterol efflux to high-density lipoproteins. Proc. Natl. Acad. Sci. U.S.A. 2004 June; 101: 9774-9779
21. Joyce C W, Amar M J, Lambert G, Vaisman B L, Paigen B, Najib-Fruchart J, Hoyt R F, Neufeld E D, Remaley A T, Fredrickson D S, Brewer H B, Santamarina-Fojo S. The ATP binding cassette transporter A1 (ABCA1) modulates 21. the development of aortic atherosclerosis in C57Bl/6 and ApoE-knockout mice. Am. J. Physiol., Cell Physiol. 2002 January; 99:407-412
22. Singaraja R R, Fievet C, Castro G, James E R, Hennuyer N, Clee S M, Bissada N, Choy J C, Fruchart J-C, McManus B M, Bart S, Michael R H. Increased ABCA1 activity protects against atherosclerosis. J. Clin. Invest. 2002 July; 110:35-42
23. Aiello R J, Brees D, Bourassa P-A, Royer L, Lindsey S, Coskran T, Haghpassand M, Francone O L. Increased atherosclerosis in hyperlipidemic mice with inactivation of ABCA1 in macrophages. Arterioscler. Thromb. Vasc. Biol. 2002 April; 22:630-637
24. Zhao B, Song J, Chow W N, Clair R W S, Rudel L L, Ghosh S. Macrophage-specific transgenic expression of cholesteryl ester hydrolase significantly reduces atherosclerosis and lesion necrosis in ldlr−/−mice. J. Clin. Invest. 2007 October; 117:2983-2992
25. Oram J F, Heinecke J W. ATP-binding cassette transporter A1: A cell cholesterol exporter that protects against cardiovascular disease. Physiol. Rev. 2005 October; 85:1343-1372
26. Joseph S B, Tontonoz P. LXRs: New therapeutic targets in atherosclerosis? Curr. Opin. Pharmacol. 2003 April; 3:192-197
27. Ghosh S, Zhao B, Bie J, Song J. Macrophage cholesteryl ester mobilization and atherosclerosis. Vascul. Pharmacol. 2010 October; 52:1-10
28. Zelcer N, Tontonoz P. Liver x receptors as integrators of metabolic and inflammatory signaling. J. Clin. Invest. 2006 March; 116:607-614
29. Joseph S B, McKilligin E, Pei L, Watson M A, Collins A R, Laffitte B A, Chen M, Noh G, Goodman J, Hagger G N, Tran J, Tippin T K, Wang X, Lusis A J, Hsueh W A, Law R E, Collins J L, Willson T M, Tontonoz P. Synthetic LXR ligand inhibits the development of atherosclerosis in mice. Proc. Natl. Acad. Sci. U.S.A. 2002 May; 99:7604-7609
30. Tangirala R K, Bischoff E D, Joseph S B, Wagner B L, Walczak R, Laffitte B A, Daige C L, Thomas D, Heyman R A, Mangelsdorf D J. Identification of macrophage liver x receptors as inhibitors of atherosclerosis. Proc. Natl. Acad. Sci. U.S.A. 2002 September; 99:11896-11901
31. Schultz J R, Tu H, Luk A, Repa J J, Medina J C, Li L, Schwendner S, Wang S, Thoolen M, Mangelsdorf D J, Lustig K D, Shan B. Role of LXRs in control of lipogenesis. Genes Dev. 2000 November; 14:2831-2838
32. Cha J-Y, Repa J J. The liver x receptor (LXR) and hepatic lipogenesis the carbohydrate-response elementbinding protein is a target gene of LXR. J. Biol. Chem. 2007 January; 282:743-751
33. Merched A J, Ko K, Gotlinger K H, Serhan C N, Chan L. Atherosclerosis: Evidence for impairment of resolution of vascular inflammation governed by specific lipid mediators. FASEB J. 2008 October; 22:3595-3606
34. Libby P, Tabas I, Fredman G, Fisher E A. Inflammation and its resolution as determinants of acute coronary syndromes. Circ. Res. 2014 June; 114:1867-1879
35. Davies M J, Thomas A C. Plaque fissuring—the cause of acute myocardial infarction, sudden ischaemic death, and crescendo angina. Br. Heart J. 1985 April; 53:363
36. Libby P, Aikawa M. New insights into plaque stabilisation by lipid lowering. Drugs. 1998; 56:9-13
37. Yang H, Kao W J, Synthesis and characterization of nanoscale dendritic RGD clusters for potentialapplications in tissue engineering and drug delivery, Int. J. Nanomedicine 2007; 2: 89-99.
38. McIntyre J O, Scherer R L, Matrisian L M. Near-infrared optical proteolytic beacons for in vivo imaging of matrix metalloproteinase activity, Methods Mol. Biol. 2010; 622: 279-304.
39. Yang H, Morris J J, Lopina S T. Polyethylene glycol-polyamidoamine dendritic micelle as solubility enhancer and the effect of the length of polyethylene glycol arms on the solubility of pyrene in water, J. Colloid Interface Sci. 2004 May 273:148-154.
40. Hylemon P B, Gurley E, Kubaska W, Whitehead T, Guzelian P, Vlahcevic Z, Suitability of primary monolayer cultures of adult rat hepatocytes for studies of cholesterol and bile acid metabolism, J. Biol. Chem. 1985; 260:1015-1019.
41. Hajjar D, Minick C R, Fowler S. Arterial neutral cholesteryl esterase. A hormone-sensitive enzyme distinct from lysosomal cholesteryl esterase, J. Biol. Chem. 1983; 258: 192-198.
42. Ghosh S, Grogan W M. Activation of rat liver cholesterol ester hydrolase by cAMP-dependent protein kinase and protein kinase C, Lipids 1989; 24:733-736.
43. Galkina E, Kadl A, Sanders J, Varughese D, Sarembock I J, K. Ley K. Lymphocyte recruitment into the aortic wall before and during development of atherosclerosis is partially L-selectin dependent, J. Exp. Med. 2006; 203: 1273-1282.
44. Bie J, Zhao B, GhoshS. Atherosclerotic lesion progression is attenuated by reconstitution with bone marrow from macrophage-specific cholesteryl ester hydrolase transgenic mice, Am. J. Physiol. Regul. Integr. Comp. Physiol. 2011; 301: R967-R974.
45. Castrillo A, Joseph S B, Marathe C, Mangelsdorf D J, Tontonoz P. Liver x receptor-dependent repression of matrix metalloproteinase-9 expression in macrophages. J. Biol. Chem. 2003 March; 278:10443-10449
46. Zhang X Q, Even-Or O, Xu X, van Rosmalen M, Lim L, Gadde S, Farokhzad O C, Fisher E A. Nanoparticles containing a liver x receptor agonist inhibit inflammation and atherosclerosis. Adv. Healthc. Mater. 2015 January; 4:228-236
47. Zhu S, Niu M, O'Mary H, Cui Z. Targeting of tumor-associated macrophages made possible by PEG-sheddable, mannose-modified nanoparticles. Mol. Pharm. 2013 September; 10:3525-3530
48. Byeon H J, Lee S, Min S Y, Lee E S, Shin B S, Choi H-G, Youn Y S. Doxorubicin-loaded nanoparticles consisted of cationic-and mannose-modified-albumins for dual-targeting in brain tumors. J. Control. Release. 2016 March; 225:301-313
49. He C, Yin L, Tang C, Yin C. Multifunctional polymeric nanoparticles for oral delivery of TNF-α siRNA to macrophages. Biomaterials. 2013 April; 34:2843-2854
50. Samuelson L E, Sebby K B, Walter E D, Singel D J, Cloninger M J. EPR and affinity studies of mannose-tempo functionalized PAMAM dendrimers. Org. Biomol. Chem. 2004 November; 2:3075-3079
51. Zhao X, Li H, Lee R J. Targeted drug delivery via folate receptors. Expert Opin. Drug Deliv. 2008 March; 5:309-319
52. Nogueira E, Gomes A C, Preto A, Cavaco-Paulo A. Folate-targeted nanoparticles for rheumatoid arthritis therapy. Nanomedicine. 2016 May; 12:1113-1126
53. Kamaly N, Fredman G, Fojas J J R, Subramanian M, Choi W I, Zepeda K, Vilos C, Yu M, Gadde S, Wu J, Milton J, Leitao R C, Rosa Fernandes L, Hasan M, Gao H, Nguyen V, Harris J, Tabas I, Farokhzad O C. Targeted interleukin-10 nanotherapeutics developed with a microfluidic chip enhance resolution of inflammation in advanced atherosclerosis. ACS nano. 2016 May; 10:5280-5292
54. Pehkonen P, Welter-Stahl L, Diwo J, Ryynanen J, Wienecke-Baldacchino A, Heikkinen S, Treuter E, Steffensen K R, Carlberg C. Genome-wide landscape of liver x receptor chromatin binding and gene regulation in human macrophages. BMC genomics. 2012 January; 13:50
55. Ogawa S, Lozach J, Benner C, Pascual G, Tangirala R K, Westin S, Hoffmann A, Subramaniam S, David M, Rosenfeld M G, Molecular determinants of crosstalk between nuclear receptors and toll-like receptors, Cell 2005; 122: 707-721.
56. Nissen S E, Tsunoda T, Tuzcu E M, Schoenhagen P, Cooper C J, Yasin M, Eaton G M, Lauer M A, Sheldon W S, Grines C L. Effect of recombinant apoa-i milano on coronary atherosclerosis in patients with acute coronary syndromes: A randomized controlled trial. JAMA. 2003 November; 290:2292-2300

Example 2. Anti-Atherosclerogenic Hepatocyte-Specific Expression of Cholesteryl Ester Hydrolase by Galactose-Functionalized Dendrimer Accumulation of cholesterol as cholesteryl esters (CE) in artery wall associated macrophage foam cells is the hall mark of atherosclerosis, a process that underlies the development of cardiovascular diseases. While the current therapeutics limit further CE accumulation mainly by reducing cholesterol endogenous synthesis in the liver, these agents cannot remove cholesterol from existing atherosclerotic plaques; CE can only be removed into the feces either as free cholesterol (FC) or following biotransformation to bile acids (BA). Liver is not only the main organ for de novo cholesterol biosynthesis, but is also the major organ regulating the final elimination of CE. Previous studies have established the central role of hepatic cholesteryl ester hydrolase (CEH) in facilitating intrahepatic hydrolysis of lipoprotein-derived CE and enhancing the removal of resulting FC into bile and feces. The overall objective of this present study was to develop hepatocyte-specific delivery of CEH achieved via functionalization of polyamidoamine (PAMAM) Generation 5 (G5) by galactose that binds with high affinity to hepatocyte-specific asialoglycoprotein receptor (ASGPR). The cytotoxic effects of high cationic charges of G5 were circumvented by the addition of PEG spacers (Gal-G5). The data presented herein show increased specific uptake of Gal-G5 by hepatocytes in vitro and liver in vivo. Furthermore, unregulated CEH expression in hepatocytes led to increase in intracellular hydrolysis of HDL-CE and subsequent conversion/secretion of released FC into bile acids. The development of this non-toxic and efficient liver-specific gene delivery platform is used to enhance hepatic processes involved in cholesterol elimination.

Background

Cardiovascular disease (CVD) continues to be the number one cause of morbidity and mortality in the Western World including the USA.[1-2] The underlying cause of CVD or heart disease is atherosclerosis or deposition of cholesteryl ester-laden macrophage foam cells in the arterial wall, a process that starts in early teen years and progresses silently for years before the manifestation of any clinical symptoms.[3-4] Once the risk is identified or clinical symptoms are apparent, current therapeutic strategies focus on reduction in plasma cholesterol either by restricting intake (by dietary modification or use of inhibitors of intestinal cholesterol absorption such as Ezetimibe) or by reducing de novo cholesterol biosynthesis (by Statins). The rationale is to reduce the influx of cholesterol into the macrophages thereby reducing new foam cell formation and plaque progression. Once the plaque is formed resulting from accumulation of macrophage foam cells, the only mechanism to reduce the lipid burden is by facilitating/enhancing the removal of CE from macrophage foam cells.[5] Furthermore, reduction in the lipid core of the plaques is also crucial to increasing plaque stability and thereby possibly reducing acute cardiovascular events. Although the importance of increasing the flux of cholesterol from macrophages to liver for final elimination (or reverse cholesterol transport, RCT) is widely recognized, no therapy is currently available to enhance the removal of CE from existing plaque and facilitate plaque regression or increase plaque stability.[6] Such a strategy is crucial to reduce the burden of existing disease in addition to preventing the progression targeted by the current therapeutics.

Under normal physiological setting, a homeostatic balance between cholesterol influx (unregulated uptake of modified low density lipoprotein, mLDL) and efflux pathways (removal of un-esterified or free cholesterol, FC by Apolipoprotein A1, ApoA1 or High density lipoprotein, HDL) restricts pathological accumulation of CE in macrophages. In fact, initial uptake of mLDL or oxidized (ox-LDL) that infiltrate the arterial wall by macrophages can be considered as a beneficial process that prevents the initiation of inflammatory processes resulting from such lipoprotein infiltration. However, pathological consequences are only associated with excessive accumulation of CE within macrophage foam cells and these can arise from either increase in influx or decrease in efflux. With the failure to show any therapeutic improvement in several clinical trials, which aimed at increasing HDL-C either by treatment with niacin (AIM-HIGH and HPS2-Thrive) or by cholesteryl ester transfer protein (CETP) inhibition,[7] consequently, in recent years focus has shifted from cholesterol content of HDL or HDL-C to the ability of HDL to remove cholesterol from macrophage foam cells.[4] Accordingly, correlation between HDL efflux capacity and cardiovascular disease has been established in clinical studies. It is noteworthy that while macrophage foam cells store cholesterol as CE, only free cholesterol (FC) is available for efflux to ApoA1 or HDL via the membrane cholesterol transporters ABCA1 or ABCG1, thus making intracellular hydrolysis of CE by CE hydrolase (CEH) an important and likely rate-limiting step in cholesterol efflux pathway.[8-9] Consistently, previous work has shown that macrophage-specific transgenic expression of human macrophage CEH significantly attenuated Western-diet induced atherosclerosis in Ldlr-/- mice.[10-11]

Liver is the central organ for the final elimination of cholesterol from the body. Cholesterol removed from the peripheral organs including plaque associated macrophages returns to the liver via HDL that contain >80% of cholesterol as CE.[12] HDL receptor SR-BI on hepatocytes facilitates the selective delivery of HDL associated CE or FC. While HDL-FC is thought to be rapidly secreted into bile, the fate of HDL-CE is only beginning to be understood.[6] The central role of hepatic CEH in the hydrolysis of HDL-delivered CE has been shown, demonstrating liver-specific transgenic expression of human liver CEH enhanced flux of HDL-CE to bile and feces and reduced Western-diet induced atherosclerosis.[10,13] It is noteworthy that there is association between bile acid secretion and reduced risk for the development of CVD[14] and increased risk of CVD is observed in heterozygous Familial Hypercholesterolemia patients that have reduced bile acid excretion[15]. These pre-clinical studies establish the importance of enhanced unidirectional movement of cholesterol from macrophage foam cells to liver and finally to bile/feces as an anti-atherogenic step. Therefore, strategies to enhance final elimination of cholesterol by modulation of hepatic processing of HDL-delivered CE are required for the development of novel anti-atherogenic agents and liver-specific delivery of CEH represents one such approach.

Although viral vectors are the most efficient systems for gene delivery in vivo and have been successfully used in pre-clinical animal studies for functional validation of genes, major drawbacks include high immunogenicity, high levels of pre-existing immunity, transient expression of the transgene, and low capacity to accommodate certain genes required for clinical applications.[16-17] With the advancement of nanotechnology, the number of clinical trials based on application of nanoparticles-based non-viral gene delivery systems is rapidly increasing.[18-19] In an effort to facilitate the "bench to bedside" and increase CEH expression in liver for enhanced cholesterol elimination from the body, development of safe, liver hepatocyte-specific and highly efficient non-viral vectors is therefore a critical and urgent need.[20, 21-23] Although the majority of cells (60-80%) in the liver are parenchymal hepatocytes, most nanoparticle-based non-viral vectors are typically taken up by non-parenchymal Kupffer cells (mononuclear phagocyte system, MPS).[24-25] Thus, maximizing the active uptake by hepatocytes meanwhile minimizing the passive clearance by MPS in liver is an important consideration for the development of hepatocyte-specific non-viral gene delivery platform. Due to the several distinctive merits of polyamidoamine (PAMAM) dendrimer, including well-defined spherical architecture (around 10 nm), enormous surface amino groups capable to efficiently encapsulate gene though electrostatic interactions, as well as endosomal-lysosomal cavity escape by osmatic swelling from proton-sponge effect,[26-27] PAMAM dendrimer have been extensively investigated as non-viral gene delivery vector for anticancer therapy.[28-30] Moreover, PAMAM have been widely modified with various targeted ligands, such as carbohydrate moieties,[31] antibodies,[32] peptides[33-34] or aptamers[35-36] in order to enhance the tissue-specific target. Nevertheless, successful application in clinic of PAMAM-based on nanomedicines is still largely restricted by the abundant cation-associated toxicities of PAMAM dendrimers.

Figure 12:
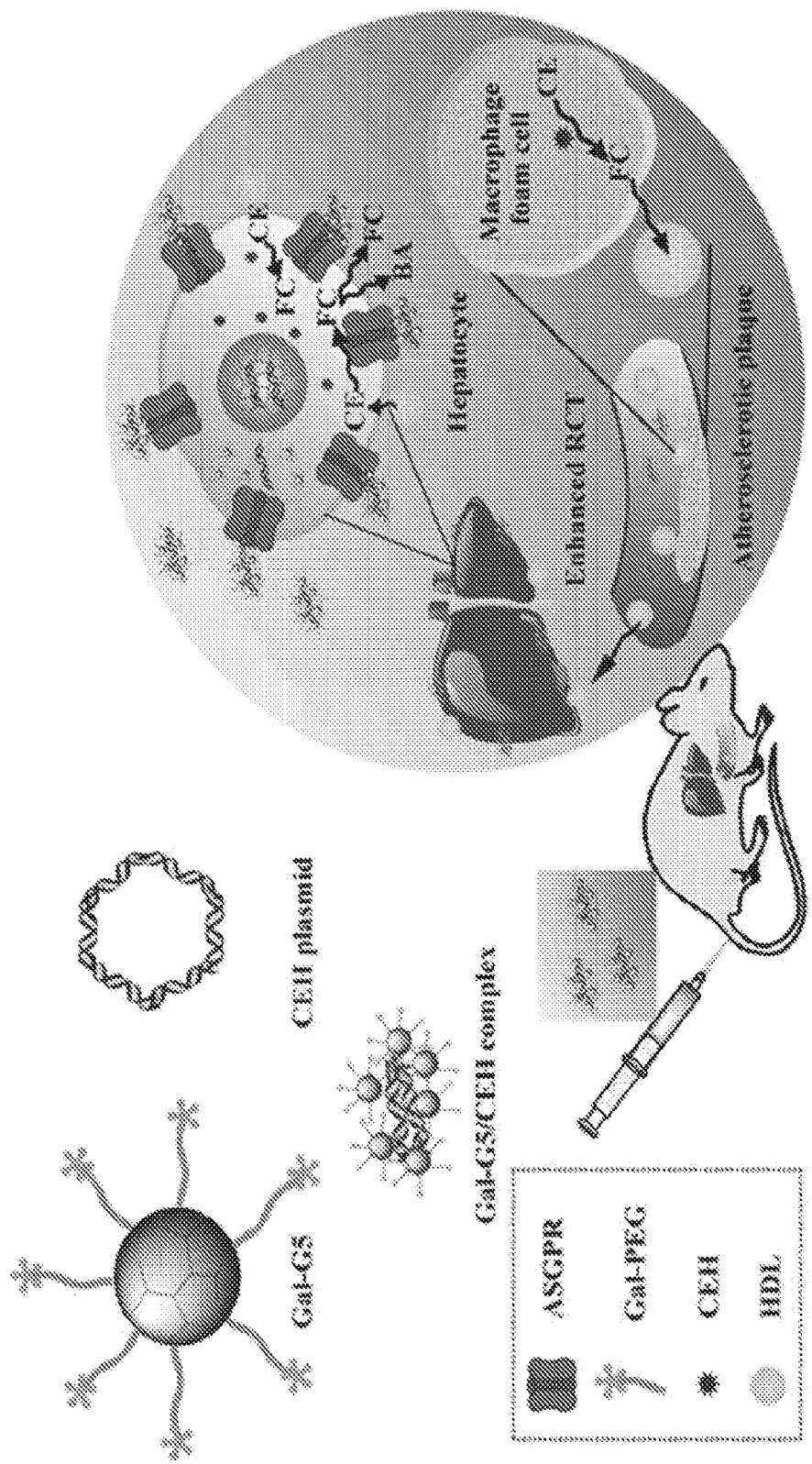
FIG. 12. Design of hepatocyte-specific anti-atherogenic gene delivery system. HDL transports cholesterol (>80% as present as cholesteryl esters, CE) from atherosclerotic plaque-associated macrophage foam cell to the liver by the process named as Reverse Cholesterol Transport (RCT) for subsequent conversion to bile acids and final elimination in bile/feces. Earlier studies demonstrated the anti-atherogenic effect of increased intra-hepatic hydrolysis of CE by increasing the expression of CEH. Gal-G5 is developed as a hepatocyte-specific gene delivery system where galactose facilitates ASGPR-mediated endocytosis and CEH expression vector delivered as Gal-G5/CEH complex increases the CEH expression in hepatocyte. The over-expressed CEH would enhance the hydrolysis of HDL-derived CE into free cholesterol (FC) that is either directly secreted into bile or following conversion to bile acids thus accelerating the final elimination of cholesterol from the body—a process central to regression of existing atherosclerotic plaques.

With these concepts in mind, PAMAM dendrimer generation 5 (G5) was used to design a hepatocyte-specific delivery system for CEH expression vector so as to enhance the expression of CEH and increase final elimination of cholesterol with the long-term goal of developing a nanoparticle based gene delivery approach to regressing the existing atherosclerotic plaques. Taking advantage of hepatocyte-specific expression of asialoglycoprotein receptor (ASGPR) and the strong affinity of this receptor for galactose,[23, 37-39] G5 was decorated with large PEG chain (35K)-conjugated galactose (Gal) to form Gal-G5 (schematically presented in FIG. 12), where a large PEG spacer reduces the toxicity from the enormous G5 surface cations. In this example, data are presented to not only demonstrate specific uptake of Gal-G5 by primary hepatocytes in vitro and liver in vivo, but also the ability of Gal-G5 to deliver CEH expression vector and increase the flux of HDL-delivered CE to FC and subsequently to bile acids.

Results and Discussion

Synthesis and Characterization of Galactose-Modified Dendrimer

Figure 13A:
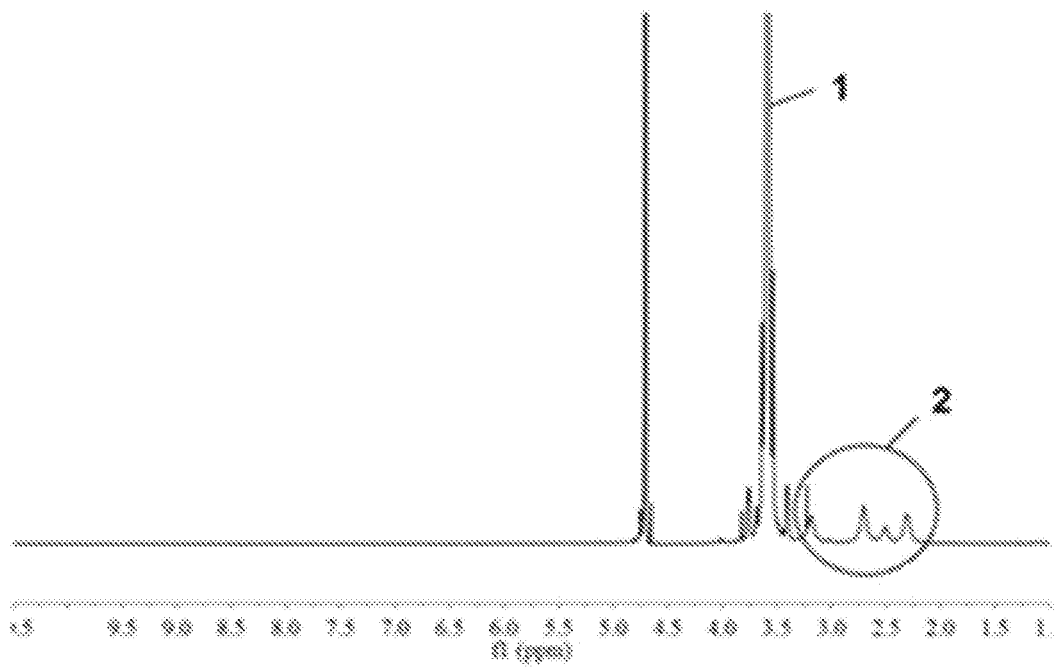
FIG. 13A-13D. In vitro physiochemical characterizations.

Gal-G5 was successfully synthesized by directly conjugating the Gal-PEG-NHS with the surface amine groups of PAMAM G5 via NHS ester reaction chemistry and 1H NMR was used to check the purity and conjugation of galactose-modified dendrimer. The spectrum (FIG. 13A) shows that the final product had relatively high purity without interfering proton peaks from reactants, intermediates, or reaction solvent. The methylene protons of branching units within the dendrimer had multiple peaks between 2.2 and 3.4 ppm. The repeat units of PEG from Gal-PEG-NHS had a single peak at 3.6 ppm. According to the integration of each peak, an average of 11 PEG chains was conjugated to G5.

Figure 13B:
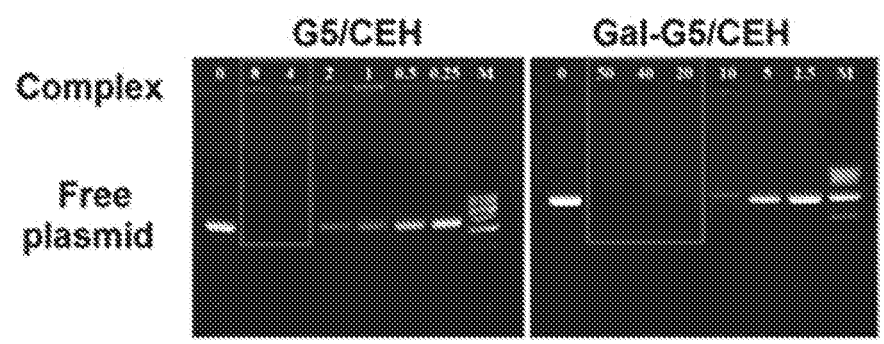

Agarose gel retardation assay was used to check the formation of dendrimers/gene complex. As shown in the FIG. 13B, the complex of G5/CEH plasmid could be formed at a weight ratio of 4 or higher. While at a weight ratio of 20 or higher, the CEH plasmid could be completely encapsulated by Gal-G5 (shown in the red bracket), suggesting the large PEG spacer from galactose modification significantly shield the cations on the surface of G5 (decreased from 30 mV for G5 to only around 2 mV for Gal-G5) but still could efficiently compact gene.

Figure 13C:
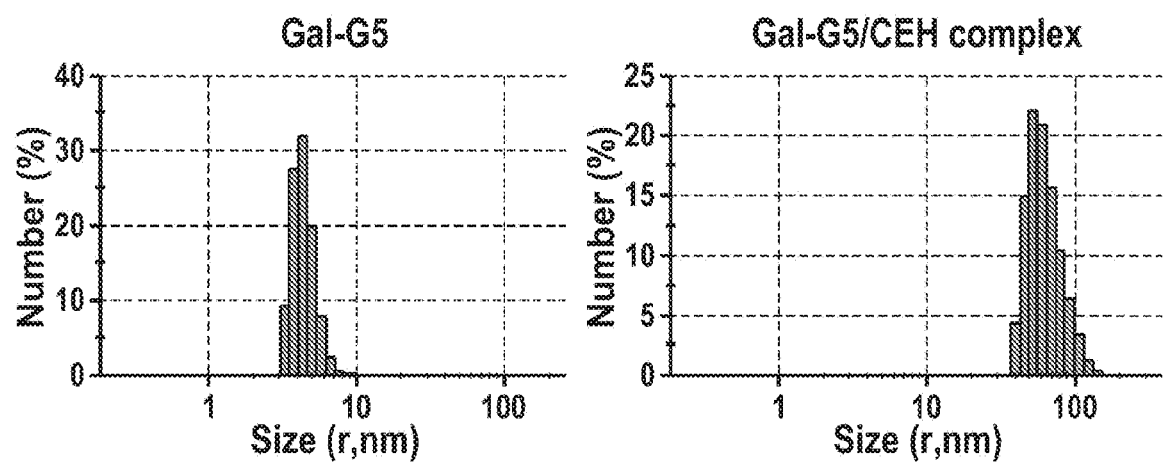
Figure 13D:
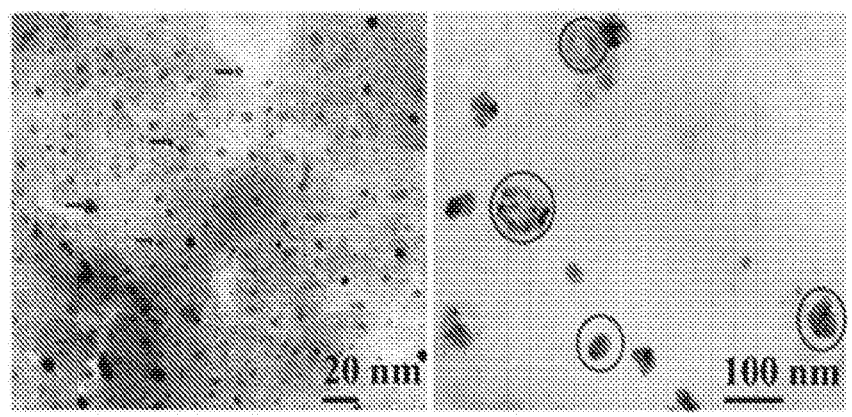

Dynamic light scattering (DLS) results (FIG. 13C) showed that after complex formation, the size significantly increased (from ~10 nm for Gal-G5 to 114.9 nm for Gal-G5/CEH complex). The successful formation of Gal-G5/CEH complex (FIG. 13D) was also confirmed by transmission electron microscopy (TEM). The sizes of Gal-G5 and Gal-G5/CEH complex were slightly smaller than hydrodynamic diameter from DLS probably due to the shrunk nanoparticles during the drying of the copper grid.

Galactose-Functionalization of G5 Reduces Toxicity in Primary Mouse Hepatocyte

Figure 14A:
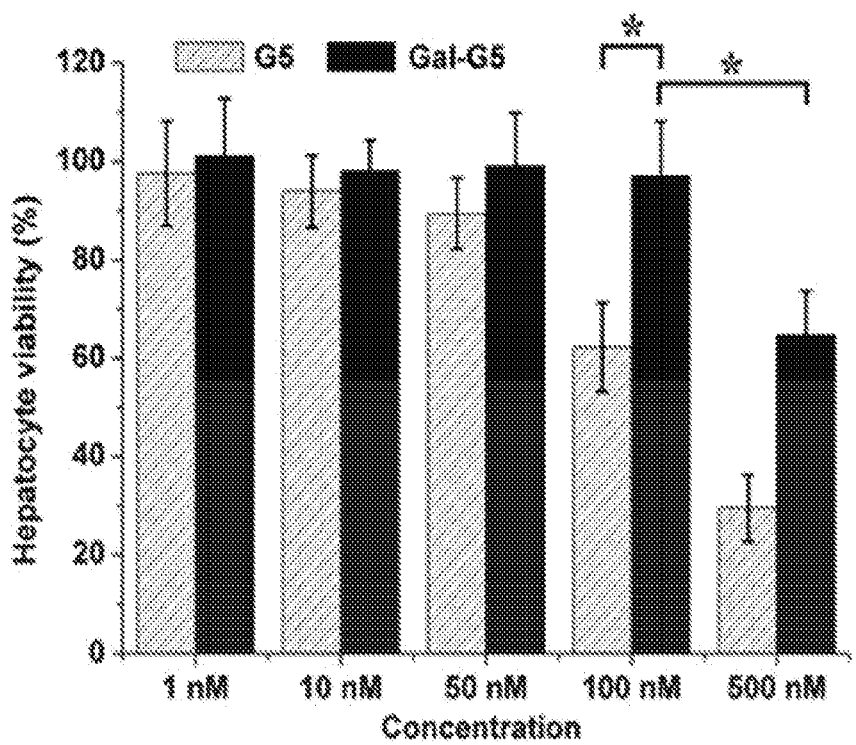
FIG. 14A-14B. Gal-G5 is not toxic to hepatocytes. Primary mouse hepatocytes were treated with different concentration of Gal-G5 and G5 for 24 h at the indicated concentrations and then assessed with WST-1 to determine their viability as described under "Methods".
Figure 14B:
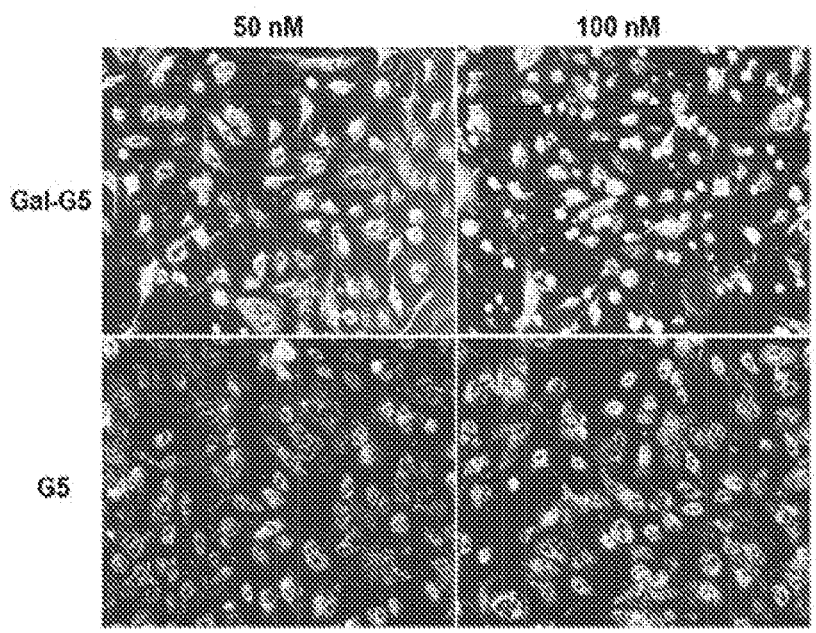

Cell proliferation reagent WST-1 was used to assess cytotoxicity of G5 after galactose modification. Significant toxicity was seen with G5 at 50 nM. In contrast, no toxicity was seen in cells exposed to 100 nM Gal-G5; significant decrease in viability was only seen at 500 nM Gal-G5 (FIG. 14A). Cellular toxicity was further confirmed by direct morphology assessment and as shown in FIG. 14B, no apparent change in cellular morphology was noted in hepatocytes exposed to Gal-G5 at either 50 or 100 nM. Consistent with WST-1 assay, multiple detached round dead hepatocytes without normal microstructure (shown in the red circles) were visible when exposed to G5 at both 50 and 100 nM concentrations. These data indicate that galactose functionalization of G5 has significantly improved the biocompatibility compared with unmodified G5 and this is likely due to the effective shielding of most of positive charges on the surface of G5 by PEG chains introduced in Gal-G5. Similar effects on toxicity by shielding of surface positive charges of G5 or other PAMAM dendrimers has also been reported[40-41].

Figure 15A:
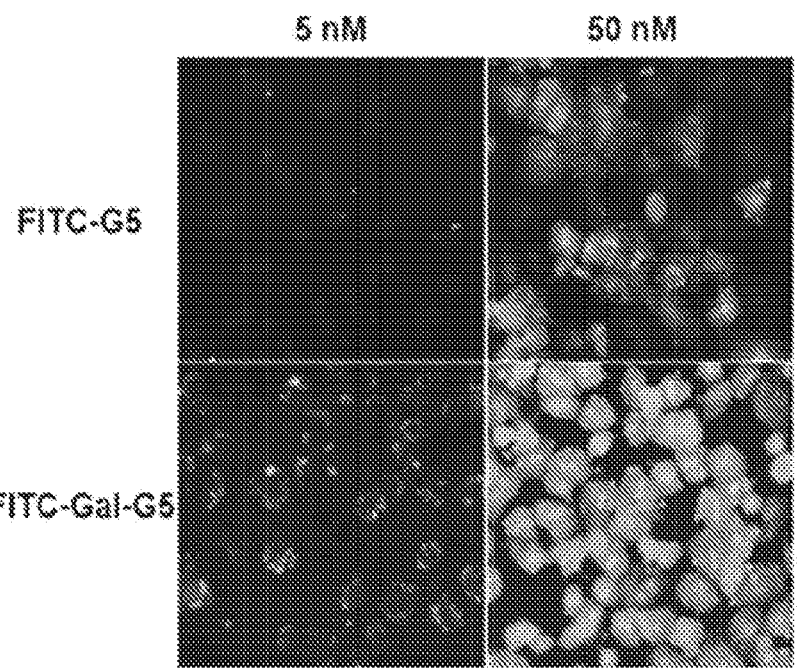
FIG. 15A-15D. Concentration and time dependent increase in uptake of Gal-G5 by hepatocytes. Primary mouse hepatocytes were exposed to FITC-Gal-G5 or FITC-G5 and uptake monitored by fluorescent imaging as described under "Methods".
Figure 15B:
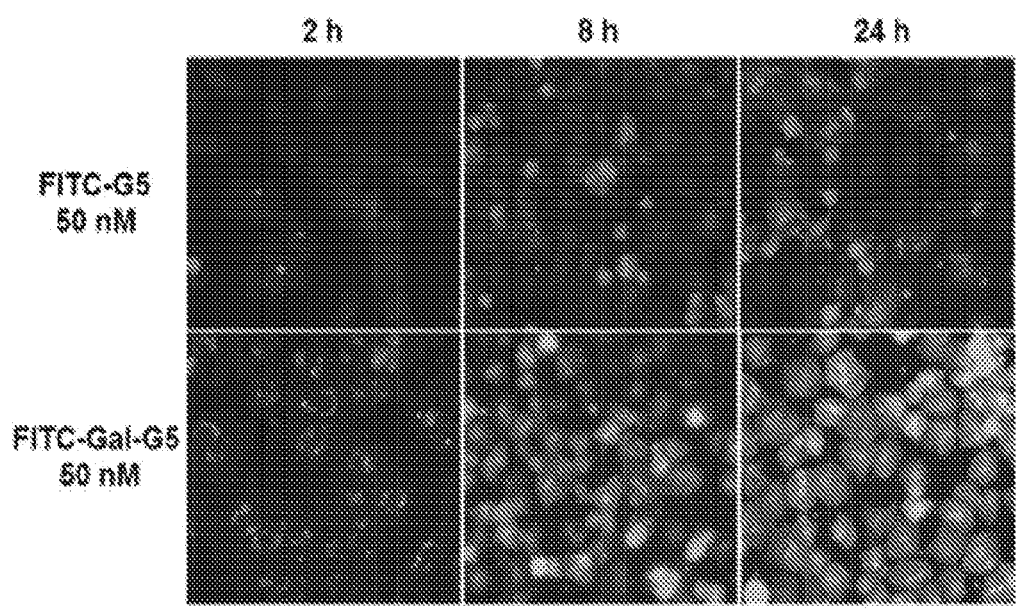
Figure 15C:
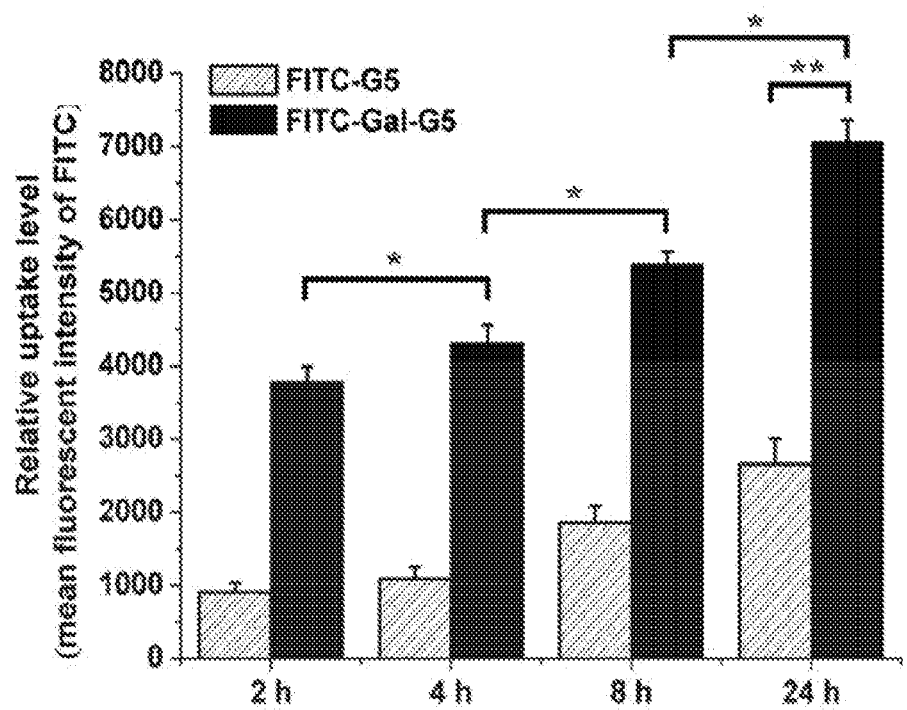

Concentration/Time Dependent-Uptake of Gal-G5 by Hepatocytes, Reduced Uptake of Gal-G5 by Macrophage and Competitively Inhibitory Hepatocytes Uptake of Gal-G5 by Exogenous Galactose Uptake of FITC-G5 or FITC-Gal-G5 by primary hepatocytes was monitored by fluorescent imaging and as shown in the FIG. 15A-15B, a concentration dependent (FIG. 15A) and time dependent (FIG. 15B) increase in internalization was observed. Consistent with galactose functionalization, higher uptake was seen with FITC-Gal-G5 than FITC-G5 at all concentrations and time points tested. Using optimum concentration of 50 nM, time dependent uptake of FITC-G5 or FITC-Gal-G5 was quantified using Flow cytometry analysis and consistent with the imaging data, higher uptake (measured as the Mean Fluorescent Intensity) was observed with hepatocytes exposed to FITC-Gal-G5 compared to FITC-G5; mean fluorescent intensity of FITC-Gal-G5 was around 6995±297.2 but only 664.6±48.62 of FITC-G5 at 50 nM after 24 h incubation, P<0.01 (FIG. 15C).

Figure 15D:
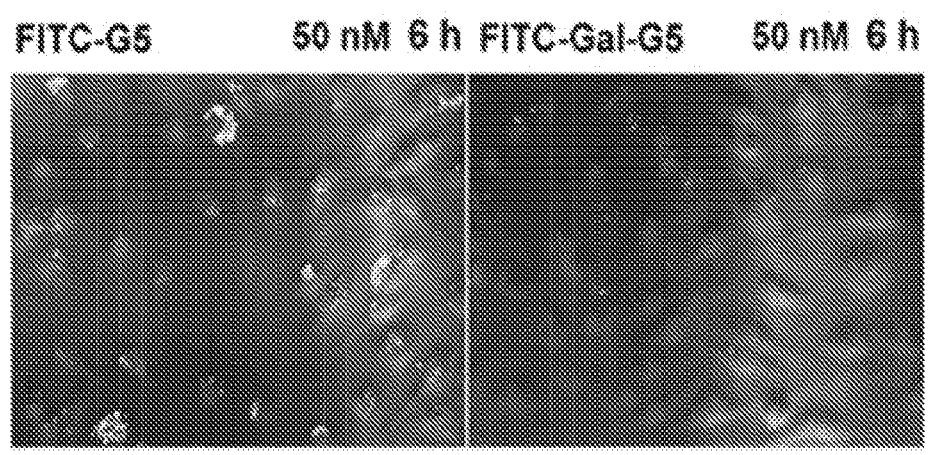

Additionally, in order to investigate the effect of galactose modification on the uptake of G5 by macrophage. Mouse peritoneal macrophage was selected as the one of the most aggressive scavenger. The results showed that Gal-G5 could significantly inhibit the uptake by macrophage after 6 h incubation in comparison to the unmodified G5 (shown in the FIG. 15D). The probably reasons are as follow: the galactose receptor ASGPR expression is relatively low in the macrophage; PEGylation of Gal-G5 prevents the dendrimer-based nanoparticle from agglomeration, decrease the highly positive charger on the surface of dendrimer and increases the high steric exclusion, thus hindering the uptake by macrophages in the reticuloendothelial system (RES).[42-45]

Figure 16A:
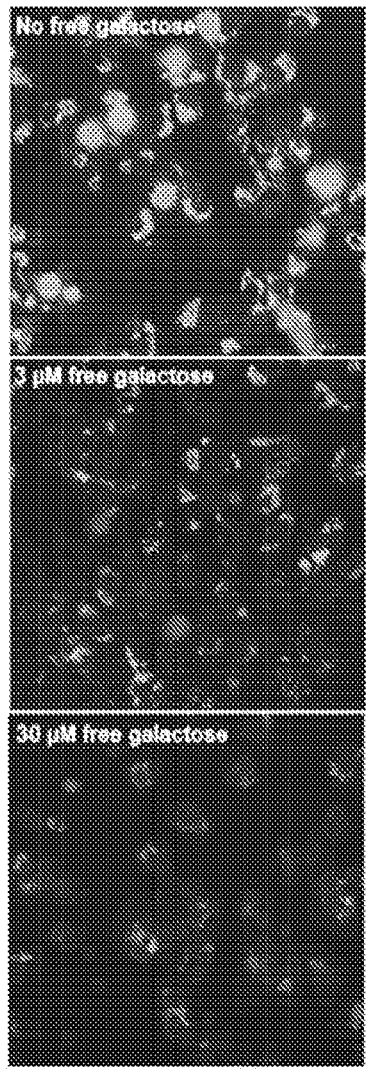
FIG. 16A-16B. Specific uptake of Gal-G5 by hepatocytes. Inhibition by exogenous galactose. To assess Galactose-mediated receptor endocytosis of Gal-G5, uptake of FITC-Gal-G5 was monitored in the presence of increasing concentrations (3 µM or 30 µM) of exogenous Galactose. Freshly isolated mouse hepatocytes were pre-incubated with free galactose at 37° C. for 30 min, and then incubated with 50 nM Gal-G5 for 2 h. Uptake of FITC-Gal-G5 was monitored by fluorescent microscopy (FIG. 16A) and quantified by FACS (FIG. 16B). Mean Fluorescence Intensity was determined and data are shown as Mean±SD, n=3. *P<0.05 and **P<0.01.
Figure 16B:
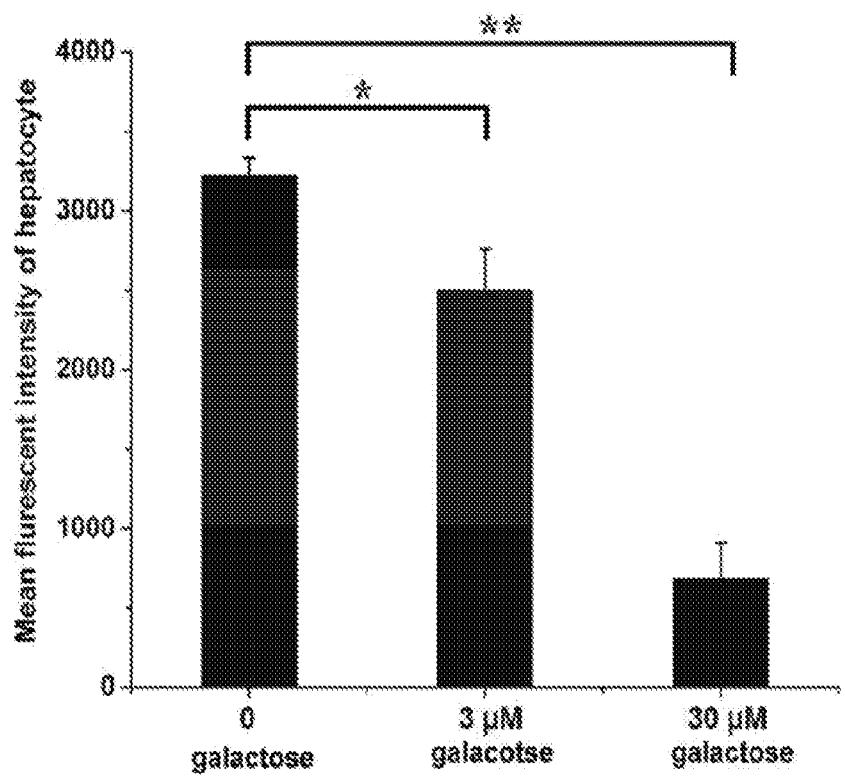

Specificity of FITC-Gal-G5 uptake via ASGPR was examined by monitoring the uptake in the presence of exogenous free galactose to compete for binding to the receptor. As shown in FIG. 16A, uptake of FITC-Gal-G5 was reduced in the presence of free galactose. Flow cytometry was used to quantify the uptake and Mean Fluorescence Intensities are shown in FIG. 16B. Compared to the uptake observed in the absence of galactose, significantly lower uptake was seen in the presence of 3 μM (24.2% decrease, P<0.05) or 30 μM (76.9% decrease, P<0.01) galactose. These data clearly demonstrate that the galactose functionalization of G5 effectively increased the uptake by hepatocyte in comparison to G5 mainly through the ASGPR that has a high affinity for galactose. Those results confirmed that the enhanced uptake of FITC-Gal-G5 by hepatocyte resulted from specific interaction between the galactose moiety of FITC-Gal-G5 and ASGPR expressed on the surface of hepatocyte. The free galactose selectively suppressed bound to the receptors, hindered the approach of FITC-Gal-G5 and consequently suppressed the uptake by hepatocyte, which are consistent with other studies describing galactose-mediated increase in hepatocyte uptake of other nanoparticles.[46-48]

Figure 17A:
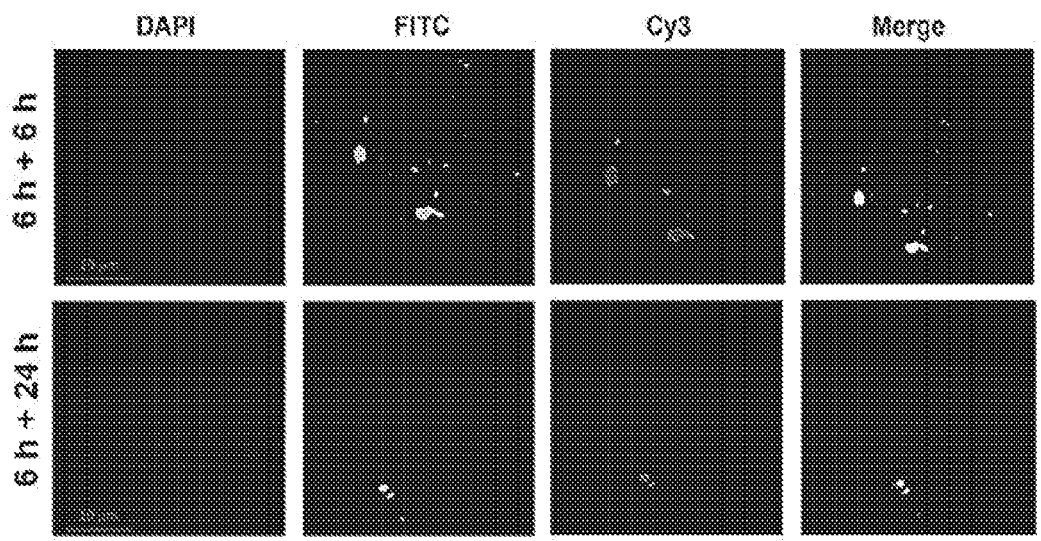
FIG. 17A-17B. CEH plasmid successfully separates from Gal-G5 complexes in mouse hepatocytes. Primary Mouse hepatocytes were treated with either FITC-G5/Cy3-plasmid complex (FIG. 17A) or FITC-Gal-G5/Cy3-plasmid complex (FIG. 17B) for 6 hours. The spent medium containing complexes were replaced by fresh whole William's E medium containing serum and hepatocytes were incubated for additional 6 h or 24 h. At the end of the incubation, the cells were rinsed with DPBS, nuclei stained by DAPI and imaged by laser scanning microscopy. Blue, DAPI; Green, FITC; Red, Cy3.
Figure 17B:
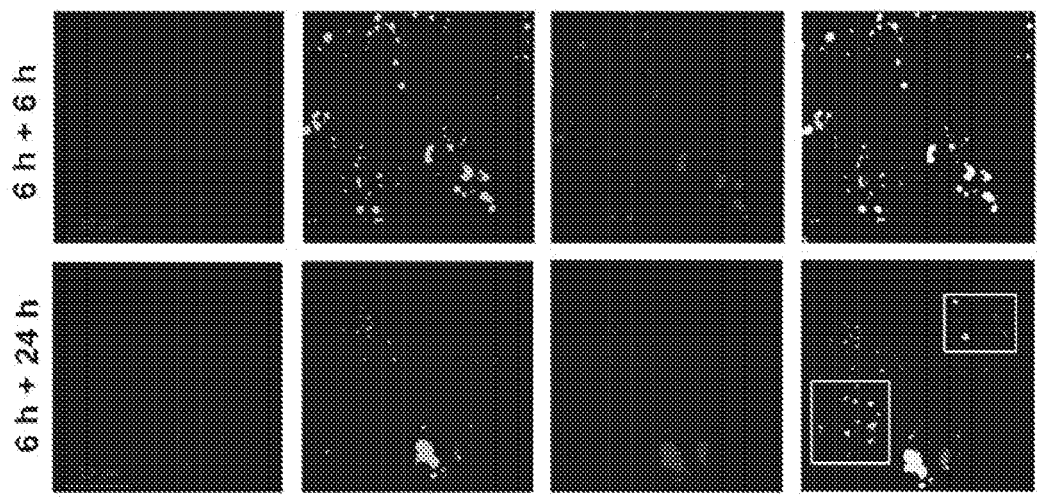

Successful Intracellular Dissociation of Plasmid DNA from Gal-G5/Plasmid Complexes Effective dissociation and subsequent movement of vector/DNA to the nucleus is critical for expression of the delivered gene. Gal-G5/Cy3-labeled plasmid complex was used to monitor intracellular localization and dissociation. After 6 h, Cy3-plasmid was tightly complexed with both vectors. Dissociation of Cy3-plasmid from FITC-Gal-G5 became evident at 24 h, while no appreciable dissociation of Cy3-plasmid and FITC-G5 was observed (FIG. 17, dissociations are shown in the small boxes, stating more separation of green and red dye). This phenomenon was possibly caused by the compressive force between dendrimer and plasmid which could be weakened by large PEG spacer on the surface of Gal-G5 and released plasmid could further translocate into nucleus for transcription and translation. Those observations are consistent with facilitated gene transfection delivered by PEGylated-PAMAM dendrimer reported by the other researchers.[49-50]

Figure 18A:
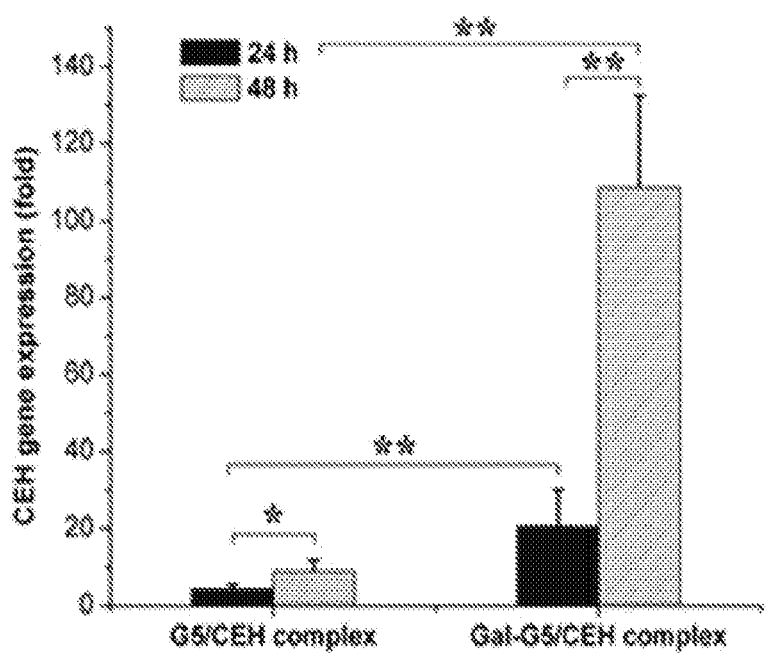
FIG. 18A-18C. Delivery of CEH plasmid via Gal-G5 results in increased CEH expression and associated biological activity.

Gal-G5 Delivered CEH Expression Vector Leads to CEH mRNA Expression and Increased CEH Activity in Hepatocyte To directly examine whether galactose functionalization indeed increases the ability of Gal-G5 to deliver CEH expression vector to hepatocytes in vitro, CEH mRNA expression was quantified by using RT-PCR following incubation with either G5/CEH or Gal-G5/CEH complexes. CEH expression vector where CEH expression was driven by a constitutive CMV promoter was used along with empty vector pCMV serving as a control. Fold increase in CEH mRNA expression was determined relative to the expression observed in hepatocytes treated with G5/CEH. It should be noted that no Ct value was obtained when RNA from hepatocytes treated with G5/pCMV or Gal-G5/pCMV complexes. As shown in FIG. 18A, expression of CEH delivered by Gal-G5 was about 2 and 6 times fold than that by G5 (P<0.01) after 24 h and 48 h of exposure, respectively.

Figure 18B:
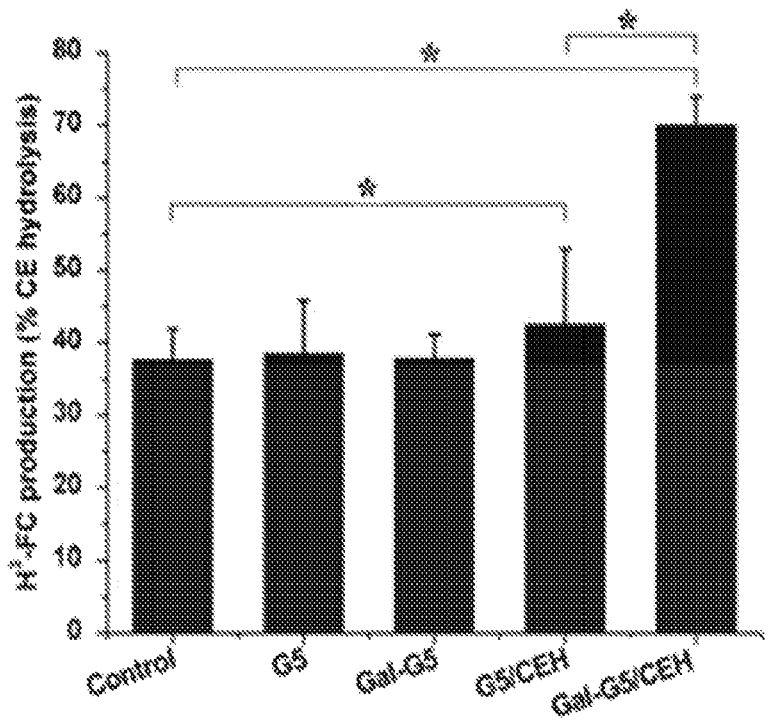
Figure 18C:
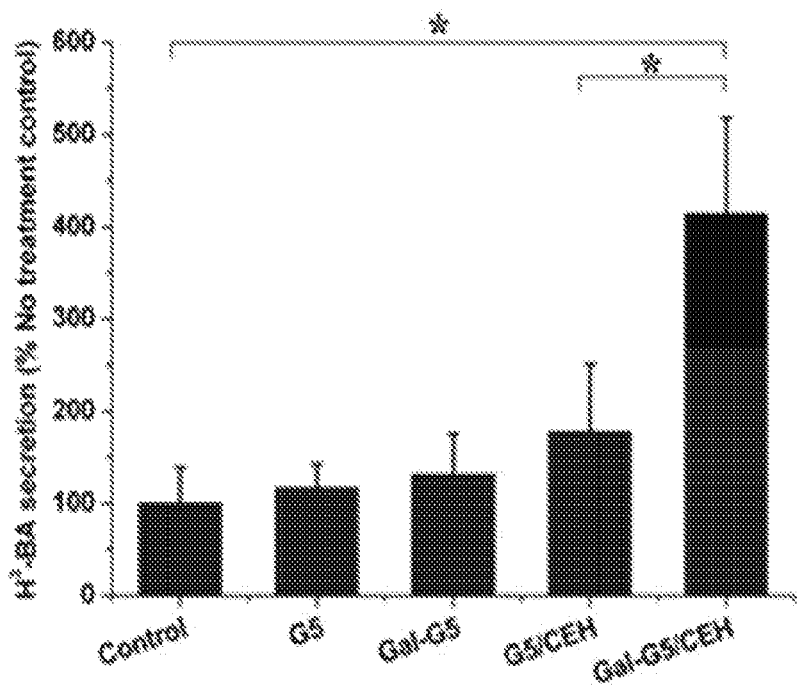

It was earlier demonstrated that an increase in hepatic CEH not only leads to increase in the hydrolysis of HDL-CE but also increases the flux of cholesterol from HDL-CE to bile acids providing the mechanism underlying the anti-atherosclerotic effects of hepatic CEH. The objective of developing a non-viral platform for targeted delivery of CEH to the liver is to establish a novel anti-atherosclerotic strategy. It is thus critical to establish that Gal-G5 delivered CEH is biologically active or functional. To examine whether increased CEH mRNA expression leads to increase in intracellular CE hydrolysis, conversion of HDL-[$^3$H]-CE to [$^3$H]-FC and final conversion of [$^3$H]-FC to [$^3$H]-BA was monitored. Consistent with the increased CEH mRNA expression, compared to hepatocytes exposed to G5/CEH, significantly higher hydrolysis of HDL-CE was noted in hepatocytes exposed to Gal-G5/CEH complexes (FIG. 18B; 69.97±3.94% versus only 38.46±7.44%, P<0.05). Furthermore, increased conversion of HDL-CE derived FC to bile acids was also noted in hepatocytes treated with Gal-G5/CEH complexes (FIG. 18C, 417±99.09% versus 182.12±62.54, P<0.05). Consistent with earlier data,[10,13,51] showing increased conversion of HDL-CE to BA following CEH overexpression in hepatocyte, these data confirm that Gal-G5-mediated delivery of CEH gene leads to the elimination of HDL-derived CE to BA.

Liver-Specific CEH Gene Delivery In Vivo Using Gal-G5/CEH Complex

Figure 19A:
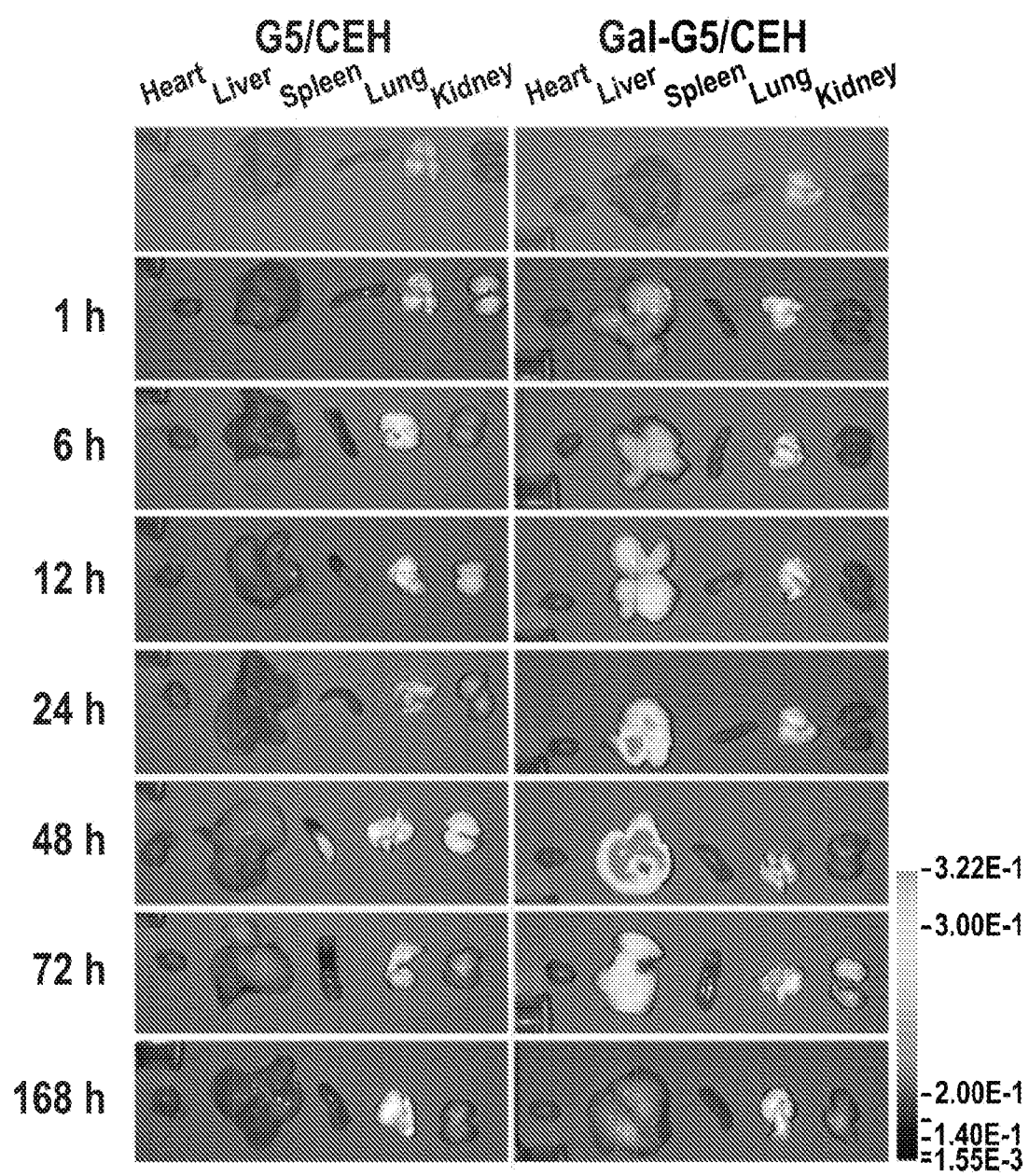
FIG. 19A-19B. Liver-specific uptake of Gal-G5 in vivo. C57BL/6 mice were injected (i.v.) with 800CW-labeled Gal-G5/CEH complex or 800CW-label G5/CEH as described under "Methods".

For establishing the validity of galactose functionalized G5 as a platform for delivery of CEH or any other expression vector to liver to modulate in vivo expression, it is important to not only demonstrate selective uptake by liver but also show that such a delivery does not induce toxicity. For this purpose, time-dependent in vivo bio-distribution of Gal-G5/CEH and G5/CEH complexes was monitored after intravenous injection. FIG. 19A shows that Gal-G5/CEH complex rapidly targeted liver after 1 h intravenous administration, gradually accumulated with highest intensity in liver seen after 48 h and the infrared dye 800CW intensity persisted at least 7 days post-administration. This higher liver accumulation of Gal-G5/CEH complex in comparison to the G5/CEH complex was consistent with higher hepatocyte uptake described before, which validated the liver-specific property from galactose modification. Meanwhile, compared to G5/CEH complex, PEG modifications from galactose also resulted in a decrease of the passive RES uptake by spleen and renal clearance, which was probably due to that PEGylation are well known to be biocompatible, non-immunogenic, to increase the blood circulation time after intravenous injection by reducing opsonization by proteins and hindering the uptake by macrophages in the RES. While similar accumulation in RES organs (liver and spleen) was observed in mice-administrated by G5/CEH complex. The accumulation in the kidney for both kinds of complex is likely due to filtration and secretion of same size dendrimer (less than 10 nm) after dissociation of complex, but the fluorescent signal in kidney from Gal-G5/CEH complex-treated group was much lower within the 48 h compared with the G5/CEH complex, which could be longer circulation in blood induced by PEGylation from Gal-G5/CEH. These data are not only consistent with in vitro observation shown above but also clearly demonstrated the ability of Gal-G5 to selectively deliver gene to the liver.

Figure 19B:
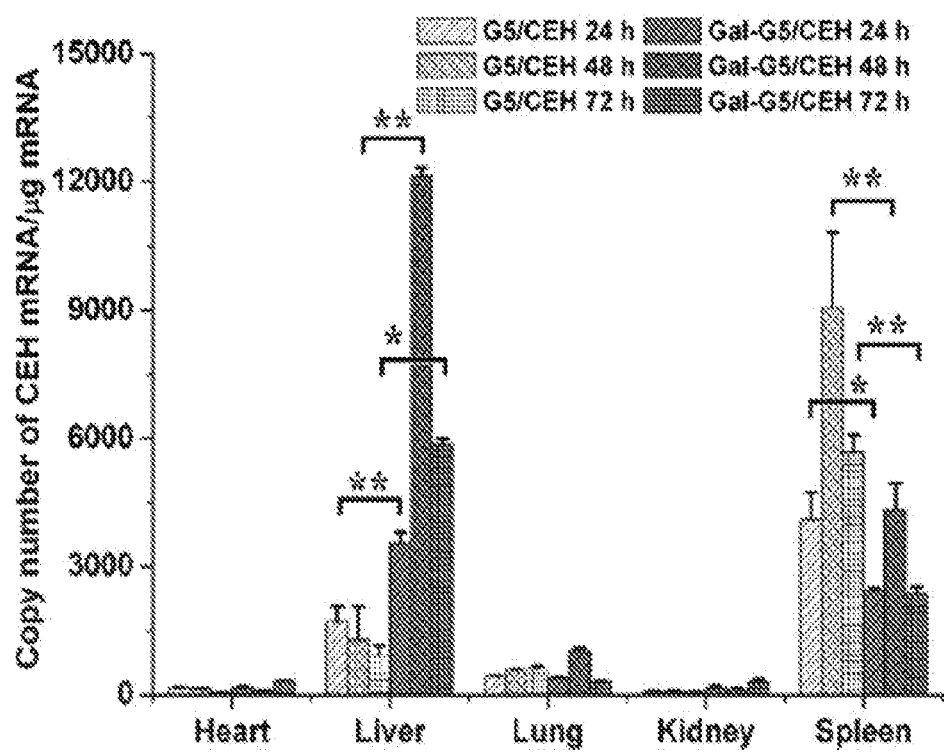

Consistently, in vivo CEH gene expression analysis (FIG. 19B) revealed that Gal-G5/CEH resulted in the much higher CEH expression (shown as copy number of CEH mRNA) in liver in comparison to the G5/CEH at all three time points. The highest CEH expression in liver was seen in the group-treated with Gal-G5/CEH at 48 h, which was around 3 fold ($P<0.01$) higher than G5/CEH group. Higher CEH expression in spleen was observed among the mice-treated with G5 CEH 48 h post-injection; the decrease in CEH copy number in liver at 72 h could be related to mRNA stability/degradation. CEH expression in other tissues such as heart, lung and kidney was very low for both complexes possibly due to very limited uptake of these complexes by these tissues. While the Gal-G5/CEH complexes mediated increase in CEH expression seen here is 10 fold lower than the transient adenovirus-mediated CEH expression in liver previously achieved (~$5\times10^6$ copies/µg total RNA),[51] only a two fold increase in CEH activity in liver-specific CEH transgenic mice was sufficient to attenuate diet-induced atherosclerosis in LDLR-/- mice. Therefore, this non-viral gene delivery carrier is a novel alternative with safe application, low cost and simple construction.

Figure 20:
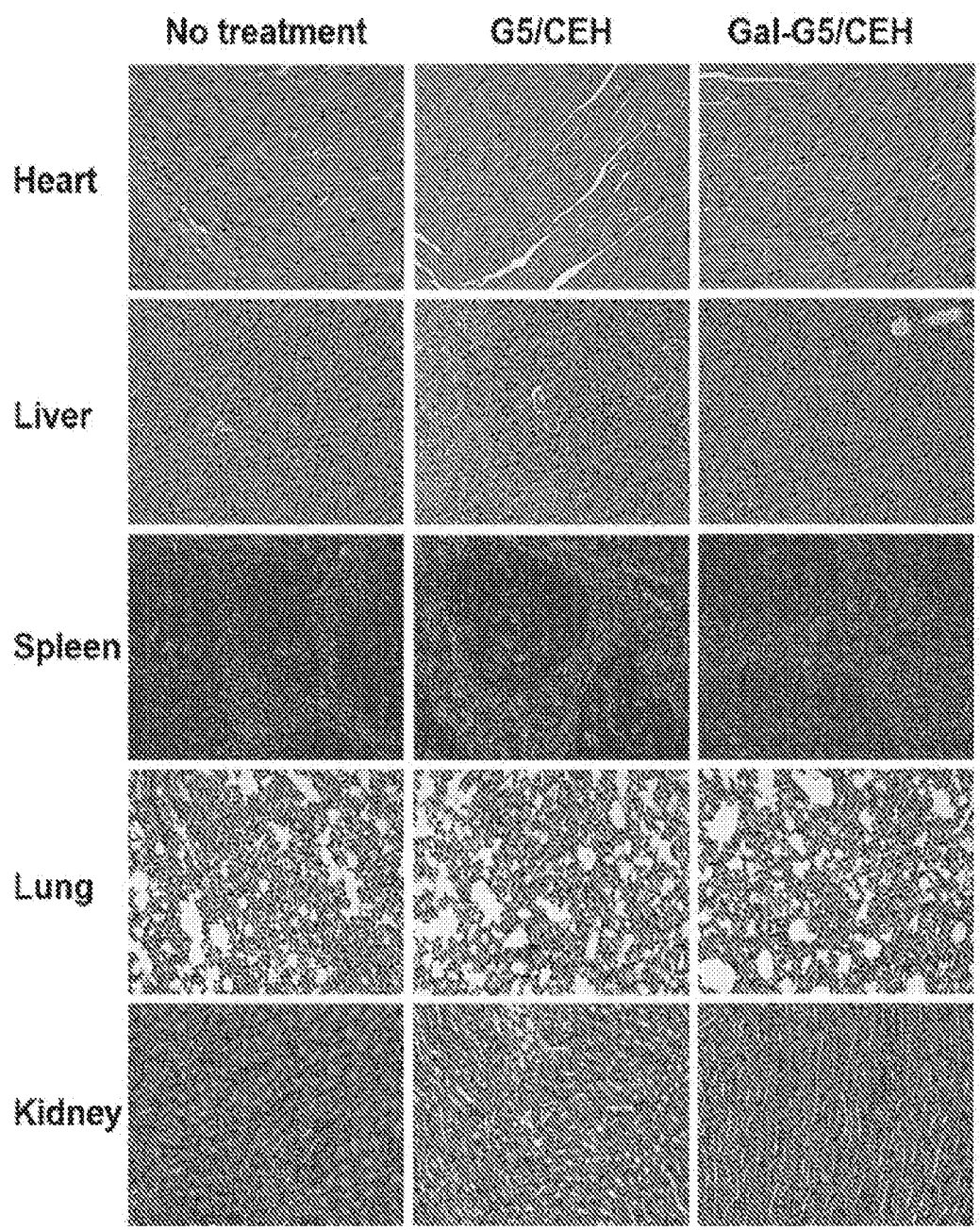
FIG. 20. In vivo delivery of CEH using Gal-G5 does not result in tissue toxicity. C57BL/6 mice were injected (i.v.) with indicated complexes and tissues were harvested after 24 h. H&E-stained sections of major organs are shown. Scale bar: 20 µm.

In Vivo Delivery of Gal-G5/CEH Complexes do not Induce Hepatic or Renal Toxicity Systemic toxicity and inflammatory reaction was investigated 24 h after intravenous administration to examine the biocompatibility of two kinds of complexes. There were no significant histological differences between the major organs of treated and untreated mice (FIG. 20). Plasma levels of alanine transaminase (ALT) and aspartate transaminase (AST) for liver toxicity, blood urea nitrogen (BUN) for kidney toxicity and TNF-α and IL-6 for induction of inflammatory reaction were determined and the data are shown in the Table 1.

However, the PEG spacer between galactose and G5 greatly shielded the exposure of amino groups to the tissues, thus reducing the potential toxicity of highly positive charge.[44-45]

Conclusion

Inhibition of pathological processes central to the development of disease, by pharmacologically active small molecules[52-53] or genetic manipulation by siRNA/miRNA/ASOs[54-55], is the most widely accepted/used strategy to reduce the progression of diseases. However, enhancing an endogenous biological process that is necessary for the prevention of disease progression, and more importantly the reversal of established disease, has proven to be challenging mainly because of the lack of suitable platforms for the introduction of the critical gene required to increase the affected pathway. Viral vectors, though proven useful in pre-clinical animal studies, are invariably associated with undesirable immunological effects and/or toxicity. Based on the significant residual CVD risk present despite reaching the target LDL-C levels and failure of risk reduction by merely increasing HDL-C levels has shifted the paradigm from lipoprotein associated cholesterol to flux of cholesterol from arterial plaque associated macrophages to liver and final elimination from the body.[56] The fact that cholesterol is carried within the lipoproteins as CE but only FC is secreted in bile either directly or following conversion to bile acids underscores the importance of hepatic CE hydrolysis and earlier studies have established the anti-atherogenic role of hepatic CEH. Currently, endogenous regulation of CEH remains largely unknown in mice or humans although reduced CEH expression is reported in human carotid artery plaques.[4] With the objective to address the as yet unmet need for novel strategies for enhancing the removal of cholesterol from body, the data presented herein demonstrates the suitability of Gal-G5 to deliver CEH to the liver and increase the flux of cholesterol from HDL-CE to FC and bile acids by increasing CE hydrolysis within the hepatocytes. Furthermore, functionalization of G5 with galactose not only increases liver-specific delivery, but use of long PEG spacer for galactose attachment, also reduces the toxicity associated with high positive charges on the surface of unmodified G5. The development of this non-toxic and efficient liver-spe-

TABLE 1

Hematological markers of hepatic and renal toxicity as well as cytokine Induction in C57BL/6 mice after treatment with different kinds of complexes

|  | AST (U/L) | ALT (U/L) | BUN (mg/dL) | IL 6 (ng/mL) | TNF-α (ng/mL) |
| --- | --- | --- | --- | --- | --- |
| Mice without treatment | 64.7 ± 10.3 | 34.0 ± 3.5 | 22.3 ± 0.6 | 1.12 ± 0.10 | 0.55 ± 0.11 |
| Mice treated with G5/CEH complex | 315.2 ± 114.9* | 168.8 ± 81.8# | 27.4 ± 6.1 | 3.61 ± 0.20 | 0.73 ± 0.12 |
| Mice treated with Gal-G5/CEH complex | 70.8 ± 13.2 | 37.0 ± 8.2 | 25.8 ± 5.6 | 1.63 ± 0.05 | 0.50 ± 0.05 |

Mean (n = 3),
*P < 0.01 and
P < 0.01.

No significant difference in these parameters was seen in mice treated with Gal-G5/CEH in comparison to the untreated mice but significant increase for ALT, AST and IL-6 was observed in mice treated with G5/CEH. These results suggested the high number of positively charged amino groups on the surface of G5 could lead to some toxicity to tissues especially for metabolically active liver.

cific gene delivery platform can be used for enhancing removal of cholesterol from the body to reduce the existing atherosclerotic plaque burden (or plaque regression) for which no therapeutics are currently available. It is noteworthy that hepatocyte-specific CEH over-expression significantly attenuates western diet-induced atherosclerosis without having any effect on plasma lipoprotein profile.[51]

Methods

Materials

Ethylenediamine (EDA) core-polyamidoamine (PAMAM) dendrimer generation 5.0 (technical grade) was purchased from Dendritech (Midland, Mich.). Fluorescein isothiocyanate (FITC) and D-(+)-Galactose were purchased from Sigma-Aldrich® (St. Louis, Mo.). 800CW-NHS ester was obtained from Li-COR® Biotechnology (Lincoln, Nebr.). Galactose-PEG-NHS (MW 35,000) was customized from JenKem® Technology (Plano, Tex., USA). SnakeSkin™ dialysis tubing with 7,000 molecular weight cut-off (MWCO) was purchased from Thermo Scientific™ (Rockford, Ill.). WST-1 reagent was purchased from Roche Applied Science (Grand Island, N.Y.). Collagenase type I was obtained from Worthington Biochemical Corp. William's E medium, fetal bovine serum (FBS) and Dulbecco's Phosphate-buffered saline (DPBS) were obtained from Gibco™ BRL (Carlsbad, Calif., USA). Trypsin-EDTA (0.25%), streptomycin and penicillin were obtained from Invitrogen Co., USA. Label IT Cy3 control plasmid was purchased from Mirus Bio (Madison, Wis.). VECTASHIELD® mounting media were purchased from Vector® Laboratories (Burlingame, Calif.). RNeasy® Mini Kit was purchased from QIAGEN GmbH. High Capacity cDNA Reverse Transcription Kit and TaqMan™ Universal PCR Master Mix, no AmpErase™ UNG were obtained from Applied Biosystems™. Human macrophage CEH plasmid (Accession No. AY268104) was constructed and characterized previously.[57] All other chemicals were purchased from Sigma-Aldrich® (St. Louis, Mo.).

Animals

Six-week-old C57BL/6 mice (22±3 g weight, both genders) obtained from the Jackson Laboratory were used for all experiments here. All mice were kept in pathogen-free conditions with 12 h dark/light cycle. All procedures were approved by the Virginia Commonwealth University Institutional Animal Care and Use Committee.

Isolation and Culture of Primary Mouse Hepatocyte

Primary mouse hepatocytes were freshly isolated by collagenase-perfusion technique as described previously.[58] Hepatocytes were plated at collagen-coated well/dish in the William's E medium supplemented with heat-inactivated FBS (20%), insulin (1.5 µM), streptomycin (100 U/mL) and penicillin (100 U/mL). The spent media was replaced after 3 h prior to any treatment. Hepatocytes were maintained at ~90% confluence throughout the experiments.

Synthesis of Galactose-Modified Dendrimer

Fifteen mg of G5 dendrimer was dissolved in 0.1 M pH 8.3-8.5 sodium bicarbonate solution (10 mL) and 200 mg NHS-PEG-Galactose (molar ratio of $NH_2$-PEG-Galactose to G5 was around 15:1) was added to the dendrimer solution. The mixture solution was stirred overnight at room temperature, dialyzed and lyophilized. To monitor intracellular uptake and tracking, FITC was coupled to Gal-G5 or G5 as described before.[59] To assess in-vivo liver targeting, IRDye® 800CW NHS ester was coupled to the Gal-G5 or G5 via stable amide bonds. Briefly, 30 mg of Gal-G5 or 3 mg of G5 was dissolved in 2 mL of 0.1 M sodium bicarbonate solution (pH 8.3-8.5 and 0.2 mg of 800CW NHS ester (1 mg/mL in sodium bicarbonate solution) was added dropwise into Gal-G5/G5 solution. The reaction mixture was stirred overnight at room temperature and dialyzed against distilled water using a cellulose membrane (MWCO 7 kDa) for 2 days. The blue solution was lyophilized to obtain 800CW-labeled Gal-G5/G5.

Characterizations of Gal-G5

$^1H$ NMR spectra were recorded on a Varian superconducting fourier-transform NMR spectrometer (Mercury-300).[26] $D_2O$ was used as the solvent. The $^1H$ chemical shift of $D_2O$ residue is 4.8 ppm. The hydrodynamic diameter and zeta potential of galactose-modified dendrimer were determined at room temperature using a dynamic light scattering analyzer (Zetasizer Nano, Malvern, UK). To visualize the morphology of galactose-modified dendrimer, the dendrimer suspension was dropped onto a 300 mesh carbon coated copper grid and dried on a filter paper at room temperature. The grid was then observed in a transmission electron microscope (TEM, JEM-3010, ZEOL, Tokyo, Japan).

Preparation of Dendrimers/siRNA Complexes

Five hundred ng of CEH plasmid and the calculated amount of Gal-G5/G5 were diluted in 50 µL of pH 7.4 PBS buffer (100 mM), respectively. The polymer solution was added to the CEH plasmid solution, rapidly mixed by pipetting up and down (at least five times), and incubated for 30-40 min at RT in order to obtain the complexes.

Agarose Gel Retardation Assay

To evaluate DNA-dendrimer complex formation, electrophoretic mobility shift assays were used. Twenty µL of Gal-G5 or G5 together with 0.5 µg CEH plasmid at different weight ratios were vortexed for 30 s and kept at room temperature for additional 30 min. The mixtures were gently mixed with 4 µL 6×DNA loading buffer and resolved on a 1% agarose-gel (at 100V in Tris-acetate-EDTA buffer) containing 0.3 µg/mL ethidium bromide. Ethidium bromide stained DNA bands were visualized by UV-light system.

Cytotoxicity of Gal-G5/G5 to Primary Mouse Hepatocyte

Primary mouse hepatocytes (n=6) cells were seeded in 96-well collagen-coated culture plates (Corning—Coaster, Tokyo, Japan) at a density of 5×104 cells/well and cultured overnight. Hepatocytes were then incubated with increasing concentrations of Gal-G5 or G5 (1 nM to 500 nM, diluted in DMEM containing 0.5% FBS) for 24 h, then washed by DPBS thrice and subjected to WST-1 assay. Additionally, hepatocytes with different treatments were imaged under a (200×) magnification to assess morphological changes.

Concentration-Dependent and Time-Dependent Uptake

Primary mouse hepatocytes were seeded in collagencoated four chamber slides, cultured with William's E medium to attach overnight and then incubated with indicated concentrations of FITC-G5 or FITC-Gal-G5 for various time points. At the end of each treatment, cells were washed with PBS, fixed with 4% formaldehyde at room temperature for 20 min, permeabilized with 0.1% Triton X-100® for 5 min, and the cell nuclei were counterstained with DAPI for 5 min. Cellular uptake was assessed by fluorescent imaging, a 405 nm laser line was selected for DAPI, and a 488 nm laser line was selected for FITC.

Quantitative Determination of Uptake by Flow Cytometry

Primary mouse hepatocytes were seeded in the collagen-coated 60-mm dishes and allowed to attach overnight[60]. The spent medium was removed and the cells were washed with PBS once. The cells were then incubated with 50 nM FITC-Gal-G5 or FITC-G5 for 2 h, 4 h, 8 h and 24 h. At the end of the incubation, hepatocytes were collected and cell-associated FITC analyzed by Canto-BD FACSCanto™ II Analyzer (BD, USA) and the mean fluorescence intensity (MFI) analyzed using FlowJO™ software.

Competitive Inhibition of Uptake by Free Galactose

Primary mouse hepatocytes were seeded in 4-chamber slides, cultured overnight and then incubated with 3 µM or 30 µM free galactose for 30 min followed addition of 50 nM FITC-Gal-G5. After 2 h, the cells were counterstained with DAPI and imaged by fluorescent microscopy. A parallel set of cells were collected for quantitative analysis by flow cytometry as described above.

Intracellular Tracking of Gal-G5/Cy3 Labeled Plasmid

In order to visualize intracellular localization and dissociation of Gal-G5 or G5 and CEH plasmid in hepatocyte,[61] hepatocytes were seeded in 2-wells chamber slides and allowed to attach overnight. FITC-Gal-G5 or FITC-G5 was dissolved into 200 µL serum-free medium, while Cy3-labeled CEH plasmid was diluted into another 200 µL serum-free medium. All the above solutions were mixed by vortex for 30 s and then equilibrated for 30 min at room temperature to obtain FITC-Gal-G5/plasmid complex or FITC-G5/plasmid complex. After removing the spent medium, these complexes were added and cells incubated at 37° C. for 6 h. The spent medium containing the complexes was replaced by fresh whole medium and cells were incubated for additional 6 h or 24 h, respectively. At the end of incubation, the cells were rinsed, fixed with 4% formaldehyde, permeated with 0.15% Triton X-100® and then counterstained with DAPI. The coverslips were mounted on the slides and imaged by Zeiss LSM 700 confocal laser scanning microscope using a magnification of 630×.

Transfection of Hepatocytes In Vitro

Primary mouse hepatocytes were seeded in 6-wells plate (n=3) and cultured overnight. 2 µg of pCMV plasmid and CEH plasmid were kept per each well. Gal-G5/p-CMV complex, Gal-G5/CEH complex, G5/p-CMV complex and G5/CEH complex were prepared similar to the previously described, respectively Hepatocytes were transfected with both complexes for 24 h and then replaced with fresh whole medium for further 24 h and 48 h incubation, respectively.

Expression of Transfected CEH

At the end of experiments, total RNA was extracted using an RNeasy® kit (Qiagen). cDNA was synthesized using a high capacity cDNA reverse transcription kit (Applied Biosystems™). Real time PCR was performed on a Stratagene Mx3000P machine, using TaqMan™ Universal PCR Master Mix and optimized probe and primer sets from Applied Biosystems™. The following optimized probes were used for CEH and β-actin (Housekeeping gene): CES1, Hs00275607_m1; Mouse ACTB, 4352341 E.[10]

Determination of Biological Activity of CEH

After 24 h of incubation with complexes, medium was replaced with fresh medium containing HDL-[$^3$H]-CE (80-100 µg protein and 1-1.5×10$^6$ dpm, HDL-[$^3$H]-CE was prepared as described previously[10]) along with ACAT inhibitor (CP118, 1.25 µg/mL) and incubation continued for additional 48 h. Conditioned medium was collected to extract [$^3$H]-BA. Cells were washed twice with PBS and total lipids were extracted and separated by thin layer chromatography using hexane:diethyl ether:acetic acid (90: 10:1, v/v) as the solvent system as described previously.[10, 58] Intracellular CEH activity was expressed as the amount of [$^3$H]-FC accumulated within the cells. Effect of increased CEH expression on flux of HDL-[$^3$H]-CE to bile acids was assessed by monitoring the release [$^3$H]-BA in the medium.

In Vivo Experiments

Tissue Distribution

To assess uptake of Gal-G5 by liver in vivo, IRDye® 800CW NHS Ester (LI-COR®) was coupled to the Gal-G5/G5 and 800CW-labeled Gal-G5/G5 CEH plasmid complexes (0.3 mg DNA/kg, 3 mice utilized for each group) were injected (i.v., 0.2 mL, balanced in osmolality with the addition of DPBS) into 6-week-old C57BL/6 female mice. For ex vivo imaging, the major organs (heart, liver, spleen, lung and kidney) were harvested at indicated time points and imaged using Odyssey® Fc Imaging System (Li-COR®, Nebraska USA) at ex/em=780/800 nm.[62-65]

In Vivo CEH Expression Delivered by Gal-G5/CEH Complex

Total RNA was prepared from ~30 mg of various tissues and CEH expression assessed by RT-qPCR. CEH copy number was determined using a standard curve method as described earlier[51].

Toxicity and Pathology Studies

Twenty-four hours after mice were treated with Gal-G5/CEH or G5/CEH complexes (n=3, 0.3 mg DNA/kg), blood was obtained from the mice via retro-orbital bleed, centrifuged at 5,000 g for 10 minutes at 4° C. and the serum analyzed for aspartate aminotransferase (AST), alanine aminotransferase (ALT) and blood Urea Nitrogen (BUN) to assess hepatic or renal toxicity. To assess immunotoxicity, serum IL-6 level and TNF-α were monitored by corresponding ELISA assay kits (BD Biosciences, San Diego, Calif.).[22-23] Tissues (heart, liver, spleen, lung, and kidney) were collected, fixed in 4% formaldehyde, paraffin embedded and sectioned for H&E staining. Images of tissue sections were collected using a Nikon light microscope (Nikon).

Statistical Analysis

Results were expressed as a mean±SD. Student's t-tests were used to evaluate statistical significance. A result of P<0.05 was considered to be statistically significant.

References cited in this example

1. D'Agostino, R. B.; Russell, M. W.; Huse, D. M.; Ellison, R. C.; Silbershatz, H.; Wilson, P. W.; Hartz, S. C., Primary and subsequent coronary risk appraisal: new results from the Framingham study. *American heart journal* 2000, 139 (2), 272-281.
2. Libby, P., Inflammation in atherosclerosis. *Arteriosclerosis, thrombosis, and vascular biology* 2012, 32 (9), 2045-2051.
3. Moore, K. J.; Sheedy, F. J.; Fisher, E. A., Macrophages in atherosclerosis: a dynamic balance. *Nature Reviews Immunology* 2013, 13 (10), 709-721.
4. Ghosh, S., Macrophage cholesterol homeostasis and metabolic diseases: critical role of cholesteryl ester mobilization. *Expert review of cardiovascular therapy* 2011, 9 (3), 329-340.
5. Ghosh, S.; Zhao, B.; Bie, J.; Song, J., Macrophage cholesteryl ester mobilization and atherosclerosis. *Vascular pharmacology* 2010, 52 (1), 1-10.
6. Ghosh, S.; Zhao, B.; Bie, J.; Song, J., Role of cholesteryl ester hydrolase in atherosclerosis. *Clinical Lipidology* 2009, 4 (5), 573-585.
7. Ghosh, S.; Bie, J.; Wang, J.; Yuan, Q.; Ghosh, S. S., Cholesterol removal from plaques and elimination from the body: change in paradigm to reduce risk for heart disease. 2014.
8. GHOSH, S., Cholesteryl ester hydrolase in human monocyte/macrophage: cloning, sequencing, and expression of full-length cDNA. *Physiological genomics* 2000, 2 (1), 1-8.
9. Zhao, B.; Fisher, B. J.; Clair, R. W.; Rudel, L. L.; Ghosh, S., Redistribution of macrophage cholesteryl ester hydrolase from cytoplasm to lipid droplets upon lipid loading. *Journal of lipid research* 2005, 46 (10), 2114-2121.
10. Bie, J.; Wang, J.; Marqueen, K. E.; Osborne, R.; Kakiyama, G.; Korzun, W.; Ghosh, S. S.; Ghosh, S., Liver-specific cholesteryl ester hydrolase deficiency attenuates sterol elimination in the feces and increases atherosclerosis in ldlr–/– mice. *Arteriosclerosis, thrombosis, and vascular biology* 2013, 33 (8), 1795-1802.
11. Bie, J.; Zhao, B.; Ghosh, S., Atherosclerotic lesion progression is attenuated by reconstitution with bone marrow from macrophage-specific cholesteryl ester hydrolase transgenic mice. *American Journal of Physiology-Regulatory, Integrative and Comparative Physiology* 2011, 301 (4), R967-R974.
12. Connelly, M. A.; Williams, D. L., Scavenger receptor BI: a scavenger receptor with a mission to transport high density lipoprotein lipids. *Current opinion in lipidology* 2004, 15 (3), 287-295.
13. Zhao, B.; Song, J.; Ghosh, S., Hepatic overexpression of cholesteryl ester hydrolase enhances cholesterol elimination and in vivo reverse cholesterol transport. *Journal of lipid research* 2008, 49 (10), 2212-2217.
14. Charach, G.; Grosskopf, I.; Rabinovich, A.; Shochat, M.; Weintraub, M.; Rabinovich, P., The association of bile acid excretion and atherosclerotic coronary artery disease. *Therapeutic advances in gastroenterology* 2011, 4 (2), 95-101.
15. Simonen, H.; Miettinen, T. A., Coronary artery disease and bile acid synthesis in familial hypercholesterolemia. *Atherosclerosis* 1987, 63 (2-3), 159-166.
16. Wirth, T.; Parker, N.; Yla-Herttuala, S., History of gene therapy. *Gene* 2013, 525 (2), 162-169.
17. Vannucci, L.; Lai, M.; Chiuppesi, F.; Ceccherini-Nelli, L.; Pistello, M., Viral vectors: a look back and ahead on gene transfer technology. *New Microbiol* 2013, 36 (1), 1-22.
18. Kim, B. Y.; Rutka, J. T.; Chan, W. C., Nanomedicine. *New England Journal of Medicine* 2010, 363 (25), 2434-2443.
19. Menjoge, A. R.; Kalman, R. M.; Tomalia, D. A., Dendrimer-based drug and imaging conjugates: design considerations for nanomedical applications. *Drug discovery today* 2010, 15 (5), 171-185.
20. Jin, L.; Zeng, X.; Liu, M.; Deng, Y.; He, N., Current progress in gene delivery technology based on chemical methods and nano-carriers. *Theranostics* 2014, 4 (3), 240-255.
21. Sajeesh, S.; Lee, T. Y.; Kim, J. K.; Hong, S. W.; Kim, S.; Yun, W. S.; Kim, S.; Chang, C.; Li, C.; Lee, D.-k., Efficient intracellular delivery and multiple-target gene silencing triggered by tripodal RNA based nanoparticles: A promising approach in liver-specific RNAi delivery. *Journal of Controlled Release* 2014, 196, 28-36.
22. Sun, Q.; Kang, Z.; Xue, L.; Shang, Y.; Su, Z.; Sun, H.; Ping, Q.; Mo, R.; Zhang, C., A collaborative assembly strategy for tumor-targeted siRNA delivery. *Journal of the American Chemical Society* 2015, 137 (18), 6000-6010.
23. Hu, Y.; Haynes, M. T.; Wang, Y.; Liu, F.; Huang, L., A highly efficient synthetic vector: nonhydrodynamic delivery of DNA to hepatocyte nuclei in vivo. *ACS nano* 2013, 7 (6), 5376-5384.
24. Zhang, Y.-N.; Poon, W.; Tavares, A. J.; McGilvray, I. D.; Chan, W. C., Nanoparticle—liver interactions: Cellular uptake and hepatobiliary elimination. *Journal of Controlled Release* 2016.
25. Li, L.; Wang, H.; Ong, Z. Y.; Xu, K.; Ee, P. L. R.; Zheng, S.; Hedrick, J. L.; Yang, Y.-Y., Polymer-and lipid-based nanoparticle therapeutics for the treatment of liver diseases. *Nano Today* 2010, 5 (4), 296-312.
26. Yang, H.; Morris, J. J.; Lopina, S. T., Polyethylene glycol-polyamidoamine dendritic micelle as solubility enhancer and the effect of the length of polyethylene glycol arms on the solubility of pyrene in water. *Journal of colloid and interface science* 2004, 273 (1), 148-154.
27. Svenson, S.; Tomalia, D. A., Dendrimers in biomedical applications—reflections on the field. *Advanced drug delivery reviews* 2012, 64, 102-115.
28. Figueroa, E. R.; Lin, A. Y.; Yan, J.; Luo, L.; Foster, A. E.; Drezek, R. A., Optimization of PAMAM-gold nanoparticle conjugation for gene therapy. *Biomaterials* 2014, 35 (5), 1725-1734.
29. Mallick, S.; Choi, J. S., Polyamidoamine (PAMAM) dendrimers modified with short oligopeptides for early endosomal escape and enhanced gene delivery. *International journal of pharmaceutics* 2015, 492 (1), 233-243.
30. Yang, J.; Zhang, Q.; Chang, H.; Cheng, Y., Surface-engineered dendrimers in gene delivery. *Chemical reviews* 2015, 115 (11), 5274-5300.
31. Liu, H.; Wang, H.; Xu, Y.; Guo, R.; Wen, S.; Huang, Y.; Liu, W.; Shen, M.; Zhao, J.; Zhang, G., Lactobionic acid-modified dendrimer-entrapped gold nanoparticles for targeted computed tomography imaging of human hepatocellular carcinoma. *ACS applied materials & interfaces* 2014, 6 (9), 6944-6953.
32. Patri, A. K.; Myc, A.; Beals, J.; Thomas, T. P.; Bander, N. H.; Baker, J. R., Synthesis and in vitro testing of J591 antibody-dendrimer conjugates for targeted prostate cancer therapy. *Bioconjugate chemistry* 2004, 15 (6), 1174-1181.
33. Ke, W.; Shao, K.; Huang, R.; Han, L.; Liu, Y.; Li, J.; Kuang, Y.; Ye, L.; Lou, J.; Jiang, C., Gene delivery targeted to the brain using an Angiopep-conjugated polyethyleneglycol-modified polyamidoamine dendrimer. *Biomaterials* 2009, 30 (36), 6976-6985.
34. Li, Z.; Huang, P.; Zhang, X.; Lin, J.; Yang, S.; Liu, B.; Gao, F.; Xi, P.; Ren, Q.; Cui, D., RGD-conjugated dendrimer-modified gold nanorods for in vivo tumor targeting and photothermal therapy†. *Molecular Pharmaceutics* 2009, 7 (1), 94-104.
35. Wang, H.; Zheng, L.; Peng, C.; Shen, M.; Shi, X.; Zhang, G., Folic acid-modified dendrimer-entrapped gold nanoparticles as nanoprobes for targeted CT imaging of human lung adencarcinoma. *Biomaterials* 2013, 34 (2), 470-480.
36. Li, Z.; Huang, P.; He, R.; Lin, J.; Yang, S.; Zhang, X.; Ren, Q.; Cui, D., Aptamer-conjugated dendrimer-modified quantum dots for cancer cell targeting and imaging. *Materials letters* 2010, 64 (3), 375-378.
37. Lewis, D. R.; Petersen, L. K.; York, A. W.; Zablocki, K. R.; Joseph, L. B.; Kholodovych, V.; Prud'homme, R. K.; Uhrich, K. E.; Moghe, P. V., Sugar-based amphiphilic nanoparticles arrest atherosclerosis in vivo. *Proceedings of the National Academy of Sciences* 2015, 112 (9), 2693-2698.
38. Tachibana, Y.; Munisso, M. C.; Kamata, W.; Kitagawa, M.; Harada-Shiba, M.; Yamaoka, T., Quick nuclear transportation of siRNA and in vivo hepatic ApoB gene silencing with galactose-bearing polymeric carrier. *Journal of biotechnology* 2014, 175, 15-21.
39. Lee, M. H.; Han, J. H.; Kwon, P.-S.; Bhuniya, S.; Kim, J. Y.; Sessler, J. L.; Kang, C.; Kim, J. S., Hepatocyte-targeting single galactose-appended naphthalimide: a tool for intracellular thiol imaging in vivo. *Journal of the American Chemical Society* 2012, 134 (2), 1316-1322.
40. Jevprasesphant, R.; Penny, J.; Jalal, R.; Attwood, D.; McKeown, N.; D'emanuele, A., The influence of surface modification on the cytotoxicity of PAMAM dendrimers. *International journal of pharmaceutics* 2003, 252 (1), 263-266.

41. Wang, W.; Xiong, W.; Wan, J.; Sun, X.; Xu, H.; Yang, X., The decrease of PAMAM dendrimer-induced cytotoxicity by PEGylation via attenuation of oxidative stress. *Nanotechnology* 2009, 20 (10), 105103.
42. Zahr, A. S.; Davis, C. A.; Pishko, M. V., Macrophage uptake of core-shell nanoparticles surface modified with poly (ethylene glycol). *Langmuir* 2006, 22 (19), 8178-8185.
43. Zhang, Y.; Kohler, N.; Zhang, M., Surface modification of superparamagnetic magnetite nanoparticles and their intracellular uptake. *Biomaterials* 2002, 23 (7), 1553-1561.
44. Lipka, J.; Semmler-Behnke, M.; Sperling, R. A.; Wenk, A.; Takenaka, S.; Schleh, C.; Kissel, T.; Parak, W. J.; Kreyling, W. G., Biodistribution of PEG-modified gold nanoparticles following intratracheal instillation and intravenous injection. *Biomaterials* 2010, 31 (25), 6574-6581.
45. Pelaz, B.; del Pino, P.; Maffre, P.; Hartmann, R.; Gallego, M.; Rivera-Fernandez, S.; de la Fuente, J. M.; Nienhaus, G. U.; Parak, W. J., Surface functionalization of nanoparticles with polyethylene glycol: effects on protein adsorption and cellular uptake. *ACS nano* 2015, 9 (7), 6996-7008.
46. Kim, S. K.; Park, K. M.; Singha, K.; Kim, J.; Ahn, Y.; Kim, K.; Kim, W. J., Galactosylated cucurbituril-inclusion polyplex for hepatocyte-targeted gene delivery. *Chemical Communications* 2010, 46 (5), 692-694.
47. Lakshminarayanan, A.; Reddy, B. U.; Raghav, N.; Ravi, V. K.; Kumar, A.; Maiti, P. K.; Sood, A.; Jayaraman, N.; Das, S., A galactose-functionalized dendritic siRNA-nanovector to potentiate hepatitis C inhibition in liver cells. *Nanoscale* 2015, 7 (40), 16921-16931.
48. Lai, C. H.; Lin, C. Y.; Wu, H. T.; Chan, H. S.; Chuang, Y. J.; Chen, C. T.; Lin, C. C., Galactose encapsulated multifunctional nanoparticle for HepG2 cell internalization. *Advanced Functional Materials* 2010, 20 (22), 3948-3958.
49. Luong, D.; Kesharwani, P.; Deshmukh, R.; Amin, M. C. I. M.; Gupta, U.; Greish, K.; Iyer, A. K., PEGylated PAMAM dendrimers: Enhancing efficacy and mitigating toxicity for effective anticancer drug and gene delivery. *Acta Biomaterialia* 2016, 43, 14-29.
50. Shen, W.; van Dongen, M. A.; Han, Y.; Yu, M.; Li, Y.; Liu, G.; Holl, M. M. B.; Qi, R., The role of caveolin-1 and syndecan-4 in the internalization of PEGylated PAMAM dendrimer polyplexes into myoblast and hepatic cells. *European Journal of Pharmaceutics and Biopharmaceutics* 2014, 88 (3), 658-663.
51. Bie, J.; Wang, J.; Yuan, Q.; Kakiyama, G.; Ghosh, S. S.; Ghosh, S., Liver-specific transgenic expression of cholesteryl ester hydrolase reduces atherosclerosis in Ldlr−/− mice. *Journal of lipid research* 2014, 55 (4), 729-738.
52. Liu, L.; He, H.; Zhang, M.; Zhang, S.; Zhang, W.; Liu, J Hyaluronic acid-decorated reconstituted high density lipoprotein targeting atherosclerotic lesions. *Biomaterials* 2014, 35 (27), 8002-8014.
53. Duivenvoorden, R.; Tang, J.; Cormode, D. P.; Mieszawska, A. J.; Izquierdo-Garcia, D.; Ozcan, C.; Otten, M. J.; Zaidi, N.; Lobatto, M. E.; van Rijs, S. M., A statin-loaded reconstituted high-density lipoprotein nanoparticle inhibits atherosclerotic plaque inflammation. *Nature communications* 2014, 5.
54. Sun, T.; Simmons, R.; Huo, D.; Pang, B.; Zhao, X.; Kim, C. W.; Jo, H.; Xia, Y., Targeted Delivery of Anti-miR-712 by VCAM1-Binding Au Nanospheres for Atherosclerosis Therapy. *ChemNanoMat* 2016, 2 (5), 400-406.
55. Wolfram, J. A.; Donahue, J. K., Gene therapy to treat cardiovascular disease. *Journal of the American Heart Association* 2013, 2 (4), e000119.
56. Tuteja, S.; Rader, D. J., High-Density Lipoproteins in the Prevention of Cardiovascular Disease: Changing the Paradigm. *Clinical Pharmacology & Therapeutics* 2014, 96 (1), 48-56.
57. Zhao, B.; Natarajan, R.; Ghosh, S., Human liver cholesteryl ester hydrolase: cloning, molecular characterization, and role in cellular cholesterol homeostasis. *Physiological genomics* 2005, 23 (3), 304-310.
58. Wang, J.; Bie, J.; Ghosh, S., Intracellular Cholesterol Transport Proteins Enhance Hydrolysis of HDL-delivered Cholesteryl Esters and Facilitate Preferential Elimination of Resulting Cholesterol into Bile. *Journal of Lipid Research* 2016, jlr. M069682.
59. Yang, H.; Kao, W. J., Synthesis and characterization of nanoscale dendritic RGD clusters for potential applications in tissue engineering and drug delivery. *International journal of nanomedicine* 2007, 2 (1), 89.
60. Xu, Y.; Jin, X.; Ping, Q.; Cheng, J.; Sun, M.; Cao, F.; You, W.; Yuan, D., A novel lipoprotein-mimic nanocarrier composed of the modified protein and lipid for tumor cell targeting delivery. *Journal of Controlled Release* 2010, 146 (3), 299-308.
61. An, S.; He, D.; Wagner, E.; Jiang, C., Peptide-like Polymers Exerting Effective Glioma-Targeted siRNA Delivery and Release for Therapeutic Application. *Small* 2015, 11 (38), 5142-5150.
62. Kim, K.; Kim, J. H.; Park, H.; Kim, Y.-S.; Park, K.; Nam, H.; Lee, S.; Park, J. H.; Park, R.-W.; Kim, I.-S., Tumor-homing multifunctional nanoparticles for cancer theragnosis: simultaneous diagnosis, drug delivery, and therapeutic monitoring. *Journal of controlled release* 2010, 146 (2), 219-227.
63. Bi, Y.; Liu, L.; Lu, Y.; Sun, T.; Shen, C.; Chen, X.; Chen, Q.; An, S.; He, X.; Ruan, C., T7 peptide-functionalized PEG-PLGA micelles loading with carmustine for targeting therapy of glioma. *ACS Applied Materials & Interfaces* 2016.
64. Marshall, M. V.; Draney, D.; Sevick-Muraca, E. M.; Olive, D. M., Single-dose intravenous toxicity study of IRDye 800CW in Sprague-Dawley rats. *Molecular Imaging and Biology* 2010, 12 (6), 583-594.
65. Cruz, L. J.; Stammes, M. A.; Que, I.; van Beek, E. R.; Knol-Blankevoort, V. T.; Snoeks, T. J.; Chan, A.; Kaijzel, E. L.; Lowik, C. W., Effect of PLGA NP size on efficiency to target traumatic brain injury. *Journal of Controlled Release* 2016, 223, 31-41.

Example 3. Use of Additional Therapeutic Agents to Attenuate Atherosclerosis

Figure 21:
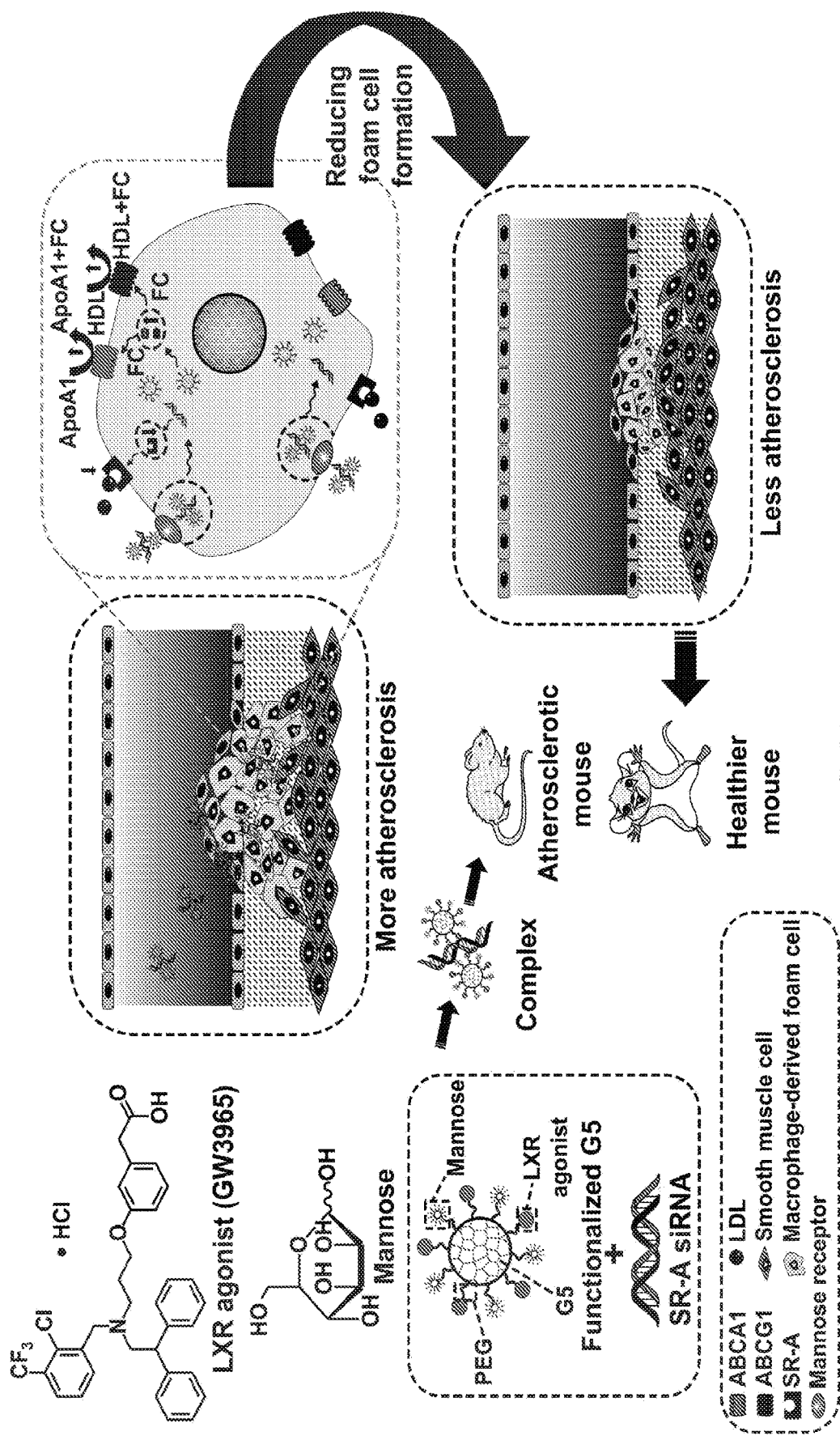
FIG. 21. Schematic to illustrate the two-pronged approach to attenuate atherosclerosis.

In addition to the delivery of LXR agonist and the expression vector encoding CEH, additional agents for co-delivery were considered. A schematic to illustrate the two-pronged approach to attenuate atherosclerosis is shown in FIG. 21. In this example, the two-pronged complex consists of mannose-functionalized PAMAM dendrimer G5 conjugated with LXR agonist (mDNP-LXR-L) and complexed with SR-A siRNA. With the administration of this complex, cellular cholesterol accumulation can be attenuated by simultaneous targeting of two processes, namely, reduced lipoprotein cholesterol uptake via knockdown of Scavenger Receptor SR-A by siRNA and increased cholesterol efflux via unregulated expression of atheroprotective transporter proteins ABCA1 and ABCG1 induced by LXR agonist.

Figure 22A:
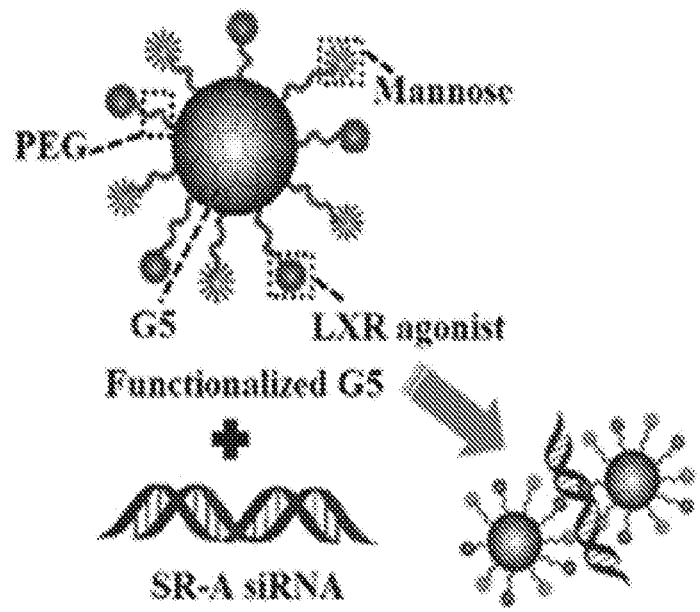
FIG. 22A-22E. Characterization of mDNP-siRNA complexes and delivery to macrophages.
Figure 22B:
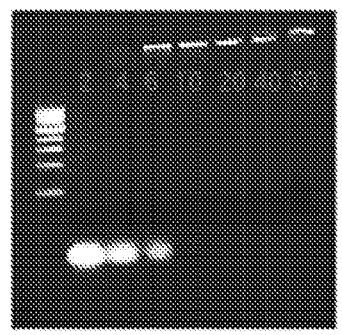
Figure 22C:
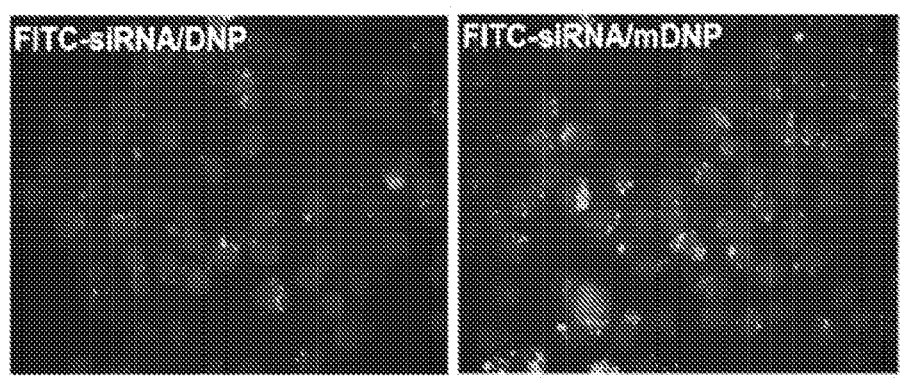
Figure 22D:
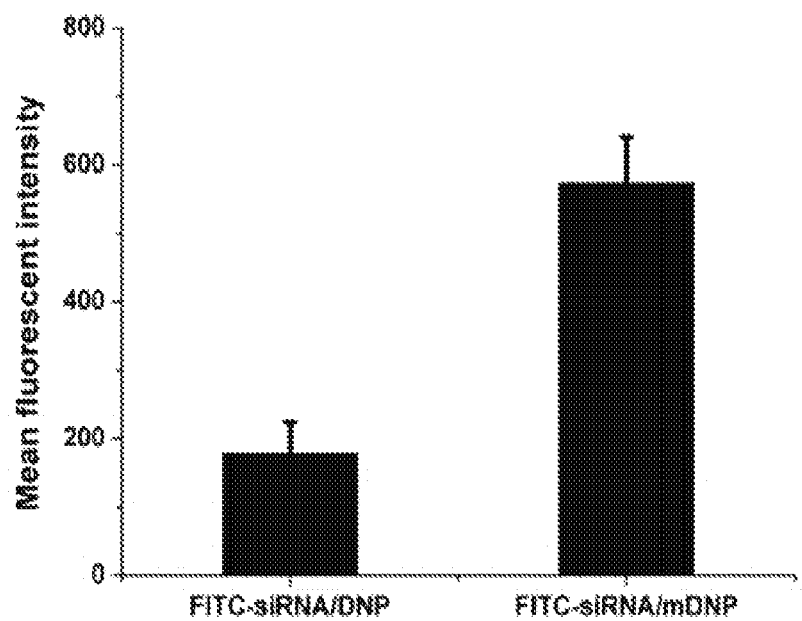
Figure 22E:
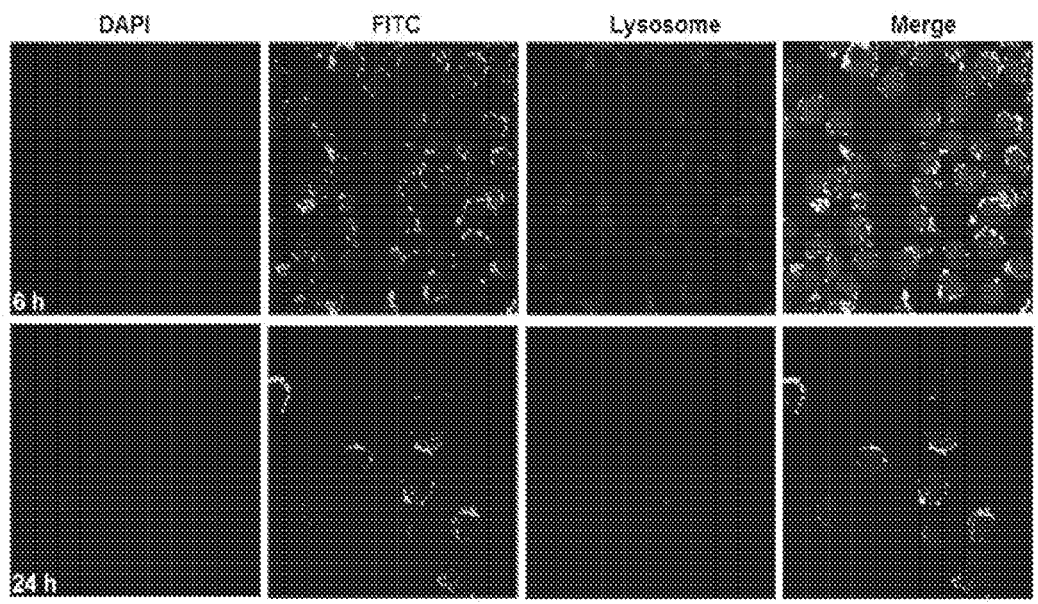

These particles comprising both LXR and the siRNA for SR-A were characterized for delivery to macrophages. First the PEGyated mDNPs were complexed with siRNA to SR-A (FIG. 22a). Gel retardation assay of mDNP/siRNA complexes at different weight ratios show that siRNA is fully complexed to mDNP-LXR-L above the ratio of 1:10 (FIG. 22b). Next, delivery of FITC-labeled siRNA complexed to either non-functionalized DNP or mDNP to macrophages was compared. Increased FITC (Green) fluorescence demonstrated higher uptake of siRNA using mDNPs (FIG. 22c). Uptake was quantified by Flow Cytometry where fluorescence of FITC conjugated DNP is measured as Mean Fluorescent Intensity (FIG. 22d). To monitor lysomal escape of siRNA delivered via siRNA/mDNP complexes, following incubation with FITC-labeled siRNA/mDNP complexes, macrophages were fixed and stained for lysosome marker (FIG. 22e). The co-localization of FITC-labeled siRNA and lysosomal marker is apparent in the merged images. After 24 hours, no overlap is noted between the lysosomal maker and siRNA demonstrating complete escape of siRNA from lysosome.

Figure 23A:
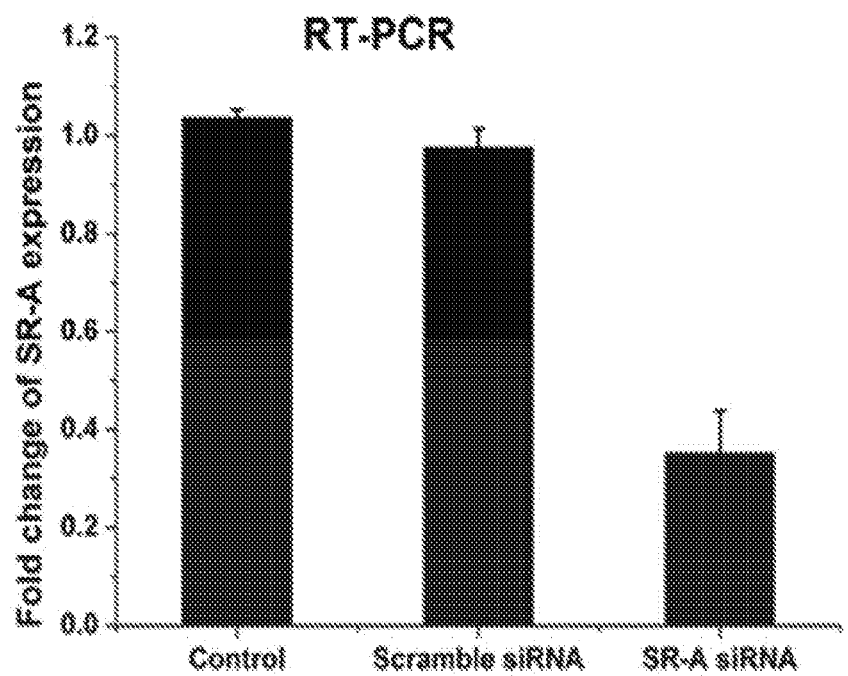
FIG. 23A-23C. Intracellular functionality of the siRNA delivered via siRNA/mDNP complexes. Macrophages were incubated with siRNA/mDNP complexes and expression of SR-A as well as effects on lipid accumulation were monitored as functional parameters.
Figure 23B:
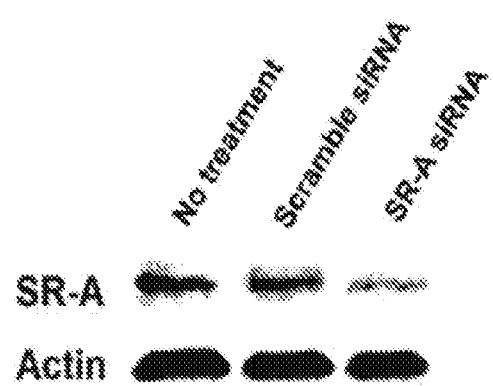
Figure 23C:
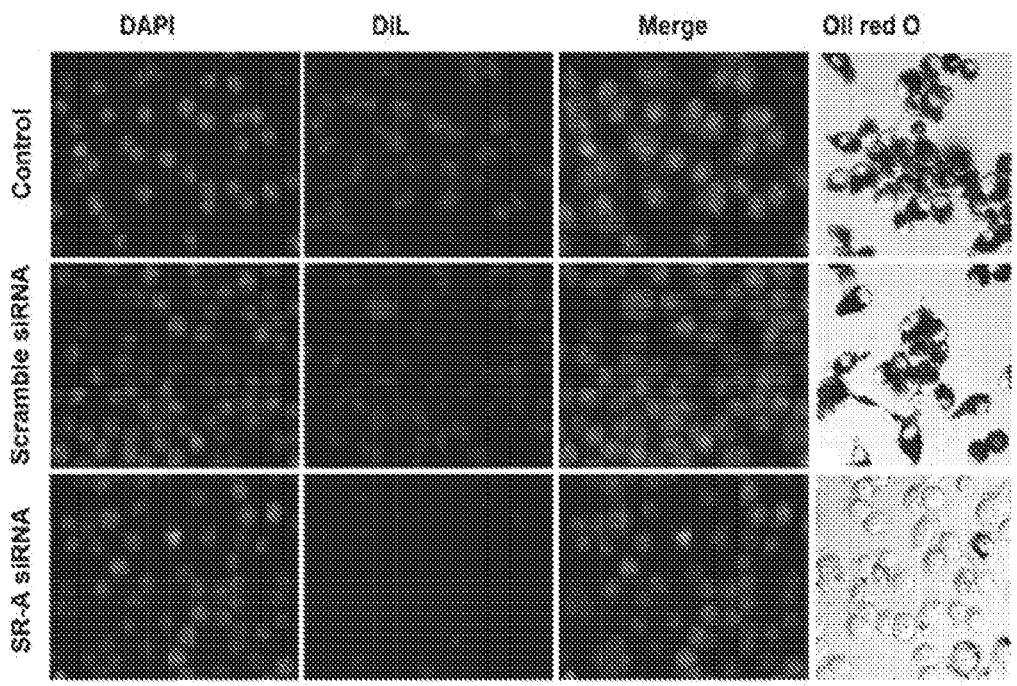

Next, the intracellular functionality of the siRNA delivered via siRNA/mDNP complexes were examined. Macrophages were incubated with siRNA/mDNP complexes and expression of SR-A as well as effects on lipid accumulation were monitored as functional parameters. SR-A mRNA levels were determined by RT-qPCR and significant reduction in SR-A mRNA level was seen in cells exposed to siRNA/mDNP compared to those exposed to complexes containing non-specific scrambled siRNA (FIG. 23a). Following treatment with siRNA/mDNP complexes, total cellular proteins were analyzed by Western blot analysis using antibody to SR-A (FIG. 23b). Consistent with the observed changes in mRNA levels shown in FIG. 23a, while no change in SR-A protein levels was noted in cells exposed to scrambled siRNA, cells exposed to SR-A siRNA complexes show a dramatic decrease in SR-A immuno-reactive band (FIG. 23b). Functional consequence of SR-A siRNA/mDNP mediated reduction in SR-A were assessed by monitoring the uptake of DiI labeled oxLDL (FIG. 23c). Compared to cells exposed to complexes containing scrambled siRNA, reduced uptake of DiI-labeled oxLDL was seen in cells exposed to complexes containing SR-A siRNA. Cellular lipids were also stained by Oil red O and consistent with reduced uptake of DiI-labeled oxLDL, reduced Oil Red O staining was seen in cells exposed to SR-A siRNA containing complexes (FIG. 23c).

Figure 24A:
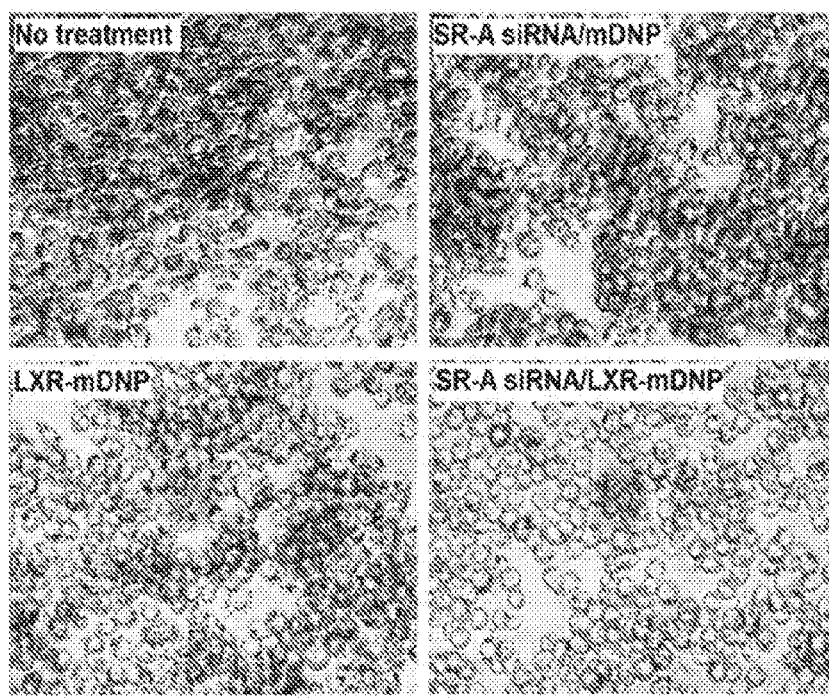
FIG. 24A-24B. Treatment of macrophages with siRNA to SR-A along with LXR-L is more effective in decreasing cellular lipid accumulation.
Figure 24B:
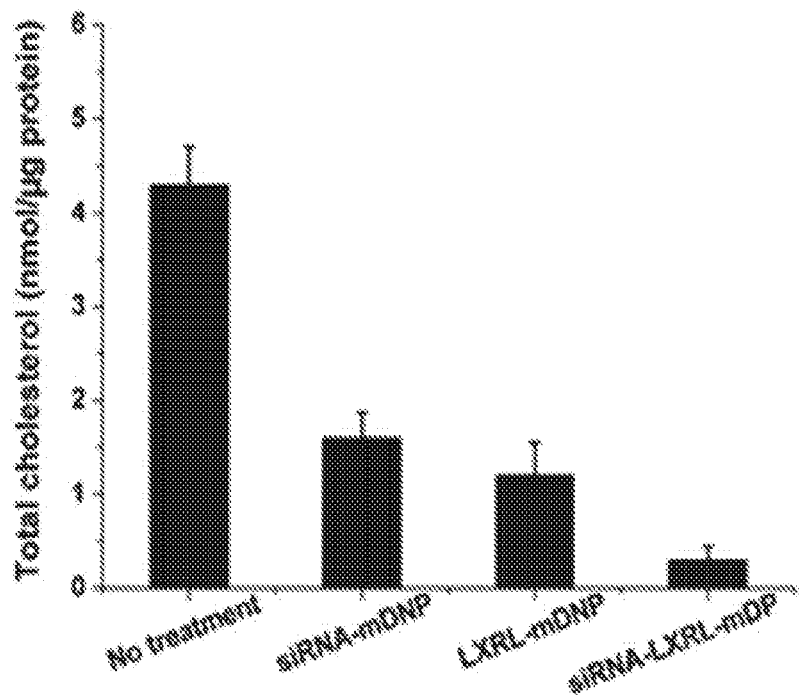

Next, macrophages were analyzed using the two-prong approach. Treatment of macrophages with siRNA to SR-A along with LXR-L was more effective in decreasing cellular lipid accumulation (FIG. 24). Macrophages were either left untreated or treated with SR-A siRNA/mDNP or LXR-L-mDNP or SR-A siRNA/LXR-L mDNP complexes and then incubated with AcLDL (50 mg/ml) for 48 h. Following a brief wash with PBS, cells were fixed and stained with Oil Red O. Representative images are shown in FIG. 24a. Total lipids were extracted from a parallel set of cells and total cholesterol content determined by HPLC and normalized to total cellular protein. Data are presented as nmoles/mg protein (Mean±SD, n=6) in FIG. 24b.

Figure 25:
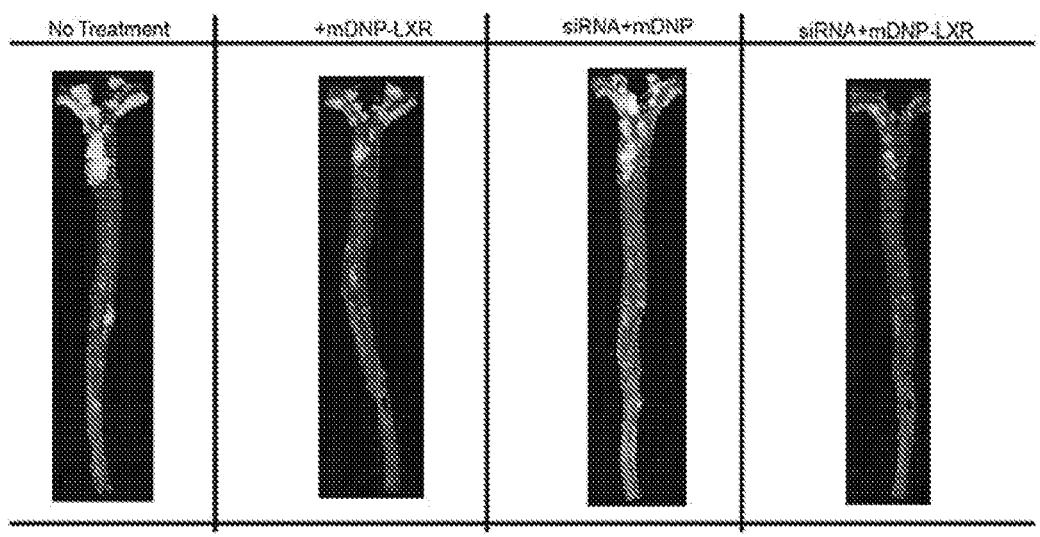
FIG. 25. Higher reduction in atherosclerotic lesion formation using the two-pronged approach with siRNA to SR-A along with LXR-L. LDLR−/− mice were fed a high fat high cholesterol containing Western diet (TD88137) for 16 weeks and then switched to standard rodent chow for additional 4 weeks. Mice were then divided into four groups and either received no treatment or received 4 weekly intravenous injections of mDNP-LXR-L or siRNA/mDNP complex or siRNA/mDNP-LXR-L complexes. After an overnight fast, mice were euthanized and entire aorta from the heart to the iliary bifurcation was carefully removed, cleaned of any adventitious tissue and prepared for enface analyses. Representative images from each group are shown.

Finally, atherosclerotic lesion formation was investigated using the two-pronged approach with siRNA to SR-A along with LXR-L. LDLR−/− mice were fed a high fat high cholesterol containing Western diet (TD88137) for 16 weeks and then switched to standard rodent chow for additional 4 weeks. Mice were then divided into four groups and either received no treatment or received 4 weekly intravenous injections of mDNP-LXR-L or siRNA/mDNP complex or siRNA/mDNP-LXR-L complexes. After an overnight fast, mice were euthanized and entire aorta from the heart to the iliary bifurcation was carefully removed, cleaned of any adventitious tissue and prepared for enface analyses. Representative images from each group are shown in FIG. 25. It was found that there was a higher reduction in atherosclerotic lesion formation using the two-pronged approach with siRNA to SR-A along with LXR-L (FIG. 25).

```
Sequences
Human macrophage cholesteryl ester hydrolase (CEH) coding sequence
(See Accession # AY-268104)
                                                           (SEQ ID NO: 1)
atgtggctccgtgcctttatcctggccactctctctgcttccgcggcttgggggcatccgtcctcgcc acctgtggtggacaccgtgcatggcaaagtgctggggaagttcgtcagcttagaaggatttgcacagc ctgtggccatttcctgggaatcccttttgccaagccgcctcttggacccctgaggtctactccaccg cagcctgcagaaccatggagctttgtgaagaatgccacctcgtaccctcctatgtgcacccgagatcc caaggcggggcagttactctcagagctatttacaaaccgaaaggagaacattcctctcaagctttctg aagactgtctttacctcaatatttacactcctgctgacttgaccaagaaaaacaggctgccggtgatg gtgtggatccacggagggggctgatggtgggtgcggcatcaacctatgatgggctggcccttgctgc ccatgaaaacgtggtggtggtgaccattcaatatcgcctgggcatctggggattcttcagcacagggg atgaacacagccgggggaactggggtcacctggaccaggtggctgccctgcgctgggtccagcacaac attgccagctttggagggaacccaggctctgtgaccatctttggagagtcagcgggaggagaaagtgt ctctgttcttgttttgtctccattggccaagaacctcttccacgggccatttctgagagtggcgtgg ccctcacttctgttctggtgaagaaaggtgatgtcaagcccttggctgagcaaattgctatcactgct gggtgcaaaaccaccacctctgctgtcatggttcactgcctgcgacagaagacggaagaggagctctt ggagacgacattgaaaatgaaattcttatctctggacttacagggagaccccagagagagtcaacccc
```

```
ttctgggcactgtgattgatgggatgctgctgctgaaaacacctgaagagcttcaagctgaaaggaat ttccacactgtcccctacatggtcggaattaacaagcaggagtttggctggttgattccaatgcagtt gatgagctatccactctccgaagggcaactggaccagaagacagccatgtcactcctgtggaagtcct atccccttgtttgcattgctaaggaactgattccagaagccactgagaaatacttaggaggaacagac gacactgtcaaaaagaaagacctgttcctggacttgatagcagatgtgatgtttggtgtcccatctgt gattgtggcccggaaccacagagatgctggagcacccacctacatgtatgagtttcagtaccgtccaa gcttctcatcagacatgaaacccaagacggtgataggagaccacggggatgagctcttctccgtcttt ggggcccattttaaaagagggtgcctcagaagaggagatcagacttagcaagatggtgatgaaatt ctgggccaactttgctcgcaatggaaaccccaatggggaagggctgccccactggccagagtacaacc agaaggaagggtatctgcagattggtgccaacacccaggcggcccagaagctgaaggacaaagaagta gctttctggaccaacctctttgccaagaaggcagtggagaagccaccccagacagaacacatagagct gtga cDNA for human macrophage cholesteryl ester hydrolase (CEH) mRNA
(Accession # AY268104)
                                                          (SEQ ID NO: 2)
   1 ctgtacagag acctcgcagg ccccgagaac tgtcgccttc cacgatgtgg ctccgtgcct 61 ttatcctggc cactctctct gcttccgcgg cttgggggca tccgtcctcg ccacctgtgg 121 tggacaccgt gcatgcaaa gtgctgggga agttcgtcag cttagaagga tttgcacagc 181 ctgtggccat tttcctggga atccctttg ccaagccgcc tcttggaccc ctgaggtcta 241 ctccaccgca gctgcagaa ccatggagct tgtgaagaa tgccacctcg tacccctcta 301 tgtgcacccg agatcccaag gcggggcagt tactctcaga gctatttaca aaccgaaagg 361 agaacattcc tctcaagctt tctgaagact gtctttacct caatatttac actcctgctg 421 acttgaccaa gaaaaacagg ctgccggtga tggtgtggat ccacggaggg gggctgatgg 481 tgggtgcggc atcaacctat gatgggctgg cccttgctgc ccatgaaaac gtggtggtgg 541 tgaccattca atatcgcctg gcatctggg gattcttcag cacaggqgat gaacacagcc 601 gggggaactg gqgtcacctg gaccaggtgg ctgccctgcg ctgggtccag acaacattg 661 ccagctttgg agggaaccca ggctgtgtga ccatctttgg agagtcagcg ggaggagaaa 721 gtgtatctgt tcttgttttg tctccattgg ccaagaacct cttccaccgg gccatttctg 781 agagtggcgt ggccctcact tctgttctgg tgaagaaagg tgatgtcaag cccttggctg 841 agcaaattgc tatcactgct gqgtgcaaaa ccaccacctc tgctgtcatg gttcactgcc 901 tgcgacagaa gacggaagag gagctcttgg agacgacatt gaaaatgaaa ttcttatctc 961 tggacttaca gggagacccc agagagagtc aacccttct gggcactgtg attgatggga 1021 tgctgctgct gaaaacacct gaagagcttc aagctgaaag gaatttgcac actgtcccct 1081 acatggtcgg aattaacaag caggagtttg gctggttgat tccaatgcag ttgatgagct 1141 atccactctc cgaagggcaa ctggaccaga gacagccat gtcactcctg tggaagtcct 1201 atccccttgt ttgcattgct aaggaactga ttccagaagc cactgagaaa tacttaggag 1261 gaacagacga cactgtcaaa agaaagacc tgttcctgga cttgatagca gatgtgatgt 1321 ttggcgtccc atctgtgatt gtggcccgga accacagaga tgctggagca cccacctaca 1381 tgtatgagtt tcagtaccgt ccaagcttct catcagacat gaaacccaag acggtgatag 1441 gagaccacgg ggatgagctc ttctccgtct ttggggcccc attttaaaa gagggtgcct 1501 cagaagagga gatcagactt agcaagatgg tgatgaaatt ctgggccaac tttgctcgca 1561 atggaaaccc caatggggaa gggctgcccc actggccaga gtacaaccag aaggaagggt
```

-continued

```
1621 atctgcagat tggtgccaac acccaggcgg cccagaagct gaaggacaaa gaagtagctt 1681 tctggaccaa cctctttgcc aagaaggcag tggagaagcc accccagaca gaacacatag 1741 agctgtgaat gaagatccag cggccttgg gagcctggag gagcaaagac tggggtcttt 1801 tgcgaaaggg attgcaggct cagaaggcat cttaccatgg ctggggaatt gtctggtggt 1861 gggggcagg ggacagaggc catgaaggag caagttttgt attgtgacct cagctttggg 1921 aataagatct tttgaaggca aaaaaaa
```

Human macrophage CEH protein sequence (SEQ ID NO: 3)

MWLRAFILATLSASAAWGHPSSPPVVDTVHGKVLGKFVSLEGFAQPVAIFLGIPFAKPPLGPLRSTPPQPAEPWS
FVKNATSYPPMCTRDPKAGQLLSELFTNRKENIPLKLSEDCLYLNIYTPADLTKKNELPVMVWIHGGGLMVGAAS
TYDGLALAAHENVVVVTIQYRLGIWGFFSTGDEHSRGNWGHLDQVAALRWVQDNIASFGGNPGSVTIFGESAGGE
SVSVLVLSPLAKNLFHRAISESGVALTSVLVKKGDVKPLAEQIAITAGCKTTTSAVMVHCLRQKTEEELLETTLK
MKFLSLDLQGDPRESQPLLGTVIDGMLLLKTPEELQAERNFHTVPYMVGINKQEFGWLIPMQLMSYPLSEGQLDQ
KTAMSLLWKSYPLVCIAKELIPEATEKYLGGTDDTVKKKDLFLDLIADVMFGVPSVIVARNHRDAGAPTYMYEFQ
YRPSFSSDMKPKTVIGDHGDELFSVFGAPPFLKEGASEEEIRLSKMVMKFWANFARNGNPNGEGLPHWPEYNQKEG
YLQIGANTQAAQKLKDKEVAFWTNLFAKKAVEKPPQTEHIEL

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of treating atherosclerosis, comprising; administering to a subject in need thereof a nanoparticle comprising:
   a polyamidoamine (PAMAM) dendrimer;
   a carbohydrate moiety, wherein the carbohydrate moiety is mannose or galactose, wherein the carbohydrate moiety is linked to the polyamidoamine (PAMAM) dendrimer via a polyethylene glycol (PEG) linker, and wherein the PEG linker comprises at least four individual PEG units; and
   an intracellular cholesteryl ester modulator to enhance removal of unesterified or free cholesterol and thereby treat atherosclerosis, and
   wherein the intracellular cholesteryl ester modulator is linked to the PAMAM dendrimer on the surface of the nanoparticle.

2. The method of claim 1, wherein the PEG linker comprises PEG with a molecular weight of about 3.5 kDa.

3. The method of claim 1, wherein the intracellular cholesteryl ester modulator is a liver-x-receptor (LXR) agonist.

4. The method of claim 3, wherein the LXR agonist is T0901317 or GW3965.

* * * * *